United States Patent
Burnett et al.

(10) Patent No.: US 6,664,273 B2
(45) Date of Patent: Dec. 16, 2003

(54) PIPERIDINE BASED MCH ANTAGONISTS FOR TREATMENT OF OBESITY AND CNS DISORDERS

(75) Inventors: Duane A. Burnett, Bernardsville, NJ (US); Wen-Lian Wu, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/303,205

(22) Filed: Nov. 25, 2002

(65) Prior Publication Data

US 2003/0199549 A1 Oct. 23, 2003

Related U.S. Application Data

(60) Provisional application No. 60/333,367, filed on Nov. 26, 2001.

(51) Int. Cl.[7] .................... A61K 31/445; C07D 211/52
(52) U.S. Cl. .................... 514/327; 546/217; 546/229; 546/224; 546/214; 546/213; 546/208; 546/112; 514/331; 514/329; 514/326; 514/299
(58) Field of Search ................... 514/327, 326, 514/329, 331, 299; 546/217, 208, 213, 214, 224, 229, 112, 183

(56) References Cited

U.S. PATENT DOCUMENTS

| | | | |
|---|---|---|---|
| 3,083,205 A | * | 3/1963 | Janssen ............... 546/224 |
| 5,908,830 A | | 6/1999 | Smith et al. |
| 6,043,246 A | | 3/2000 | Fukami et al. |

FOREIGN PATENT DOCUMENTS

| | | |
|---|---|---|
| EP | 0503548 B1 | 3/1992 |
| WO | WO 99/64394 | 12/1999 |
| WO | WO 99/27845 | 5/2000 |
| WO | WO 01/21577 A2 | 3/2001 |
| WO | WO 01/82925 A1 | 11/2001 |
| WO | WO 01/87834 A1 | 11/2001 |
| WO | WO 02/083134 A1 | 10/2002 |
| WO | WO 03/033480 A1 | 4/2003 |

OTHER PUBLICATIONS

Shimada et al., 1988, "Mice Lacking Melanin–concentrating Hormone are Hypophagic and Lean", *Nature*, 396:670–674.

Borowsky et al., 2002, "Antidepressant, anixiolytic and anorectic effects of a melanin–concentrating hormone–1 receptor antagonist", *Nature Medicine*, 8:825–830.

* cited by examiner

*Primary Examiner*—Charanjit S. Aulakh
(74) *Attorney, Agent, or Firm*—William Y. Lee

(57) ABSTRACT

The present invention discloses compounds, which are novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

29 Claims, No Drawings

PIPERIDINE BASED MCH ANTAGONISTS FOR TREATMENT OF OBESITY AND CNS DISORDERS

CROSS REFERENCE TO RELATED APPLICATIONS

This application claims the benefit of U.S. Provisional Application 60/333,367 filed on Nov. 26, 2001.

FIELD OF THE INVENTION

This invention relates to antagonists of melanin-concentrating hormone (MCH) and their use in the treatment of obesity, eating disorders and diabetes, pharmaceutical compositions containing the compounds, and methods of treatment using the compounds.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., *Nature*, Vol. 396 (Dec. 17 1998), pp. 670–673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. Further, MCH receptor antagonists may also be useful in the treatment of depression and/or anxiety. Borowksy et al., *Nature Medicine*, 8, pp. 825–830 (Aug. 1, 2002).

SUMMARY OF THE INVENTION

The present invention relates to the compound represented by structural formula I:

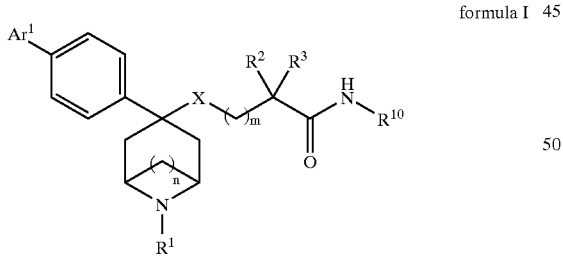

formula I or a pharmaceutically acceptable salt or solvate of said compound, wherein:

$Ar^1$ is aryl, heteroaryl, $(R^7)_p$-substituted aryl or $(R^7)_p$-substituted heteroaryl, wherein p is a number from 1 to 5 and when p is more than 1, each $R^7$ can be the, same or different and each $R^7$ is hydrogen or independently selected from the group consisting of OH, alkoxy, CN, halogen, $NR^8R^9$, $C(O)NR^8R^9$, $N(R^8)C(O)R^5$, $N(R^8)S(O_2)R^5$, $S(O_2)NR^8R^9$, $C(O)OR^8$, $OCF_3$, $CF_3$, $S(O_2)R^5$ and $C(O)R^5$, or two adjacent $R^7$ can be joined together to form an alkylenedioxy selected from

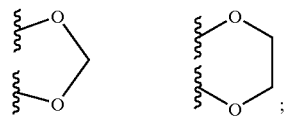

or when $Ar^1$ is an $(R^7)_p$-substituted aryl, where $R^7$ and the phenyl ring to which it is shown attached in Formula I can be bridged by Y as shown by

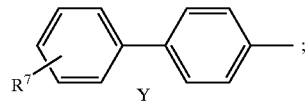

$R^1$ is H, alkyl, aryl, aralkyl, aryloxyalkyl, hydroxyalkyl, alkoxyalkyl, heteroaryl, (styrenyl)methyl, heteroaralkyl, cycloalkylalkyl, heterocyclyl, cycloalkyl, wherein each of said alkyl, aralkyl, aryloxyalkyl, hydroxyalkyl, alkoxyalkyl, heteroaralkyl, cycloalkylalkyl, heterocyclyl and cycloalkyl can be unsubstituted or optionally substituted with one or more $R^7$ moieties which can be the same or different, $-S(O_2)NR^8R^9$, $S(O_2)R^5$, $C(O)OR^8$, $C(O)R^5$, $C(O)NR^8R^9$, $(R^7)_p$-substituted aryl or $(R^7)_p$-substituted heteroaryl, wherein p is a number from 1 to 5 and when p is more than 1, each $R^7$ can be the same or different and each $R^7$ is hydrogen or independently selected from the group consisting of alkyl, cycloalkyl, OH, alkoxy, CN, halogen, heteroaryl, OC(O)OH; aryloxy, $NR^8R^9$, $C(O)NR^8R^9$, $N(R^8)C(O)R^5$, $N(R^8)S(O_2)R^5$, $S(O_2)NR^8R^9$, $C(O)OR^8$, $OCF_3$, $CF_3$, $SR^5$, $S(O_2)R^5$ and $C(O)R^5$, or two adjacent $R^7$ can be joined together to form an alkylenedioxy selected from

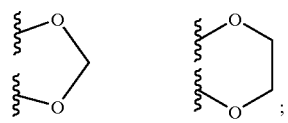

$R^2$, $R^3$, $R^8$ and $R^9$ can each be the same or different and each independently H or alkyl;

or $R^2$ and $R^3$ together are alkylene and with the carbon to which they are attached form a 3 to 7 membered ring;

$R^4$ is H, alkyl, aralkyl, $R^5C(O)$, $R^5S(O_2)$ or

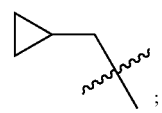

$R^5$ is alkyl or aryl;

$R^6$ is alkyl, aralkyl or $(R^7)_p$-substituted aralkyl, wherein p is a number from 1 to 5 and when p is more than 1, each $R^7$ can be the same or different and each $R^7$ is hydrogen or independently selected from the group consisting of OH, alkoxy, CN, halogen, $NR^8R^9$, $C(O)NR^8R^9$, $N(R^8)C(O)R^5$, $N(R^8)S(O_2)R^5$, $-S(O_2)NR^8R^9$, $C(O)OR^8$, $OCF_3$, $CF_3$, $S(O_2)R^5$ and $C(O)R^5$, $R^{10}$ is aryl, heteroaryl, $(R^7)_p$-substituted aryl or $(R^7)_p$-substituted heteroaryl, wherein p is a number from 1 to 5 and when p is more than 1, each $R^7$ can be the same or different and each $R^7$ is hydrogen or independently selected from the group consisting of OH, alkoxy, CN, halogen, $NR^8R^9$, $C(O)NR^8R^9$, $N(R^8)C(O)R^5$, $N(R^8)S(O_2)R^5$, $S(O_2)NR^8R^9$, $C(O)OR^8$, $OCF_3$, $CF_3$, $S(O_2)R^5$, $C(O)R^5$ and heterocycloalkyl or $R^{10}$ is an alkylene or heteroalkylene where said alkylene or heteroalkylene is attached to the N of $NR^{10}$ to form a heterocyclyl ring selected from the group consisting of

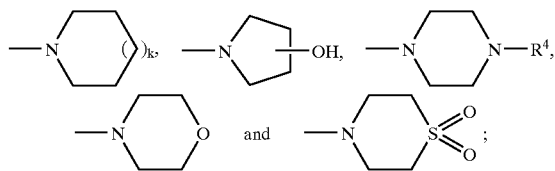

X is $N(R^4)$, O, S, S→O, $S(O_2)$, C(O) or $CH_2$;
Y is O, $CH_2$, C(O), N(H), $N(R^6)$ or S;
k is 0, 1 or 2;
m is 0, 1 or 2;
n is 0 or 2; and
wherein each of said alkyl, alkylene, heteroalkylene, aryl, aralkyl, alkoxy, arylyoxy, aryloxyalkyl, hydroxyalkyl, alkoxyalkyl, heterocyclyl, heterocycloalkyl, heteroaryl, heteroaralkyl, cycloalkylalkyl, heterocyclyl and cycloalkyl can be unsubstituted or optionally substituted with one or more $R^7$ moieties which can be the same or different.

This invention is also directed to pharmaceutical compositions for the treatment of metabolic disorders such as obesity, and eating disorders such as hyperphagia. In one aspect, this invention is also directed to pharmaceutical compositions for the treatment of obesity which comprise an obesity treating amount of a compound of formula I, or a pharmaceutically acceptable salt or solvate of said compound and a pharmaceutically acceptable carrier.

DETAILED DESCRIPTION

The present invention relates to compounds that are represented by structural formula I, or a pharmaceutically acceptable salt or solvate, wherein the various moieties are as described above.

The compounds of formula I can be administered as racemic mixtures or enantiomerically pure compounds.

A preferred group of compounds are compounds of formula Ia formula Ia

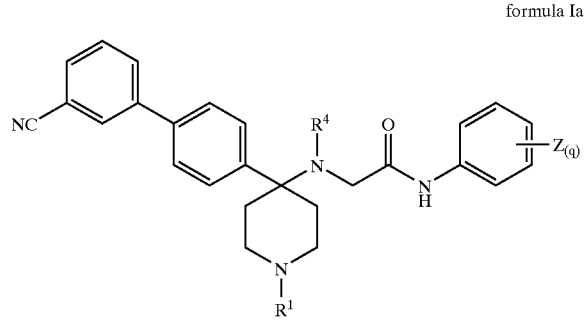

or a pharmaceutically acceptable salt or solvate of said compound, wherein:

q is 1 or 2;
$R^1$ is H, alkyl or cycloalkyl;
$R^4$ is H or alkyl; and
Z is 1 or 2 substituents which can be the same or different and independently selected from the group consisting of halogen, $CF_3$ and $OCF_3$.

Another preferred embodiment is a compound of formula Ib:

formula Ib

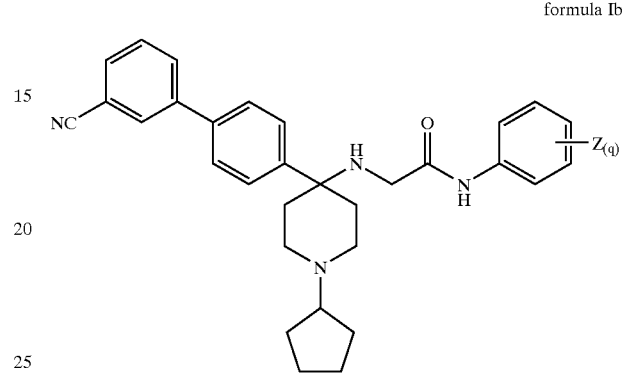

or a pharmaceutically acceptable salt or solvate of said compound, wherein:

q is 1 or 2;
Z is 1 or 2 substituents which can be the same or different and independently selected from the group consisting of halogen, $CF_3$ and $OCF_3$.

A further preferred embodiment is a compound of formula Ic:

formula Ic

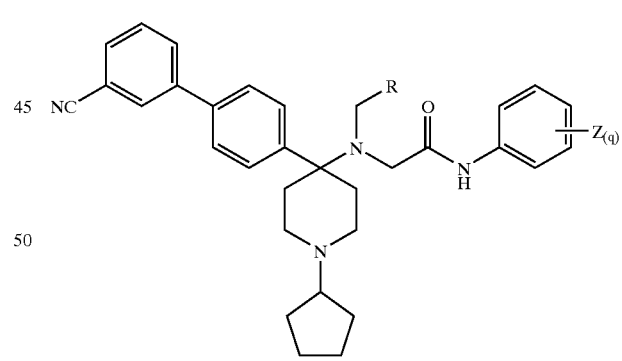

or a pharmaceutically acceptable salt or solvate of said compound, wherein:

q is 1 or 2;
R is H, alkyl or cycloalkyl; and
Z is 1 or 2 substituents which can be the same or different and independently selected from the group consisting of halogen, $CF_3$ and $OCF_3$.

A further preferred embodiment is a compound of formula Id:

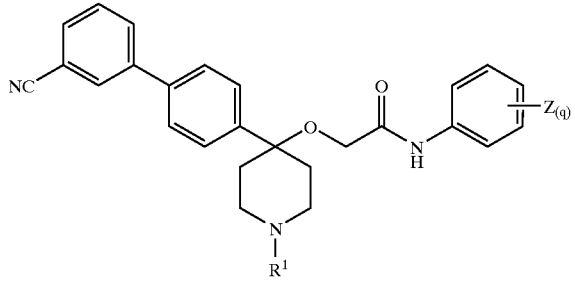

formula Id or a pharmaceutically acceptable salt or solvate of said compound, wherein:

q is 1 or 2;

$R^1$ is independently selected from the group consisting of H, alkyl and cycloalkyl; and Z is 1 or 2 substituents which can be the same or different and independently selected from the group consisting of halogen, $CF_3$ and $OCF_3$.

A further preferred embodiment is a compound of formula Ie:

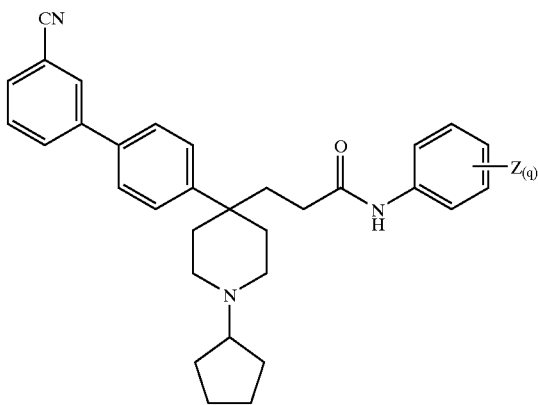

formula Ie or a pharmaceutically acceptable salt or solvate of said compound, wherein:

q is 1 or 2;

Z is 1 or 2 substituents which can be the same or different and independently selected from the group consisting of Cl, $CF_3$ and F.

A further preferred embodiment is a compound of formula If

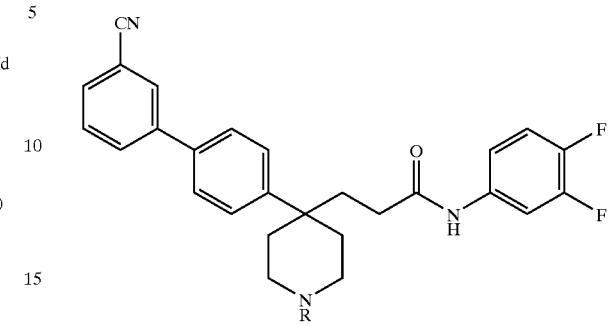

formula If or a pharmaceutically acceptable salt or solvate of said compound, wherein R is selected from the group consisting of $CH_3C(O)$, $CH_3S(O_2)$, $CH_3CH_2OC(O)$, $(CH_3CH_2)_2NC(O)$, $(CH_3)_2NS(O_2)$, $CH_3CH_2NHS(O_2)$ and cyclopropylmethyl.

A set of preferred compounds are listed below in Table 1.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "alkylamino" etc.

As used above, and throughout the specification, the following terms, unless otherwise indicated, shall be understood to have the following meanings:

"Patient" includes both human and other animals.

"Mammal" means humans and other mammalian animals.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, —cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halo, alkyl, aryl, —cycloalkyl, cyano, and alkoxy. Non-limiting examples of suitable alkenyl groups include ethenyl, propenyl, n-butenyl, and 3-methylbut-2-enyl.

"Alkynyl" means an aliphatic hydrocarbon group comprising at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means an alkynyl group having about 2 to about 6 carbon atoms in the chain, which may be straight or branched. Non-limiting examples of suitable alkynyl groups include ethynyl, propynyl and 2-butynyl. The term "substituted alkynyl" means that the alkynyl group may be substituted by one or more substituents which may be the same or different, each substituent being independently selected from the group consisting of alkyl, aryl and —cycloalkyl.

"Alkylene" means an alkanediyl group commonly having free valencies on two carbon atoms. Non-limiting examples include methylene, ethylene, propylene and the like. The term "substituted alkylene" means that the alkylene group may be substituted by one or more substituents which may be the same or different, each substituent being independently selected from the group consisting of halo, alkyl, aryl, —cycloalkyl, cyano, hydroxy, alkoxy, alkylthio, amino, —NH(alkyl), —NH(cycloalkyl), —N(alkyl)$_2$, carboxy and —C(O)O—alkyl.

"Aryl" means an aromatic monocyclic or multicyclic ring system comprising about 6 to about 14 carbon atoms, preferably about 6 to about 10 carbon atoms. The aryl group can be unsubstituted or substituted on the ring with one or more substituents which may be the same or different, each being independently selected from the group consisting of alkyl, aryl, —OCF$_3$, —OCOalkyl , —OCOaryl, —CF$_3$, heteroaryl, aralkyl, alkylaryl, heteroaralkyl, alkylheteroaryl, hydroxy, hydroxyalkyl, alkoxy, aryloxy, aralkoxy, acyl, aroyl, halo, haloalkyl, haloalkoxy, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, —cycloalkyl and heterocyclyl. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Arylene" means a bivalent group derived from an aromatic hydrocarbon by removal of a hydrogen atom from two ring carbon atoms. Non-limiting examples include phenylene and the like.

"Alkylenedioxy" means a combination of one or more carbon atoms and one or more oxygen atoms such as the following non-limiting examples that include methylenedioxy, ethylenedioxy, and the like.

"Heteroalkyl" means an alkyl group comprising about 5 to about 14 carbon atoms, preferably about 5 to about 10 carbon atoms, in which one or more of the carbon atoms is an element other than carbon, for example nitrogen, oxygen or sulfur, alone or in combination. Preferred heteroaryls contain about 5 to about 6 carbon atoms.

"Heteroaryl" means an aromatic monocyclic or multicyclic ring system (fused as well as connected by bond) comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, —cycloalkyl, cycloalkenyl and heterocyclyl. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, imidazolyl, and the like.

"Heteroalkylene" means a difunctional group obtained by removal of a hydrogen atom from an heteroalkyl group that is defined above.

"Heteroarylene" means a bivalent group derived from a heterocyclic aromatic compound by removal of a hydrogen atom from two ring carbon atoms such as, for example, the bivalent group derived from pyridine, pyrrole and the like.

"Aralkyl" means an aryl-alkyl- group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl. The term "substituted aralkyl" means that the aralkyl group may be substituted by one or more substituents which may be the same or different, each substituent being independently selected from the group consisting of halo, alkyl, aryl, —cycloalkyl, cyano, hydroxy, alkoxy, alkylthio, amino, —NH(alkyl), —NH(cycloalkyl), —N(alkyl)$_2$, carboxy and —C(O)O-alkyl.

"Alkylaryl" means an alkyl-aryl- group in which the alkyl and aryl are as previously described. Preferred alkylaryls comprise a lower alkyl group. Non-limiting example of a suitable alkylaryl groups is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, tetrahydronapthalenyl, indanyl, norbornyl, adamantyl and the like.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl and heterocyclyl. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, tetrahydrothiophenyl, morpholinyl and the like.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl. The "heteroaralkyl" can be optionally substituted on the ring by replacing an available hydrogen on the ring by one or more substituents which may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, —cycloalkyl, cycloalkenyl and heterocyclyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Alkoxyalkyl" means an alkoxy-alkyl- group in which alkyl and alkoxy are as previously defined. Non-limiting examples of suitable alkoxyalkyl groups include methoxymethyl, ethoxymethyl, methoxyethyl and ethoxyethyl.

"Aryloxyalkyl" means aryloxy-alkyl- group in which alkyl and aryloxy are as previously defined. Non-limiting examples of suitable aryloxyalkyl groups include phenyloxymethyl, phenyloxymethyl and benzyloxymethyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl—C(O)—, alkenyl—C(O)—, alkynyl—C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Alkoxy" means an alkyl-O- group in which the alkyl group is as previously described. Non-limiting examples of suitable alkoxy groups include methoxy, ethoxy, n-propoxy and isopropoxy. The alkyl group is linked to an adjacent moiety through the ether oxygen. The term "substituted alkoxy" means that the alkyl portion of the alkoxy group may be substituted by one or more substituents which may be the same or different, each substituent being independently selected from the group consisting of halo, alkyl, aryl, —cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl, n-butyl, and t-butyl.

"Aryloxy" means an aryl-O- group in which the aryl group is as previously described. Non-limiting examples of suitable aryloxy groups include phenoxy and naphthoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Cycloalkylalkyl" means a cycloalkylalkyl group in which the cycloalkyl and alkyl groups are as previously described. The bond to the parent moiety is through the alkyl group.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkoxy group defined earlier linked to an adjacent moiety through a carbonyl. Non-limiting examples of alkoxycarbonyl groups include —C(O)—$CH_3$, —C(O)—$CH_2CH_3$ and the like.

"Aralkoxycarbonyl" means an aralkyl—O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S($O_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties.

As used herein, the term "composition" is intended to encompass a product comprising the specified ingredients in the specified amounts, as well as any product which results, directly or indirectly, from combination of the specified ingredients in the specified amounts.

Solvates of the compounds of the invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound of the present invention effective to treat a mammal (e.g., human) having a disease or condition mediated by MCH, and thus producing the desired therapeutic effect.

The compound of formula I forms salts which are also within the scope of this invention. Reference to a compound of formula I, herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" and the like, is intended to equally apply to the salt and solvate of enantiomers, stereoisomers, rotamers, tautomers or racemates of the inventive compounds.

When any variable (e.g., aryl, heterocycle, $R^2$, etc.) occurs more than one time in any constituent or in formula I, its definition on each occurrence is independent of its definition at every other occurrence. Also, combinations of substituents and/or variables are permissible only if such combinations result in stable compounds.

As a general note to all the Tables that are attached hereto as well as to the Description, Examples and Schemes in this application, any open-ended nitrogen atom with unfulfilled valence in the chemical structures herein refers to NH, or in the case of a terminal nitrogen, —$NH_2$. Similarly, any open-ended oxygen atom with unfulfilled valence in the chemical structures herein refers to —OH and any open-ended carbon atom with unfilled valence is appropriately filled with —H.

Compounds of formula I can be highly selective, high affinity Melanin Concentrating Hormone (MCH) receptor antagonists useful for the treatment of obesity.

Another aspect of this invention is a method of treating a mammal (e.g., human) having a disease or condition mediated by MCH by administering a therapeutically effective amount of at least one compound of formula I, or a pharmaceutically acceptable salt or solvate of said compound to the mammal.

A preferred dosage is about 0.001 to 100 mg/kg of body weight/day of the compound of formula I. An especially preferred dosage is about 0.01 to 25 mg/kg of body weight/day of a compound of formula I, or a pharmaceutically acceptable salt or solvate of said compound.

Another aspect of this invention is directed to a method of treating obesity comprising administering to a mammal in need of such treatment a therapeutically effective amount of at least one compound of formula I, or a pharmaceutically acceptable salt or solvate of said compound.

Another aspect of this invention is directed to a method for treating eating and metabolic disorders such as bulimia and anorexia comprising administering to a mammal a therapeutically effective amount of at least one compound of formula I, or a pharmaceutically acceptable salt or solvate of said compound.

Another aspect of this invention is directed to a method for treating hyperlipidemia comprising administering to a mammal a therapeutically effective amount of at least one compound of formula I, or a pharmaceutically acceptable salt or solvate of said compound.

Another aspect of this invention is directed to a method for treating cellulite and fat accumulation comprising administering to a mammal a therapeutically effective amount of at least one compound of formula I, or a pharmaceutically acceptable salt or solvate of said compound.

Another aspect of this invention is directed to a method for treating type II diabetes comprising administering to a mammal a therapeutically effective amount of at least one compound of formula I, or a pharmaceutically acceptable salt or solvate of said compound.

In addition to the "direct" effect of the compounds of this invention on the MCH subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

Another aspect of this invention is directed to a method for treating mental disorders such as major depression, manic depression, anxiety, schizophrenia and sleep disorders, comprising administering to a mammal a therapeutically effective amount of at least one compound of formula I, or a pharmaceutically acceptable salt or solvate of said compound.

This invention is also directed to pharmaceutical compositions which comprise at least one compound of formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of formula I, or a pharmaceutically acceptable salt or solvate of said compound and at least one pharmaceutically acceptable carrier.

Compounds of formula I, can be produced by processes known to those skilled in the art using either solution phase or solid phase synthesis as shown in the following reaction schemes, in the preparations and examples below.

A preferred group of compounds are those listed below in Table 1. or a pharmaceutically acceptable salt or solvate of said compound.

Another aspect of this invention is a method of treating a mammal (e.g., human) having a disease or condition mediated by MCH by administering a therapeutically effective amount of a compound of formula I, or a pharmaceutically acceptable salt of said compound to the mammal.

A preferred dosage is about 0.001 to 100 mg/kg/day of the formula I compound. An especially preferred dosage is about 0.01 to 25 mg/kg/day of a compound of formula I, or a pharmaceutically acceptable salt of said compound.

Another aspect of this invention is directed to a method of treating obesity comprising administering to a mammal in need of such treatment a therapeutically effective amount of a compound of formula I or a pharmaceutically acceptable salt of said compound.

Another aspect of this invention is directed to a method for treating metabolic disorders such as obesity and eating disorders such as bulimia and anorexia comprising administering to a mammal a therapeutically effective amount of a compound of formula I, or a pharmaceutically acceptable salt of said compound.

Another aspect of this invention is directed to a method for treating hyperlipidemia comprising administering to a mammal a therapeutically effective amount of a compound of formula I, or a pharmaceutically acceptable salt of said compound.

Another aspect of this invention is directed to a method for treating cellulite and fat accumulation comprising administering to a mammal a therapeutically effective amount of a compound of formula I, or a pharmaceutically acceptable salt of said compound.

Another aspect of this invention is directed to a method for treating type II diabetes comprising administering to a mammal a therapeutically effective amount of a compound of formula I, or a pharmaceutically acceptable salt of said compound.

In addition to the "direct" effect of the compounds of this invention on the MCH subtype, there are diseases and conditions that will benefit from the weight loss such as insulin resistance, impaired glucose tolerance, Type II Diabetes, hypertension, hyperlipidemia, cardiovascular disease, gall stones, certain cancers, and sleep apnea.

This invention is also directed to pharmaceutical compositions which comprise an amount of a compound of formula I, or a pharmaceutically acceptable salt of said compound and a pharmaceutically acceptable carrier therefor.

This invention is also directed to pharmaceutical compositions for the treatment of obesity which comprise an obesity treating amount of a compound of formula, I, a or a pharmaceutically acceptable salt of said compound and a pharmaceutically acceptable carrier therefor.

Compounds of formula I can be produced by processes known to those skilled in the art using either solution phase or solid phase synthesis as shown in the following reaction schemes, in the preparations and examples below.

Compounds of formulas Ia, Ib and Ic, are prepared according to the method described in Scheme 1;

These novel compounds are potent MCH antagonists and also selective against other receptors, such as $M_2$ receptor, h-HT transporter.

All stereoisomers and tautomeric forms of these compounds are contemplated. Compounds of formulas Ia, Ib and Ic can be prepared from 4-(4-bromophenyl) piperidinol (Scheme 1).

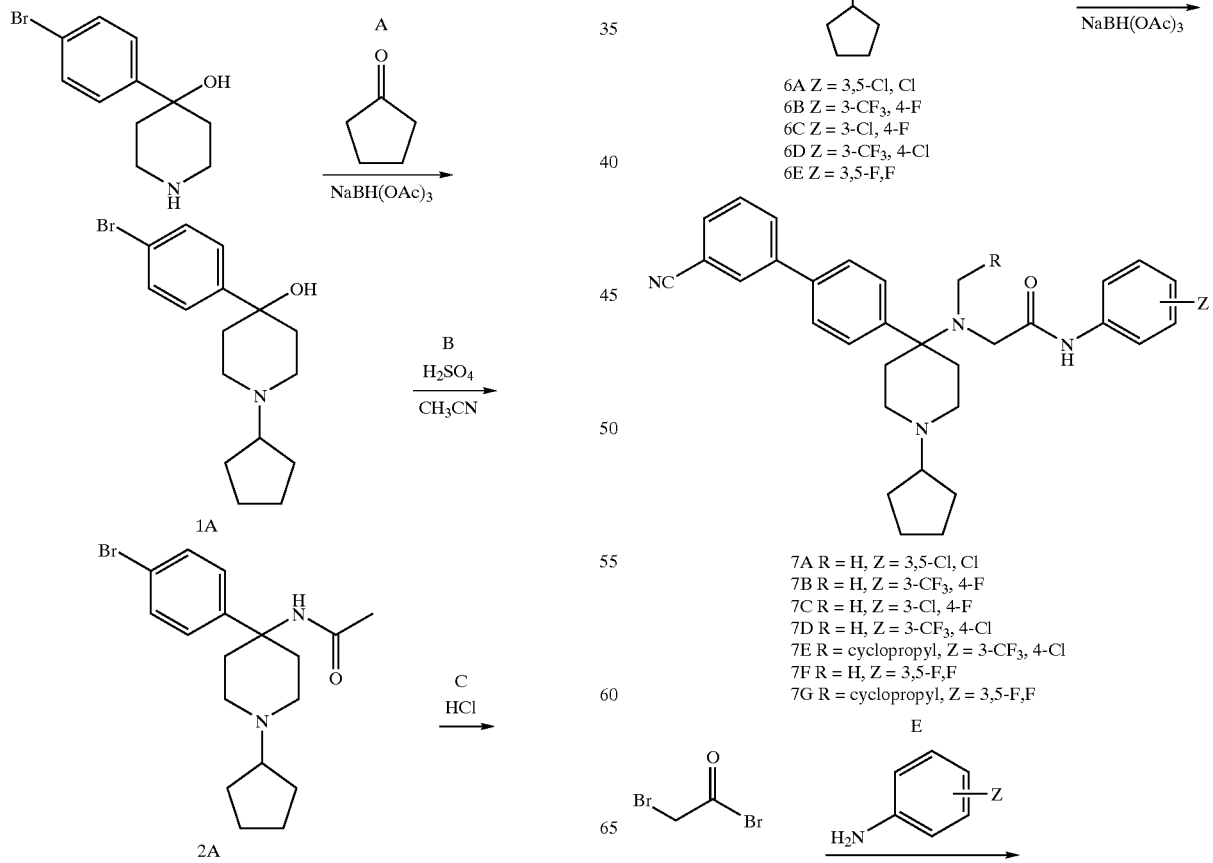

-continued
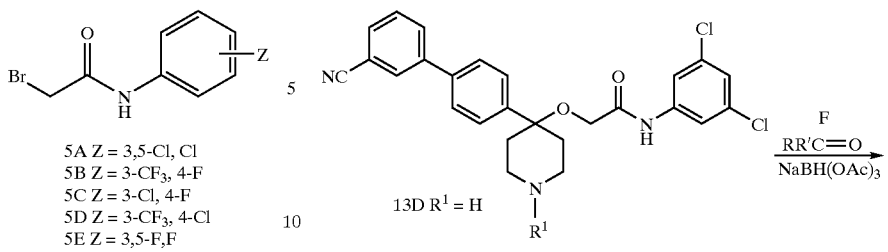
5A Z = 3,5-Cl, Cl
5B Z = 3-CF$_3$, 4-F
5C Z = 3-Cl, 4-F
5D Z = 3-CF$_3$, 4-Cl
5E Z = 3,5-F,F
Compounds of formula Id can be prepared from 4-(4-bromophenyl) piperidinol (Scheme 2).
A number of compounds where X is an alkylene, are synthesized as seen in schemes 3 and 4.
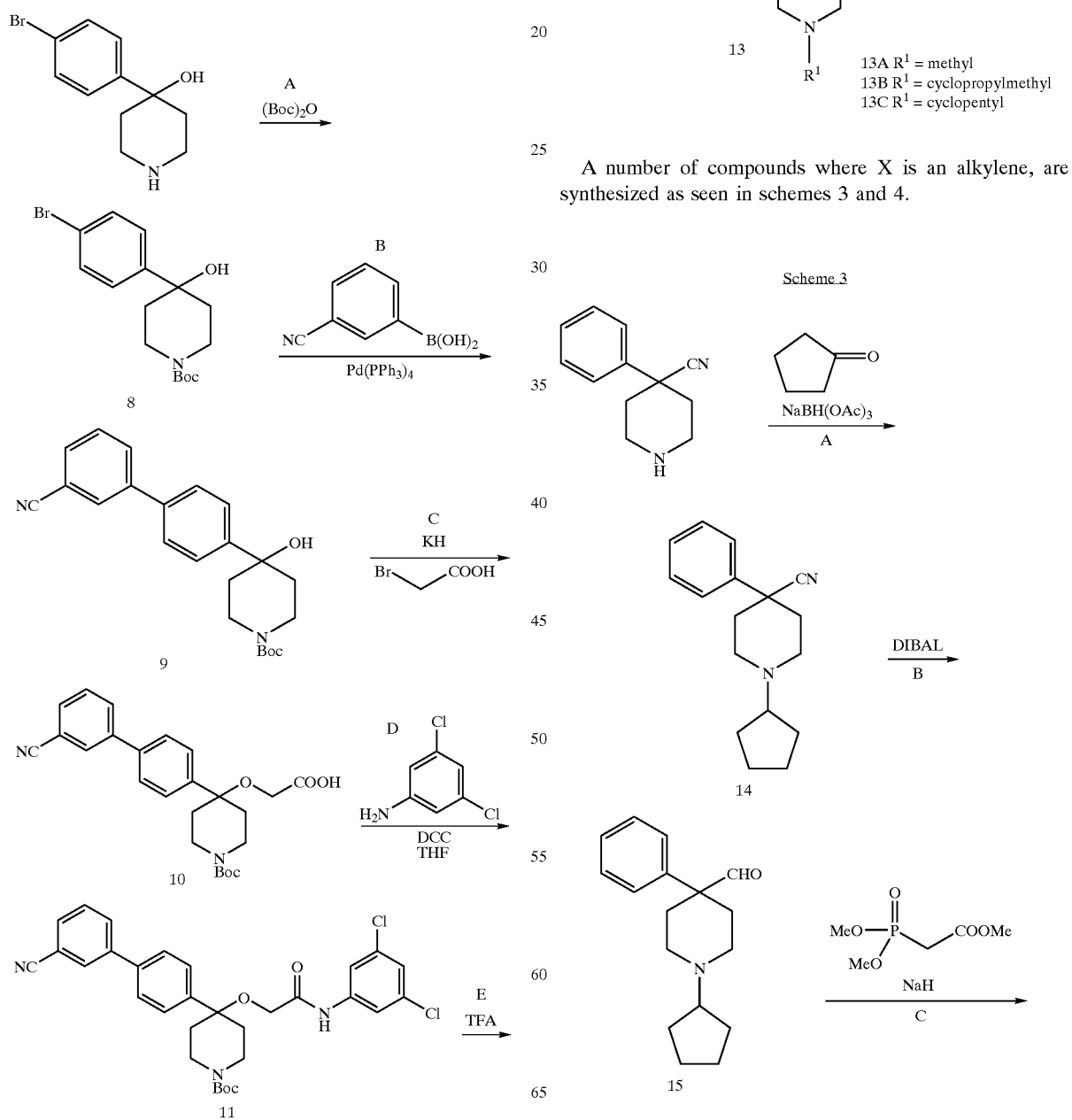
13A R$^1$ = methyl
13B R$^1$ = cyclopropylmethyl
13C R$^1$ = cyclopentyl

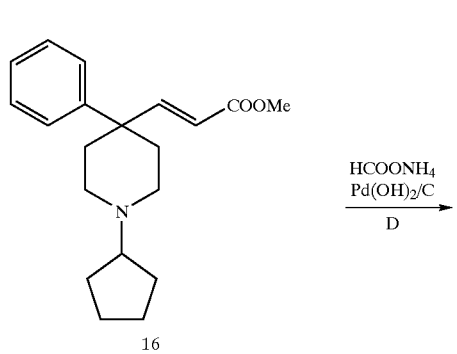
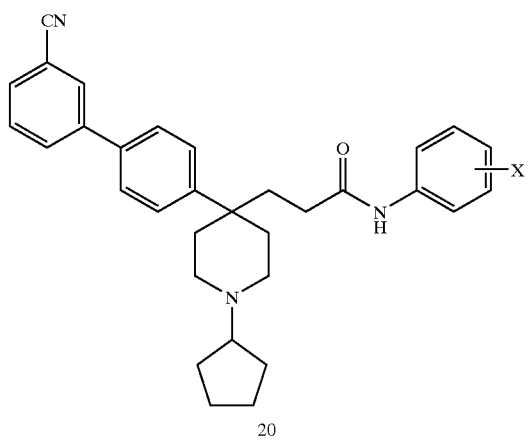
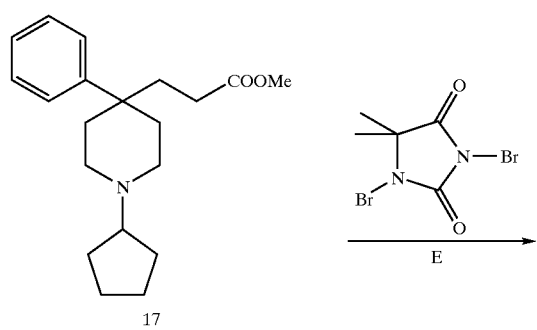
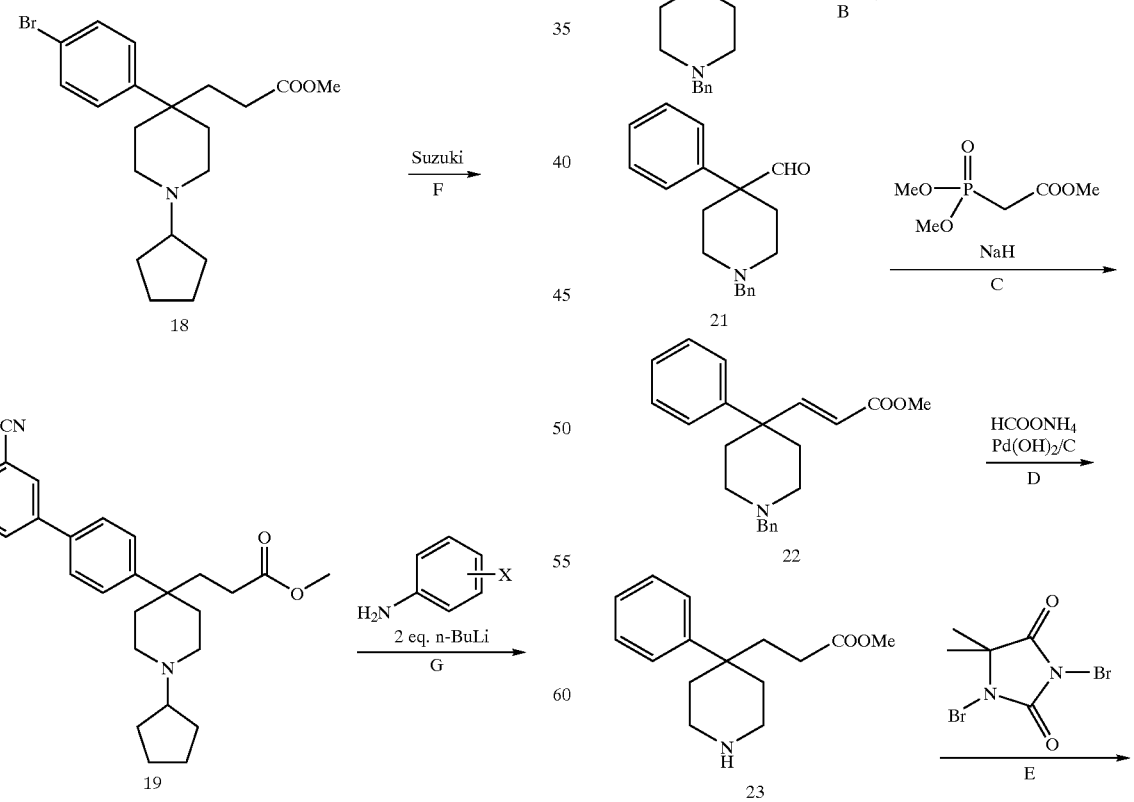
Scheme 4

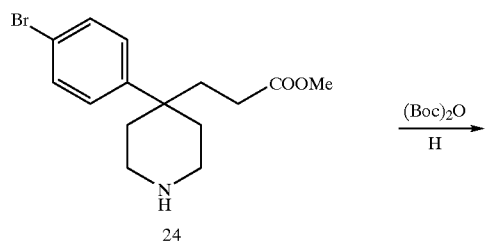

24

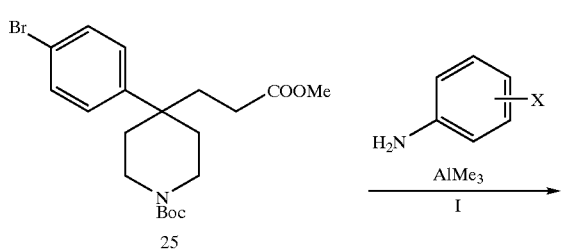

25

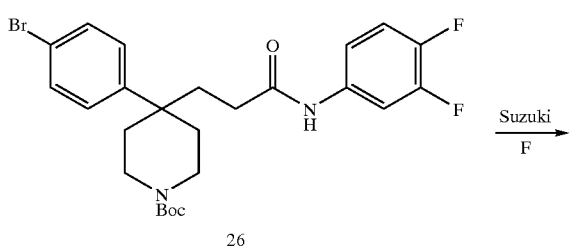

26

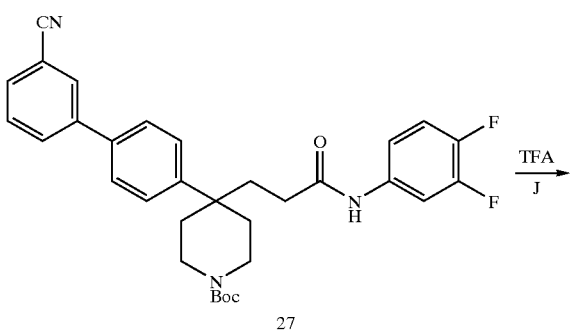

27

28

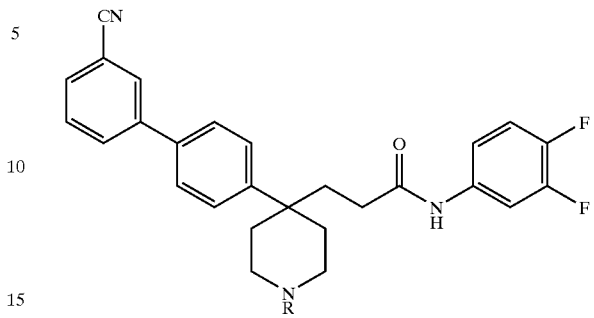

29A R = MeCO
29B R = MeSO$_2$
29C R = EtOCO
29D R = Et$_2$NCO
29E R = Me$_2$NSO$_2$
29F R = EtNHSO$_2$
29G R = cyclopropylmethyl Other related routes/chemistry are also contemplated.

Yet another aspect of this invention are combinations of at least one compound of formula I, or a pharmaceutically acceptable salt or solvate of said compound and at least one compound from the compounds as illustrated below.

Accordingly, another aspect of this invention is a method for treating obesity comprising administering to a mammal (e.g., a female or male human)

a. an amount of a first compound, said first compound being a compound of formula I, or a pharmaceutically acceptable salt or solvate of said compound; and b. an amount of a second compound, said second compound being an antiobesity and/or anorectic agent such as a β$_3$ agonist, a thyromimetic agent, an anoretic agent, or an NPY antagonist wherein the amounts of the first and second compounds result in a therapeutic effect.

This invention is also directed to a pharmaceutical combination composition comprising: a therapeutically effective amount of a composition comprising at least one first compound, said first compound being a compound of formula I, or a pharmaceutically acceptable salt or solvate of said compound a second compound, said second compound being an antiobesity and/or anorectic agent such as a β$_3$ agonist, a thyromimetic agent, an anoretic, or an NPY antagonist; and/or optionally a pharmaceutical carrier, vehicle or diluent.

Another aspect of this invention is a kit comprising:

a. an amount of a compound of formula I, or a pharmaceutically acceptable salt or solvate of said compound and a pharmaceutically acceptable carrier, vehicle or diluent in a first unit dosage form;

b. an amount of an antiobesity and/or anorectic agent such as a β$_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human)

a. an amount of a first compound, said first compound being a compound of formula I, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of formula I, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of formula I, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

This invention is also directed to pharmaceutical compositions for the treatment of metabolic disorders such as obesity, and eating disorders such as hyperphagia.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:

Thin layer chromatography (TLC);
ethyl acetate (AcOEt or EtOAc);
di-t-butyl carbonate (BOC$_2$O);
trifluoroacetate (TFA);
titanium tetraisoproposice (Ti(O-iPr)$_4$;
N,N'-diisopropylethylamine (iPr$_2$NEt);
triethylamine (Et$_3$N or TEA);
butoxycarbonyl (n-Boc or Boc);
1,2-dimethoxyethane (DME);
1,2-dichloroethane (DCE);
acetic acid (AcOH);
trifluoroacetic anhydride (TFAA);
1-hydroxybenzotriazole (HOBt);
1-(3-dimethylaminopropyl)-3-ethyl carbodiimide hydrochloride (EDCl);
m-chloroperbenzoic acid (MCPBA);
triethylamine (Et$_3$N);
4-dimethylaminopyridine (DMAP)
tert-butoxycarbonyl (Boc);
triethylamine (TEA);
nuclear magnetic resonance spectroscopy (H NMR);
liquid chromatography mass spectrometry (LCMS);
high resolution mass spectrometry (HRMS);
hexane (hex);
milliliters (mL);
millimoles (mmol);
microliters (μl);
grams (g);
milligrams (mg);
room temperature (ambient) about 25° C. (rt).

EXAMPLES

Compounds useful in this invention are exemplified by the following preparative examples, which should not be construed to limit the scope of the invention. Alternative mechanistic pathways and analogous structures within the scope of the invention would be apparent to those skilled in the art.

Starting materials are prepared by known methods and/or methods described in the Preparations. The following examples illustrate the preparation of some of the compounds of the invention and are not to be construed as limiting the invention disclosed herein.

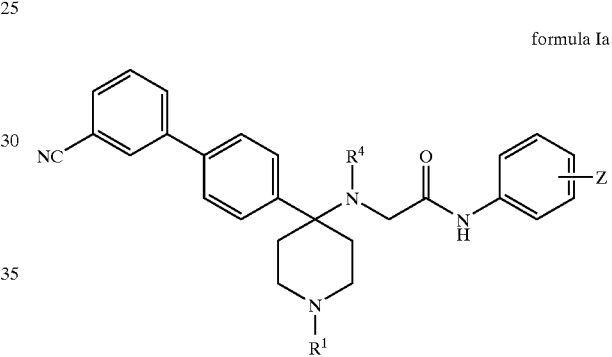

formula Ia

Compounds 6A–6E (formula Ib) and 7A–7G (formula Ic) are prepared according to the Experimental Procedures described below.

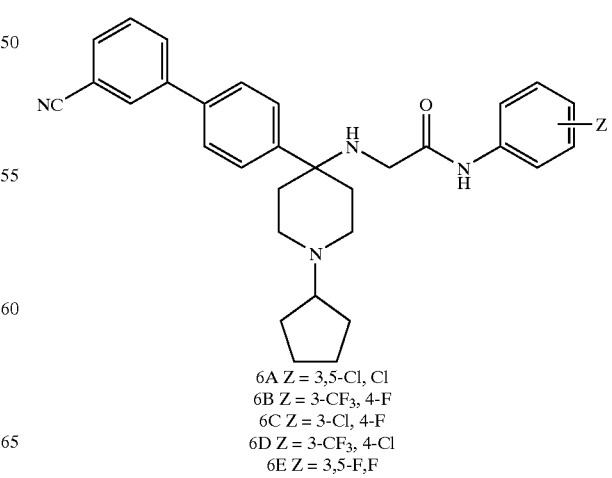

formula Ib

6A Z = 3,5-Cl, Cl
6B Z = 3-CF$_3$, 4-F
6C Z = 3-Cl, 4-F
6D Z = 3-CF$_3$, 4-Cl
6E Z = 3,5-F,F

-continued formula Ic

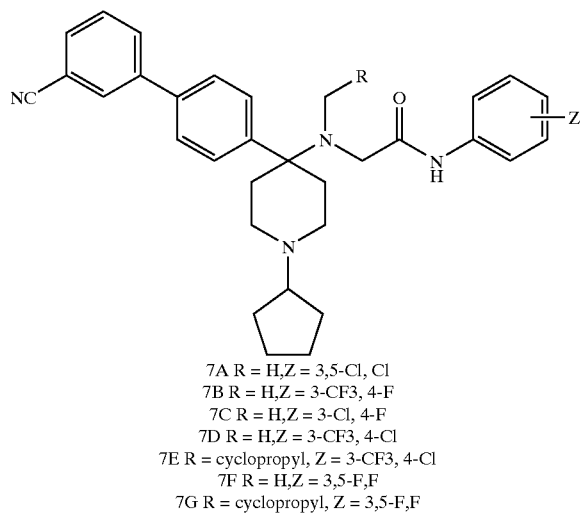

7A R = H, Z = 3,5-Cl, Cl
7B R = H, Z = 3-CF3, 4-F
7C R = H, Z = 3-Cl, 4-F
7D R = H, Z = 3-CF3, 4-Cl
7E R = cyclopropyl, Z = 3-CF3, 4-Cl
7F R = H, Z = 3,5-F,F
7G R = cyclopropyl, Z = 3,5-F,F Procedure A:

To a stirred suspension of 2.61 g (10 mmol) of 4-(4-bromophenyl)-4-piperidinol, 0.925 g (11 mmol) of cyclopentanone and 0.6 mL (10 mmol) of acetic acid in 30 mL of dichloromethane was added 2.9 g (13 mmol) of NaBH(OAc)$_3$ in portions at room temperature. The stirring was continued for 65 h. It was quenched with 120 mL of saturated NaHCO$_3$ solution, then extracted with dichloromethane (150 mL) three times. The combined organic extracts were washed with brine (80 mL) and concentrated. The residue was chromatographed on silica gel eluting with 1 to 3% MeOH in CH$_2$Cl$_2$ to give 2.36 g of compound 1A. Calcd m/z for $C_{16}H_{23}BrNO$=324; found m/z=324.

Procedure B:

To a stirred suspension of 0.32 g (1.0 mmol) of compound 1A in 1 mL of acetonitrile was added 0.3 mL (4.8 mmol) of concentrated H$_2$SO$_4$ at 0° C. The mixture was warmed to room temperature and stirred for 40 h. It was quenched with 40 mL of saturated NaHCO$_3$, extracted with ethyl acetate (40 mL) three times. The combined organic extracts were washed with 30 mL of brine and concentrated. The residue was chromatographed on silica gel eluting with 1 to 3% MeOH in CH$_2$Cl$_2$ plus 1% NH$_4$OH to give 0.33 g of compound 2A. Calcd m/z for $C_{18}H_{26}BrN_2O$=365; found m/z=365.

Procedure C:

A suspension of 0.3 g (0.82 mmol) of compound 2A in 10 mL of 2N HCl was refluxed for 110 h. It was basified with 40 mL of diluted NH$_4$OH solution, then extracted with CH$_2$Cl$_2$ (40 mL) three times. The combined organic extracts were washed with 30 mL of brine, concentrated. The residue was chromatographed on silica gel eluting with 1 to 3% MeOH in CH$_2$Cl$_2$ plus 1% NH$_4$OH to give compound 0.2 g of 3A. Calcd m/z for $C_{16}H_{24}BrN_2$=323; found m/z=323.

Procedure D:

A mixture of 1.46 g (4 mmol) of compound 3A, 0.88 g (6.0 mmol) of 3-cyanophenylboronic acid, 0.46 g (0.4 mmol) of Pd(PPh$_3$)$_4$ in 5 mL of 2N Na$_2$CO$_3$ and 20 mL of toluene-MeOH (1:1) solution was refluxed under N$_2$ atmosphere for 18 hrs. It was cooled to room temperature and passed through a pad of celite and washed with ethyl acetate. The filtrate was concentrated, the residue was chromatographed on silica gel eluting with 1 to 3% MeOH in CH$_2$Cl$_2$ plus 1% NH$_4$OH to give 1.32 g of compound 4A. Calcd m/z for $C_{23}H_{28}N_3$ =346; found m/z=346.

Procedure E:

To a stirred solution of 1.62 g (10 mmol) of 3,5-dichloroaniline and 2 g of triethylamine in 20 mL of CH$_2$Cl$_2$ was added 2-bromoacetyl bromide at 0° C. The mixture was stirred at 0° C. for 2 hrs, diluted with 100 mL of ethyl actate. The solution was washed with 50 mL of diluted NaOH; the aqueous layer was extracted with 50 mL of ethyl acetate. The combined organic extracts were washed with 50 mL of brine, concentrated to give 2.95 g of compound 5A. 1H NMR (CDCl$_3$, 400 MHz) δ 8.15 (br, 1H), 7.51 (s, 2H), 7.16 (s, 1H), 4.02 (s, 2H).

Compounds 5B, 5C, 5D and 5E can be prepared analogously.

Procedure F:

A mixture of 0.17 g (0.5 mmol) of compound 4A, 0.85 g (0.3 mmol) of compound 5A and 0.083 g (0.6 mmol) of K$_2$CO$_3$ in 3 mL of CH$_3$CN was stirred at 60° C. for 16 hrs. It was diluted with 25 mL of H$_2$O and extracted with ethyl acetate (30 mL) three times. The combined organic extracts were washed with 25 mL of brine and concentrated. The residue was purified by preparative TLC eluting with 10% MeOH in CH$_2$Cl$_2$ plus 1% NH$_4$OH to give 0.089 g of compound 6A. Calcd m/z for $C_{31}H_{33}Cl_2N_4O$=548; found m/z=547.

The following compounds can be prepared analogously.

Compound 6B: calcd m/z for $C_{32}H_{33}F_4N_4O$=565; found m/z=565.

Compound 6C: calcd m/z for $C_{31}H_{33}ClFN_4O$=531; found m/z=531.

Compound 6D: calcd m/z for $C_{32}H_{33}ClF_3N_4O$=581; found m/z=581.

Compound 6E: calcd m/z for $C_{31}H_{33}F_2N_4O$=515; found m/z=515.

Procedure G:

A mixture of 0.023 g (0.004 mmol) of compound 6A, 0.01 mL of aqueous HCHO (37%) and NaBH(OAc)$_3$ in 2 mL of CH$_2$Cl$_2$ was stirred at room temperature for 90 h. Direct preparative TLC eluting with 10% MeOH in CH$_2$Cl$_2$ plus 1% NH$_4$OH gave 0.022 g of compound 7A. Calcd m/z for $C_{32}H_{35}Cl_2N_2O$=561; found m/z=561.

The following compounds can be prepared analogously.

Compound 7B: calcd m/z for $C_{33}H_{35}F_4N_4O$=579; found m/z=579.

Compound 7C: calcd m/z for $C_{32}H_{35}ClFN_4O$=545; found m/z=545.

Compound 7D: calcd m/z for $C_{33}H_{35}ClF_3N_4O$=595; found m/z=595.

Compound 7E: calcd m/z for $C_{36}H_{39}ClF_3N_4O$=635; found m/z=635.

Compound 7F: calcd m/z for $C_{32}H_{35}F_2N_4O$=529; found m/z=529.

Compound 7G: cacld m/z for $C_{35}H_{39}F_2N_4O$=569; found m/z=569.

Compounds 13A–13D (formula Id) are prepared according to the Experimental Procedures described below.

Formula Id

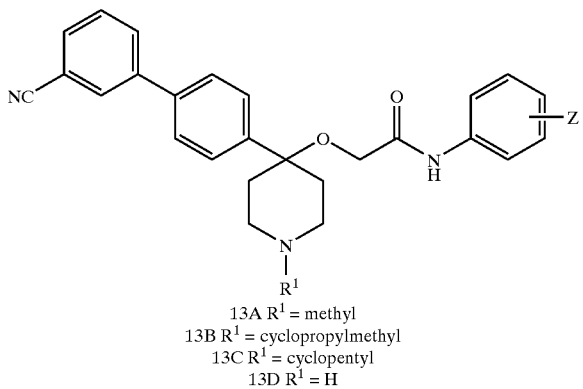

13A R$^1$ = methyl
13B R$^1$ = cyclopropylmethyl
13C R$^1$ = cyclopentyl
13D R$^1$ = H Procedure A:

To a stirred solution of 15.46 g (59 mmol) of 4-(4-bromophenyl)-4-piperidinol in 75 mL of methanol was added 15.65 g (71 mmol) of di-t-butyl dicarbonate in portions. The stirring was continued overnight. It was concentrated and partitioned between 25 mL of saturated NaHCO$_3$ and 50 mL of CH$_2$Cl$_2$. The organic layer was separated and the aqueous layer was extracted with CH$_2$Cl$_2$ (50 mL) three times. The combined organic extracts were washed with brine (25 mL) and concentrated. The residue was chromatographed on silica gel eluting with 10% EtOAc in Hexanes to give 20.8 g of compound 8. Calcd m/z for C$_{16}$H$_{23}$BrNO$_3$= 356; found m/z=356.

Procedure B:

To a stirred solution of 9.75 g (27 mmol) of compound 8 in 60 mL of toluene/water/ethanol (4:2:1) was added 4.91 g (32 mmol) of 3-cyanophenylboronic acid, 11.2 g (81 mmol) of potassium carbonate and 1.56 g (1.3 mmol) of tetrakistriphenylphosphine palladium. The mixture was heated to reflux and stirred overnight. It was filtered over a pad of celite, concentrated and partitioned between 20 mL of NaHCO$_3$ and 20 mL of CH$_2$Cl$_2$. The organic layer was separated and the aqueous layer was extracted with CH$_2$Cl$_2$ (20 mL) three times. The combined organic extracts were washed with 20 mL of brine and concentrated. The residue was chromatographed on silica gel eluting with 20 to 35% EtOAc in hexanes to give 5.7 g of compound 9. Calcd m/z for C$_{23}$H$_{27}$N$_2$O$_3$=379; found m/z=379.

Procedure C:

To a stirred solution of 15.1 g (132 mmol) of potassium hydride (35%) in 20 mL of THF was slowly added a solution of 8.3 g (22 mmol) of compound 9 in 50 mL of THF at 0° C. After stirring for 1 h, a solution of 6.3 g (44 mmol) of bromoacetic acid in 20 mL of THF was introduced over 30 minutes at 0° C. It was stirred and warmed to room temperature overnight and then quenched with 20 mL of water. It was concentrated, diluted with 25 mL of saturated NaHCO$_3$ and extracted with CH$_2$Cl$_2$ (5 mL) four times. The combined organic extracts were washed with 25 mL of brine and concentrated. The residue was chromatographed on silica gel eluting with 2 to 5% MeOH in CH$_2$Cl$_2$ plus 1% HOAc to give compound 8.7 g of 10. Calcd m/z for C$_{25}$H$_{28}$N$_2$O$_5$=437; found mz=437.

Procedure D:

A solution of 0.5 g (1.14 mmol) of compound 10, 0.36 g (1.7 mmol) of 1,3-dicyclohexyl carbodiimide, 0.23 g (1.4 mmol) of 3,5-dichloroaniline and 0.013 g of DMAP in 10 mL of THF was stirred at room temperature for 72 hrs. It was concentrated, diluted with 10 mL of saturated NaHCO$_3$ and extracted with CH$_2$Cl$_2$ (10 mL) five times. The combined organic layers were washed with 10 mL of brine and concentrated. The residue was chromatographed on silica gel eluting with 5 to 35% EtOAc in hexanes plus 1% NH$_4$OH to give 0.44 g of compound 11. Calcd m/z for C$_{31}$H$_{32}$Cl$_2$N$_3$O$_4$=580; found m/z=580.

Procedure E:

To a stirred solution of 0.44 g (0.75 mmol) of compound 11 in 2.5 mL of CH$_2$Cl$_2$ was added 2.5 mL of TFA at 0° C. The mixture was stirred at 0° C. for 30 minutes and concentrated. The residue was purified over silica gel eluting with 2 to 3% MeOH in CH$_2$Cl$_2$ plus 1% NH$_4$OH to give 0.31 g of compound 13D. Calcd m/z for C$_{26}$H$_{24}$Cl$_2$N$_3$O$_2$=480; found m/z=480.

Procedure F:

A solution of 0.035 g (0.073 mmol) of compound 13D, 0.012 g (0.15 mmol) of aqueous HCHO (37%) and 0.049 g (0.22 mmol) of NaBH(OAc)$_3$ in 2 mL of CH$_2$Cl$_2$ was stirred at room temperature overnight. The mixture was purified by preparative TLC eluting with 5% MeOH in CH$_2$Cl$_2$ plus 1% NH$_4$OH to give 0.03 g of compound 13A. Calcd m/z for C$_{27}$H$_{26}$Cl$_2$N$_3$O$_2$=494; found m/z=494.

The following compounds can be prepared analogously.

Compound 13B: calcd m/z for C$_{30}$H$_{30}$Cl$_2$N$_3$O$_2$=534; found m/z=534.

Compound 13C: calcd m/z for C$_{31}$H$_{32}$Cl$_2$N$_3$O$_2$=548; found m/z=548.

The compounds of formula I display pharmacological activity in a test procedure designed to demonstrate MCH receptor antagonist activity. The compounds are non-toxic at pharmaceutically therapeutic doses.

Experimental Procedures—C-linked Series of Schemes 3 and 4

Procedure A:

To a suspension of 20.20 g (91 mmol) of 4-cyano-4-phenylpiperidine hydrochloride and 8.94 mL (100 mmol) of cyclopentanone in 125 mL of CH$_2$Cl$_2$ was added 5.25 mL (91 mmol) of acetic acid, 26.8 g (120 mmol) of NaBH(OAc)$_3$. The mixture was stirred at room temperature for two days. It was diluted with 150 mL of saturated NaHCO$_3$, and extracted with CH$_2$Cl$_2$. The combined organic extracts were washed with brine and concentrated. The residue was chromatographed on silica gel eluting with 1 to 3% MeOH in CH$_2$Cl$_2$ to give 20.6 g of compound 14. Calcd m/z for C$_{17}$H$_{23}$N$_2$=255.19; found m/z=255.1.

Compound 29G can be prepared analogously. Calcd m/z for C$_{31}$H$_{32}$F$_2$N$_3$O=500.2; found m/z=500.1

Procedure B:

To a stirred solution of 8.0 g (29 mmol) of 1-benzyl-4-cyano4-phenylpiperidine in 100 mL of CH$_2$Cl$_2$ was added 38 mL (38 mmol) of DIBAL in toluene. The mixture was warmed to room temperature overnight. Additional 5.5 mL (5.5 mL) of DIBAL was added at room temperature. After 15 min, the solution was cooled to −78° C. It was quenched with 15 mL of MeOH, and warmed to room temperature. It was filtered over a pad of celite, and the filtrate was concentrated. The residue was chromatographed on silica gel eluting with 1 to 3% MeOH in CH$_2$Cl$_2$ to give 3.92 g of compound 21. Calcd m/z for C$_{19}$H$_{22}$NO=280.17; found m/z=280.3.

Compound 15 can be prepared analogously. Calcd m/z for C$_{17}$H$_{24}$NO=258.19; found m/z=258.1.

Procedure C:

To a suspension of 1.8 g (45 mmol) of NaH (60%) in 250 mL of THF was added 7.28 g (40 mmol) of trimethyl phosphonoacetate at 0° C. After stirring for 50 min, a solution of 8.4 g (30 mmol) of compound 21 in 40 mL of THF was introduced at 0° C. It was stirred at room temperature for 18 h and then concentrated. The residue was dissolved in 150 mL of H$_2$O and extracted with four portions of 150 mL of ethyl acetate. The combined organic extracts were washed with 60 mL of brine and concentrated. The residue was chromatographed on silica gel eluting with 1 to 3% MeOH in CH$_2$Cl$_2$ plus 1% NH$_4$OH to give compound 8.7 g of 22. Calcd m/z for C$_{22}$H$_{26}$NO$_2$=336.2; found m/z=336.1.

Compound 16 can be prepared analogously. Calcd m/z for C$_{20}$H$_{28}$NO$_2$=314.2; found m/z=314.1.

Procedure D:

To a solution of 0.67 g (2 mmol) of compound 22, 3.0 g (47 mmol) of HCOONH$_4$ in 30 mL of MeOH was added 0.2 g of Pd(OH)$_2$/C. The mixture was stirred at 60° C. for 2 h. It was filtered, and the filtrate was concentrated. The residue was dissolved in 50 mL of 1N NaOH, and extracted with four portions of 60 mL of ethyl acetate. The combined organic layers were washed with 50 mL of brine and concentrated. The residue was chromatographed on silica gel eluting with 1 to 4% MeOH in CH$_2$Cl$_2$ plus 1% NH$_4$OH to give 0.42 g of compound 23. Calcd m/z for C$_{15}$H$_{22}$NO$_2$=248.17; found m/z=248.3.

Compound 17 can be prepared analogously. Calcd m/z for C$_{20}$H$_{30}$NO$_2$=316.2; found m/z=316.3.

Procedure E:

To a solution of 5.4 g (21.8 mmol) of compound 23 in 50 mL of CH$_2$Cl$_2$ was added 7.5 g (78 mmol) of MeSO$_3$H at 0° C. After 10 min, 1,3-dibromo-5,5-dimethylhydantoin was added. The mixture was stirred at room temperature for 24 h, and quenched with 2 g of Na$_2$S$_2$O$_3$. It was diluted with 100 mL of CH$_2$Cl$_2$, and washed with 100 mL of 1N NaOH. The aqueous layer was extracted with two portions of 120 mL of CH$_2$Cl$_2$. The combined organic layers were washed with 80 mL of brine and concentrated. The residue was purified over silica gel eluting with 1 to 4% MeOH in CH$_2$Cl$_2$ plus 1% NH$_4$OH to give 3.82 g of compound 24. Calcd m/z for C$_{15}$H$_{21}$BrNO$_2$=326.1; found m/z=326.1.

Compound 18 can be prepared analogously. Calcd m/z for C$_{20}$H$_{29}$BrNO$_2$=394.1; found m/z=394.1.

Procedure F:

To a solution of 2.4 g (6.1 mmol) of compound 18, 1.5 g (9.3 mmol) of 3-cyanophenylboronic acid, and 0.67 g (0.6 mmol) of Pd(PPh$_3$)$_4$ in 30 mL of MeOH-toluene (1:1) was added 6 mL of 2N Na$_2$CO$_3$. The mixture was stirred under reflux for 18 h and concentrated. The residue was dissolved in 50 mL of saturated NaHCO$_3$, and extracted with three portions of 80 mL of ethyl acetate. The combined organic layers were washed with 50 mL of brine and concentrated. The residue was purified over silica gel eluting with 1 to 3% MeOH in CH$_2$Cl$_2$ plus 1% NH$_4$OH to give 1.42 g of compound 19. Calcd m/z for C$_{27}$H$_{33}$N$_2$O$_2$=417.3; found m/z=417.4.

Compound 27 can be prepared analogously. Calcd m/z for C$_{32}$H$_{34}$F$_2$N$_3$O$_3$=546.2; found m/z=546.1.

Procedure G:

To a solution of 0.05 g (0.12 mmol) of compound 19 in 2 mL of toluene was added 0.12 g (3 mmol) of NaH (60%). After stirring for 10 min, a solution of 0.04 g (0.2 mmol) of 4-Chloro-3-trifluoromethylaniline in 1 mL of toluene was added. The mixture was stirred under reflux for 4 h and cooled to room temperature. It was poured into 20 g of ice, and extracted with two portions of 30 mL of ethyl acetate. The combined organic layers were washed with 20 mL of brine and concentrated. The residue was purified by preparative TLC eluting with 10% MeOH in CH$_2$Cl$_2$ plus 1% NH$_4$OH to give 0.018 g of compound 20A. Calcd m/z for CHNO=; found m/z=580.3.

The following compounds can be prepared analogously.

Compound 20B: Calcd m/z for C$_{32}$H34Cl$_2$N$_3$O (M+1)$^+$=546.2; found m/z=546.1.

Compound 20C: Calcd m/z for C$_{32}$H34ClFN$_3$O (M+1)$^+$=530.2; found m/z=530.1.

Compound 20D: Calcd m/z for C$_{32}$H34F$_2$N$_3$O (M+1)$^+$=514.2; found m/z=514.1.

Compound 20E: Calcd m/z for C$_{32}$H34Cl$_2$N$_3$O (M+1)+=546.2; found m/z=546.1

Compound 20F: Calcd m/z for C$_{32}$H34F$_2$N$_3$O (M+1)+=514.2; found m/z=514.1

The following compounds can also be prepared by analogous chemistry:

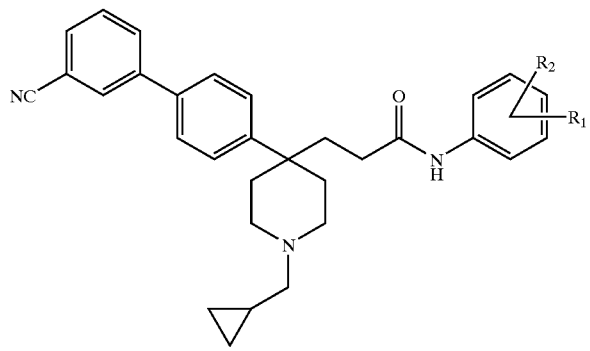

| Compound # | R$_1$ | R$_2$ | Molecular Formula (M + H)$^+$ | Calcd m/z | found m/z |
|---|---|---|---|---|---|
| 20G | 3-Cl | 5-Cl | C$_{31}$H$_{32}$Cl$_2$N$_3$O | 532.2 | 532.1 |
| 20H | 3-F | 5-F | C$_{31}$H$_{32}$F$_2$N$_3$O | 500.3 | 500.1 |
| 20I | 4-Cl | H | C$_{31}$H$_{33}$ClN$_3$O | 498.23 | 498.1 |
| 20J | 3-Cl | 4-F | C$_{31}$H$_{32}$ClFN$_3$O | 516.2 | 516.1 |
| 20K | 3-F | 5-CF$_3$ | C$_{32}$H$_{32}$F$_4$N$_3$O | 550.3 | 550.1 |

-continued

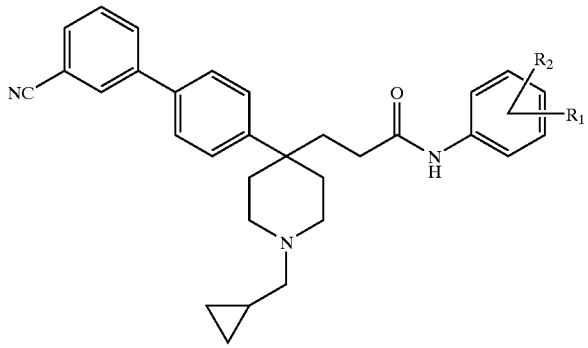

| Compound # | $R_1$ | $R_2$ | Molecular Formula $(M + H)^+$ | Calcd m/z | found m/z |
|---|---|---|---|---|---|
| 20L | 4-Cl | 3-$CF_3$ | $C_{32}H_{32}ClF_3N_3O$ | 566.2 | 566.1 |
| 20M | 3-Cl | 4-CN | $C_{32}H_{32}ClN_4O$ | 523.2 | 523.1 |

Procedure H:

A solution of 3.8 g (11.7 mmol) of compound 24, and 3.0 g (13.8mmol) of $(Boc)_2O$ in 60 mL of MeOH was stirred at room temperature for 18 h and concentrated. The residue was purified over silica gel eluting with 5 to 25% ethyl acetate in hexanes to give 3.45 g of compound 25. Calcd m/z for $C_{20}H_{29}BrNO_4$=426.1; found m/z=426.2.

Procedure I:

To a solution of 0.37 g (3 mmol) of 3,4-difluoroaniline in 3 mL of toluene was added 1.6 mL (3.2 mmol) of 2M $AlMe_3$ in toluene. After stirring at room temperature for 20 min, a solution of 1 g (2.35 mmol) of compound 25 in 3 mL of toluene was introduced. The mixture was stirred under reflux for 30 min and cooled to room temperature. It was diluted with 100 mL of ether, washed with 50 mL of 0.5N HCl, 50 mL of brine, and concentrated. The residue was purified over silica gel eluting with 5 to 25% ethyl acetate in hexanes plus 1% $NH_4OH$ to give 0.64 g of compound 26. Calcd m/z for $C_{25}H_{30}BrF_2N_2O_3$=523.1; found m/z=523.1.

Procedure J:

To a solution of 0.17 g (0.31 mmol) of compound 27 in 3 mL of $CH_2Cl_2$ was added 3 mL TFA. The mixture was stirred at room temperature for 40 min and concentrated. It was diluted with 30 mL of $CH_2Cl_2$, washed with 20 mL of saturated $NaHCO_3$, and 15 mL of brine. It was concentrated to give 0.124 g of crude compound 28. Calcd m/z for $C_{27}H_{26}F_2N_3O$=446.2; found m/z=446.1.

Procedure K:

To a solution of 0.02 g (0.045 mmol) of compound 28 in 1.5 mL of $CH_2Cl_2$ were added 0.05 g (0.5 mmol) of $Et_3N$ and 0.02 g (0.2 mmol) of $Ac_2O$. The mixture was stirred at room temperature for 18 h. Direct preparative TLC purification eluting with 10% MeOH in $CH_2Cl_2$ to give 0.02 g of compound 29A. Calcd m/z for $C_{29}H_{28}F_2N_3O_2$=488.2; found m/z=488.1.

The following compounds can be prepared analogously.

Compound 29B: Calcd m/z for $C_{28}H_{28}F_2N_3O_3S$=524.2; found m/z=524.1.

Compound 29C: Calcd m/z for $C_{30}H_{30}F_2N_3O_3$=518.2; found m/z=518.1.

Compound 29D: Calcd m/z for $C_{32}H_{35}F_2N_4O_2$=545.2; found m/z=545.1.

Compound 29E: Calcd m/z for $C_{29}H_{31}F_2N_4O_3S$=553.2; found m/z=553.1

Compound 29F: Calcd m/z for $C_{29}H_{31}F_2N_4O_3S$=553.2; found m/z=553.1

MCH Receptor Binding Assay

Membranes from CHO cells expressing the MCH receptor were prepared by lysing cells with 5 mM HEPES for 15 min at 4C. Cell lysates were centrifuged (12.5000×g, 15 min) and the pellet was re-suspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM $MGCl_2$, 10 mM NaCl, 5 mM $MnCl_2$, 0.1% BSA). The membrane/bead mixture was centrifuged (1500×g, 3.5 min), the supernatant was aspirated, and the pellet was re-suspended in 10 ml binding buffer. The centrifugation, aspiration and re-suspension were then repeated. The membrane/bead mixture (100 µl) was then added to 96-well plates containing 50 µl of 500 pM [$^{125}$I]-MCH (NEN) and 50 ml of the appropriate concentration of compound (4× the desired final concentration). Nonspecific binding was determined by including 1 µM MCH in the binding reaction. The binding reaction was incubated at room temperature for 2 h. Plates were then analyzed in a TOPCOUNT microplate scintillation counter (Packard). Data was analyzed and Ki values were determined using GraphPad Prism.

For the compounds of this invention, a range of MCH receptor binding activity (Ki values) of from about 3 nM to about 1500 nM was observed. Compounds of this invention have a binding activity in the range of from about 3 nM to about 1000 nM.

TABLE 1

| Structure | Avg. MCH Ki (nM) |
|---|---|
| 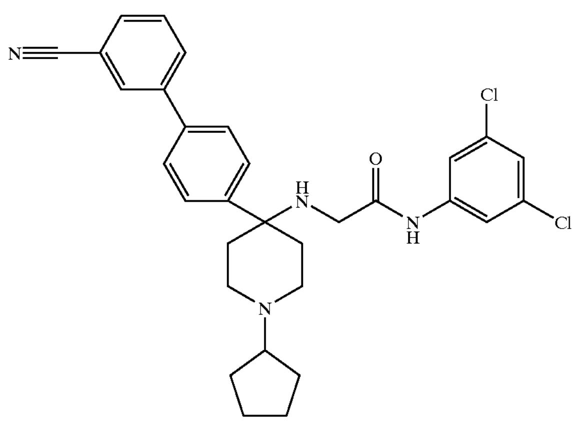 | 3.2 |
| 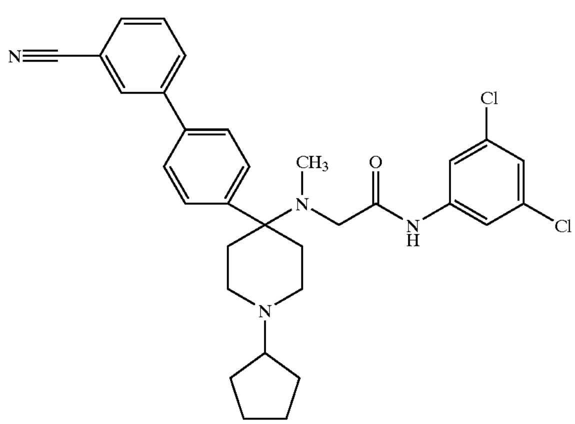 | 8.6 |

TABLE 1-continued

| Structure | Avg. MCH Ki (nM) |
|---|---|
| (structure) | 16 |
| (structure) | 18 |

TABLE 1-continued
| Structure | Avg. MCH Ki (nM) |
|---|---|
| 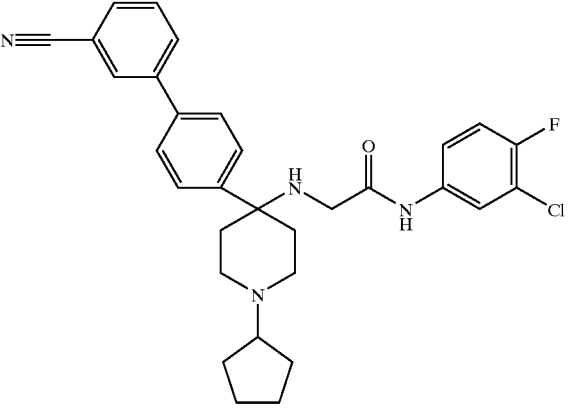 | 2.6 |
| 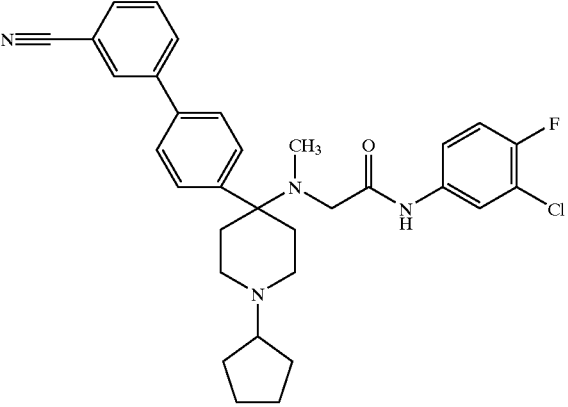 | 4.2 |
| 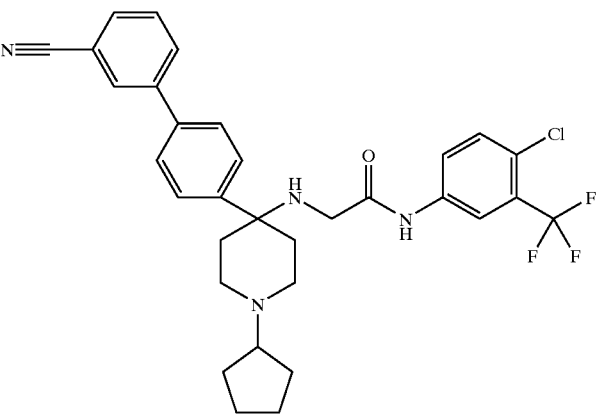 | 23 |

TABLE 1-continued
| Structure | Avg. MCH Ki (nM) |
|---|---|
| 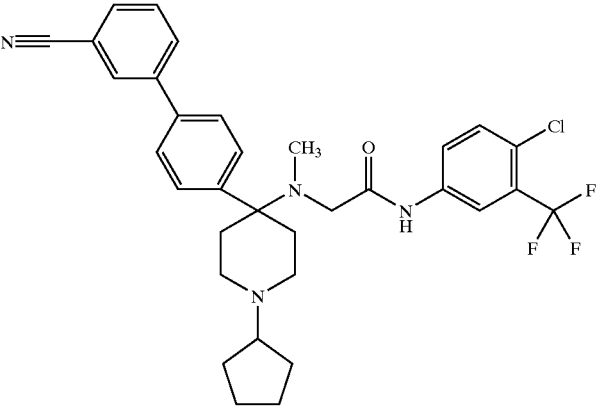 | 16 |
| 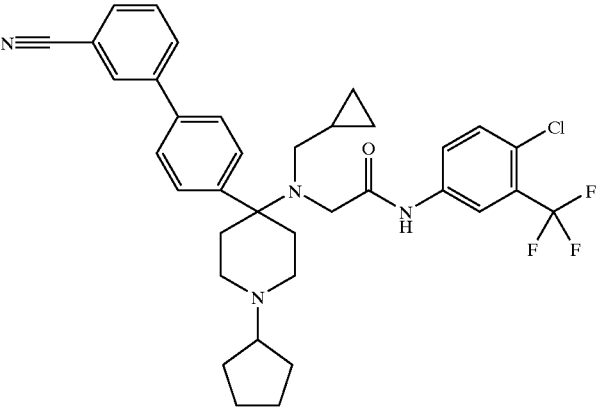 | |
| 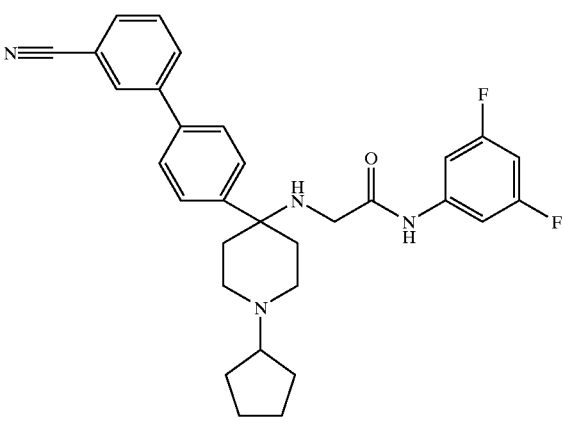 | 2.5 |

TABLE 1-continued

| Structure | Avg. MCH Ki (nM) |
|---|---|
| 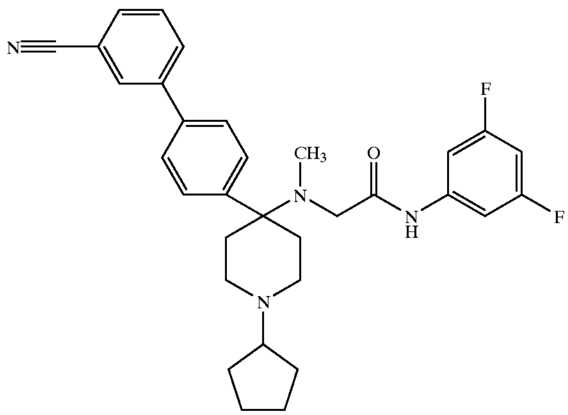 | 6.2 |
| 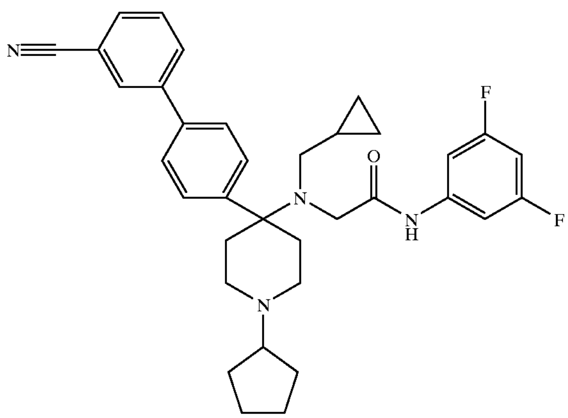 | 69 |
| 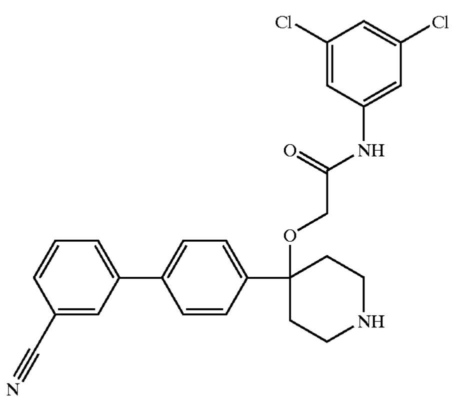 | 3.2 |

TABLE 1-continued
| Structure | Avg. MCH Ki (nM) |
|---|---|
| 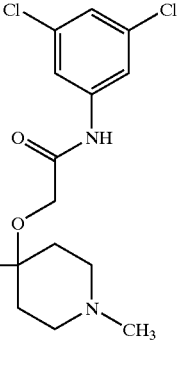 | 4 |
| 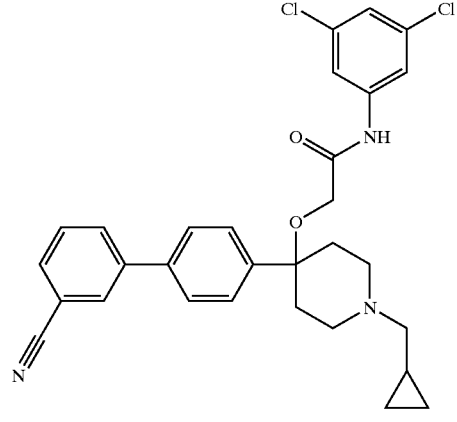 | 1.8 |
| 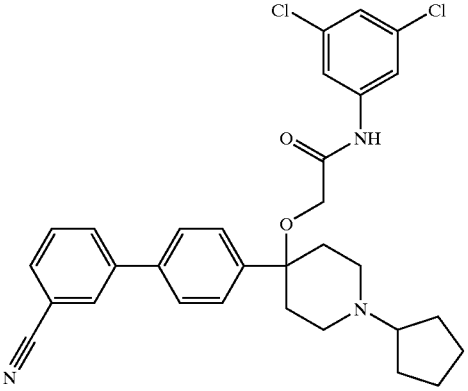 | 2.2 |

TABLE 1-continued
| Structure | Avg. MCH Ki (nM) |
|---|---|
| 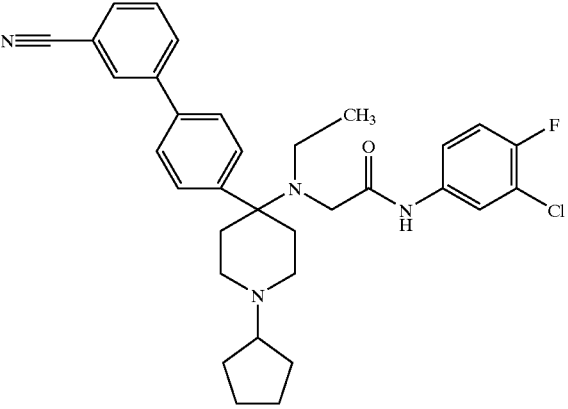 | 10.6 |
| 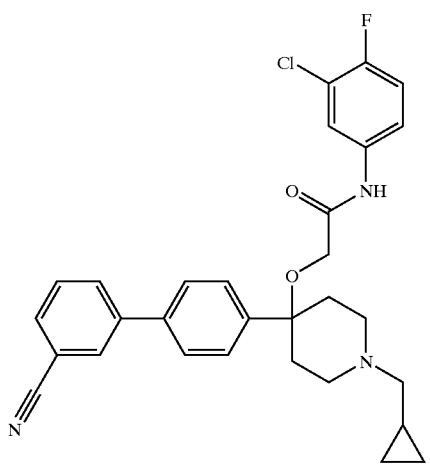 | 2 |
| 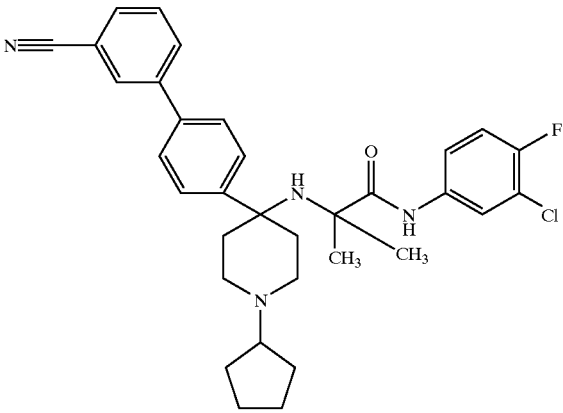 | |

TABLE 1-continued

| Structure | Avg. MCH Ki (nM) |
|---|---|
|  |  |
| 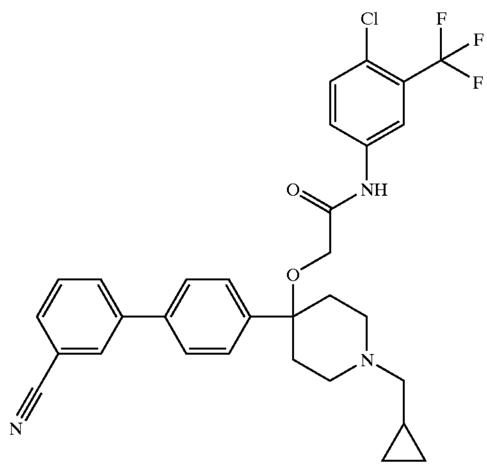 | 23 |
| 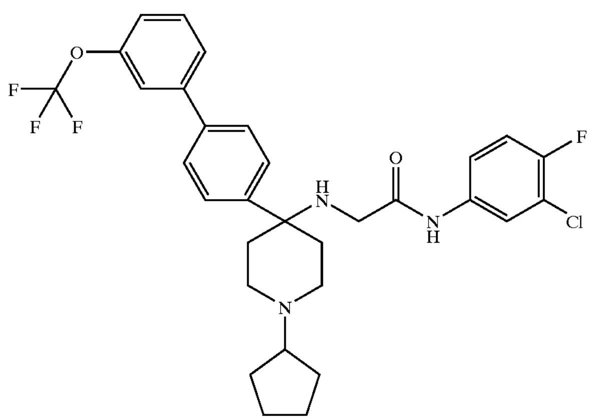 | 76 |

TABLE 1-continued
| Structure | Avg. MCH Ki (nM) |
|---|---|
| 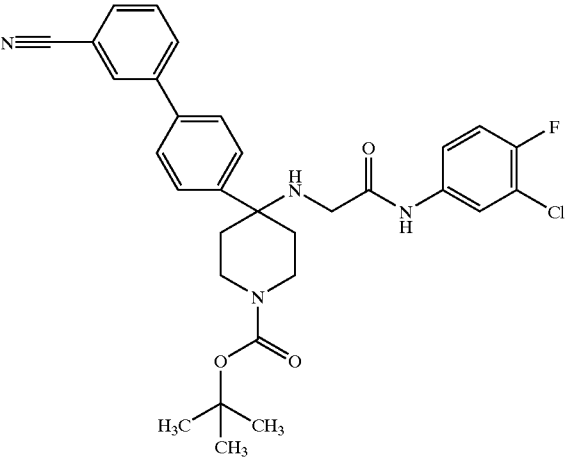 | 56 |
| 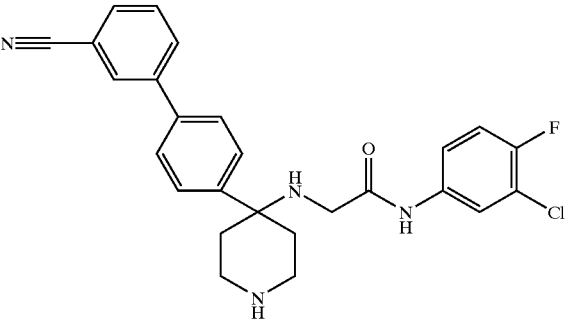 | 3 |
| 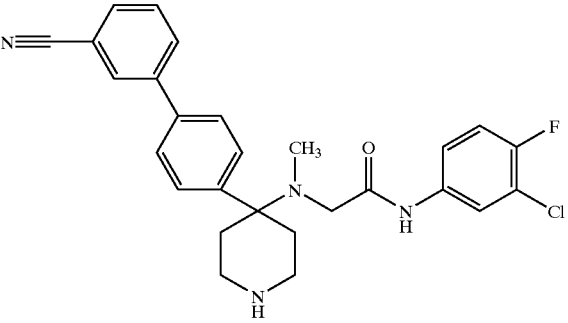 | 4.7 |
| 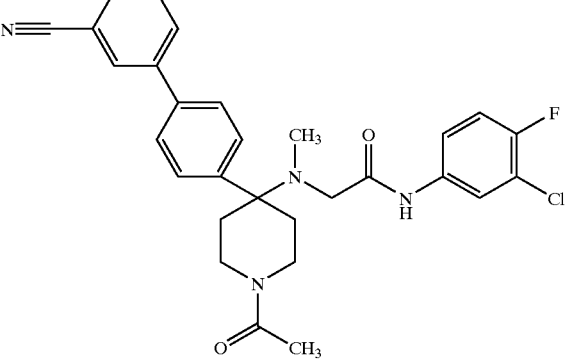 | 25 |

TABLE 1-continued
| Structure | Avg. MCH Ki (nM) |
|---|---|
| 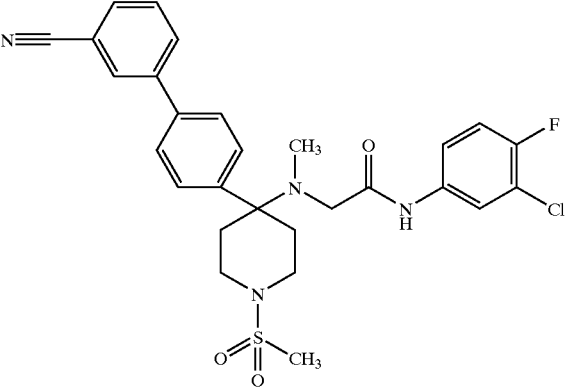 | 70 |
| 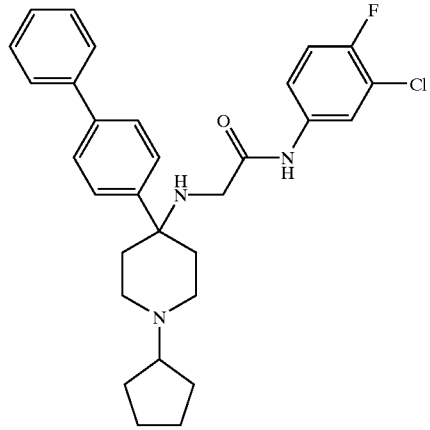 | |
| 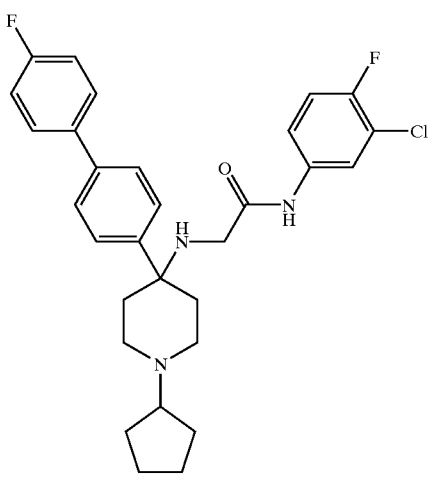 | |

TABLE 1-continued

| Structure | Avg. MCH Ki (nM) |
|---|---|
| | |
| 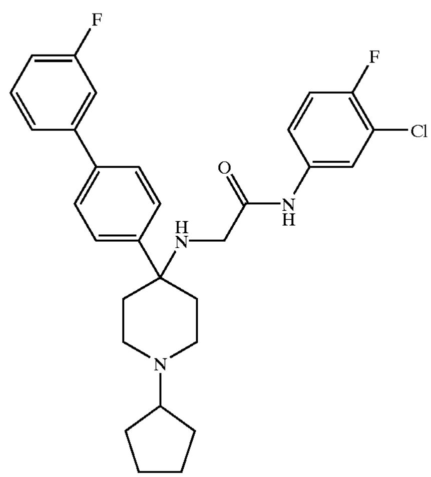 | 99 |
| | |

TABLE 1-continued

| Structure | Avg. MCH Ki (nM) |
|---|---|
| | |
| | 63 |

TABLE 1-continued

| Structure | Avg. MCH Ki (nM) |
|---|---|
| | |
| 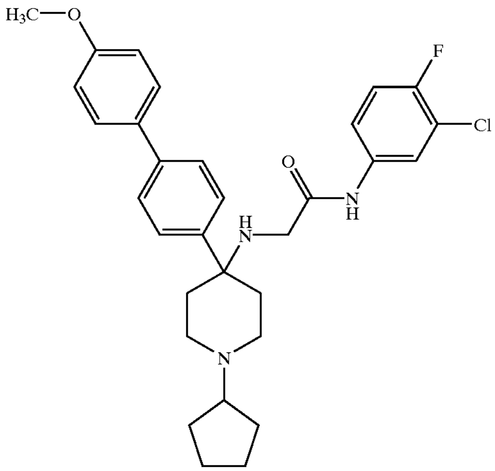 | 77 |

TABLE 1-continued

| Structure | Avg. MCH Ki (nM) |
|---|---|

TABLE 1-continued
| Structure | Avg. MCH Ki (nM) |
|---|---|
| 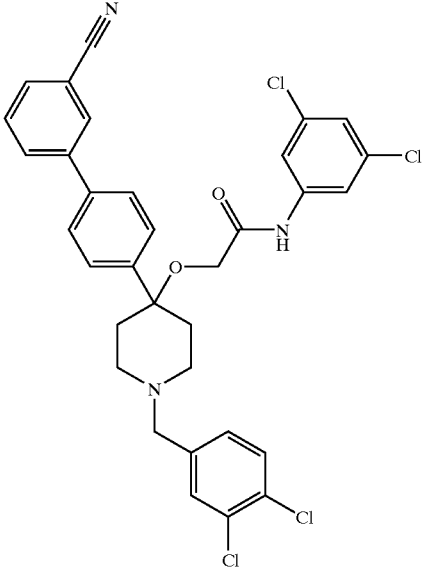 | |
| 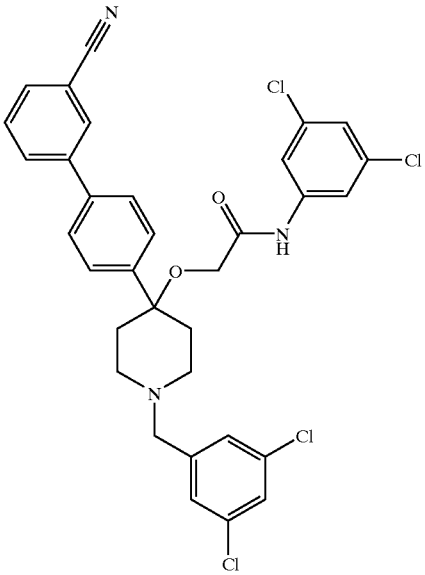 | |

TABLE 1-continued
| Structure | Avg. MCH Ki (nM) |
|---|---|
| 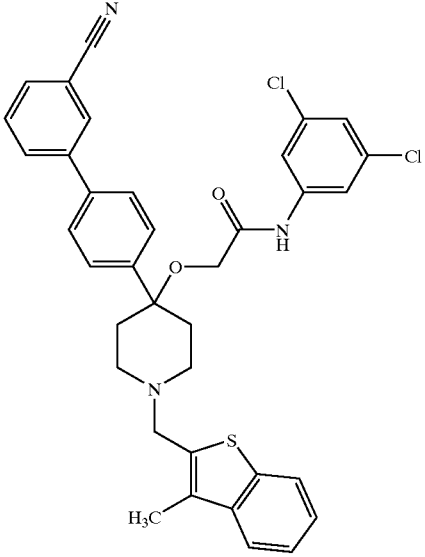 | |
| 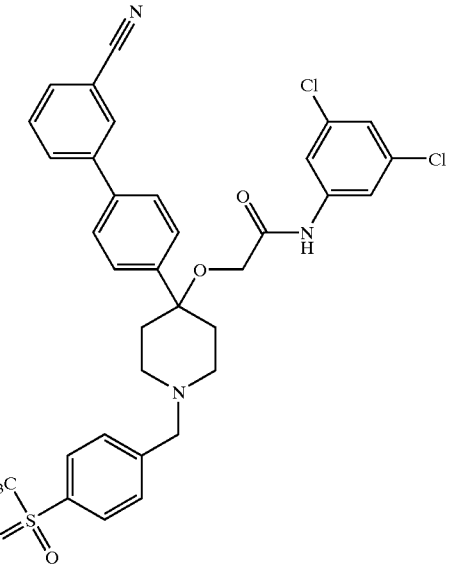 | 76 |

TABLE 1-continued
| Structure | Avg. MCH Ki (nM) |
|---|---|
| 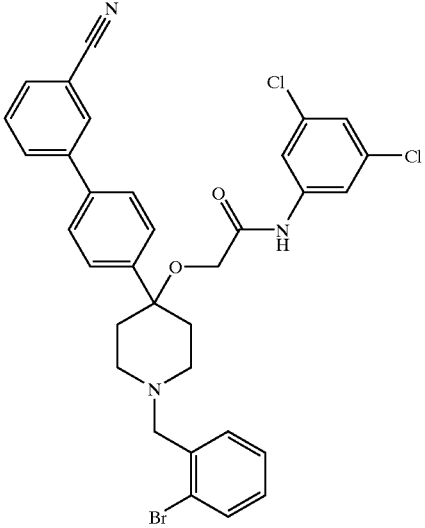 | |
| 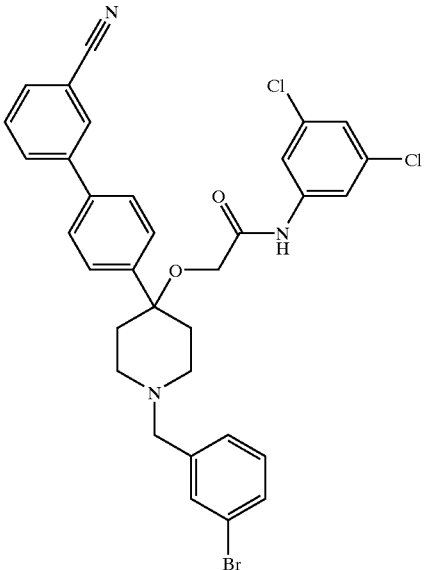 | |

TABLE 1-continued
| Structure | Avg. MCH Ki (nM) |
|---|---|
| 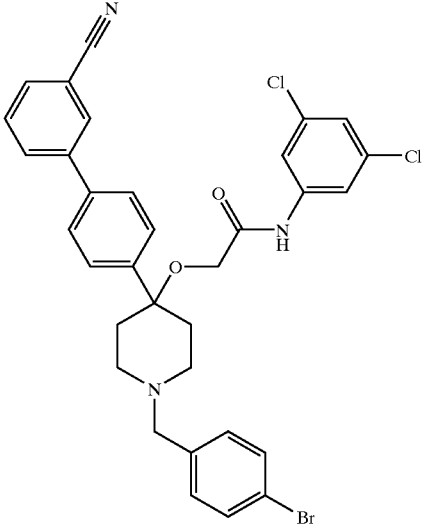 | |
| 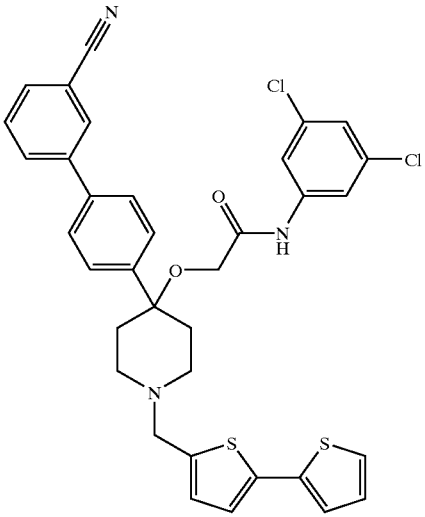 | |

TABLE 1-continued
| Structure | Avg. MCH Ki (nM) |
|---|---|
| 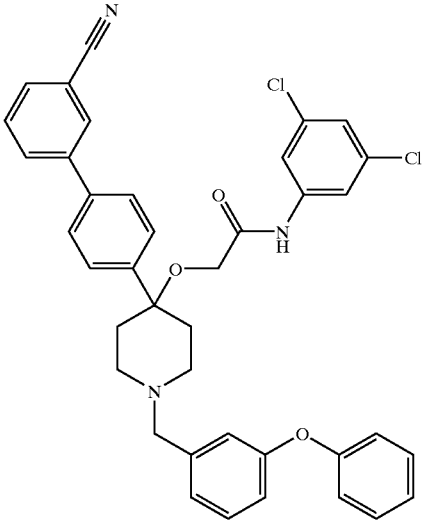 | |
| 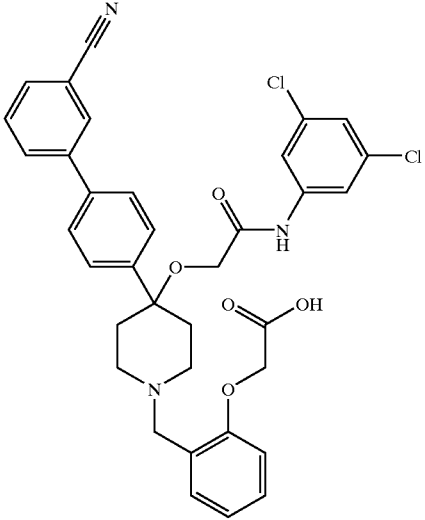 | |
| 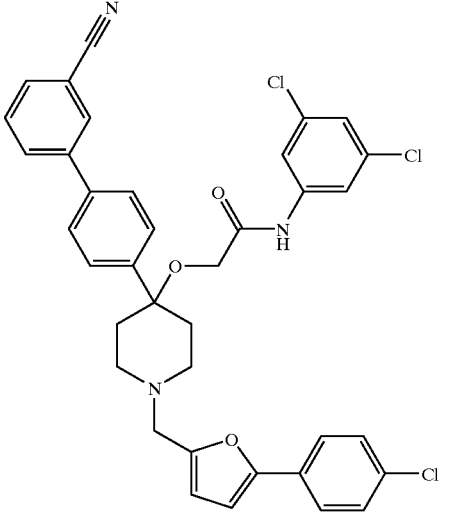 | |

TABLE 1-continued
| Structure | Avg. MCH Ki (nM) |
|---|---|
| 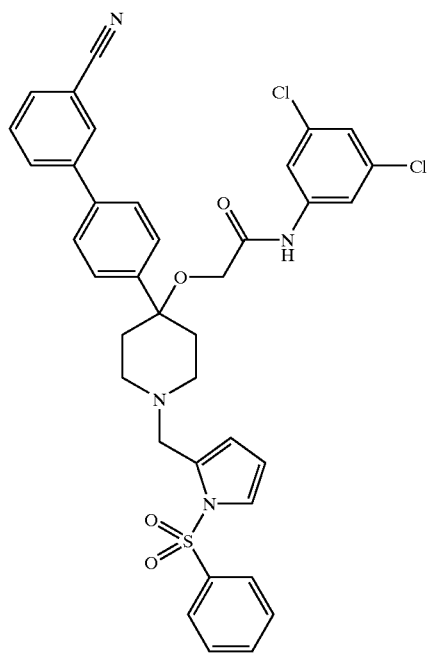 | |
| 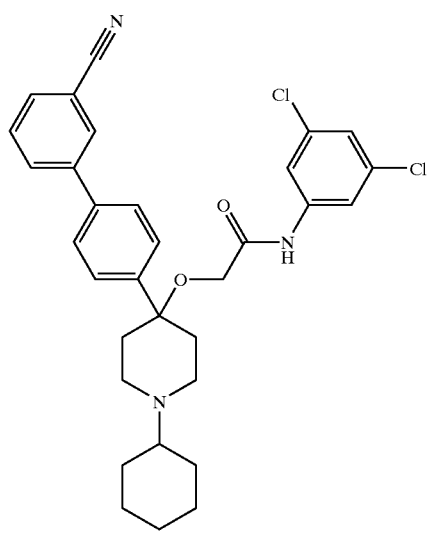 | 19 |

TABLE 1-continued
| Structure | Avg. MCH Ki (nM) |
|---|---|
| 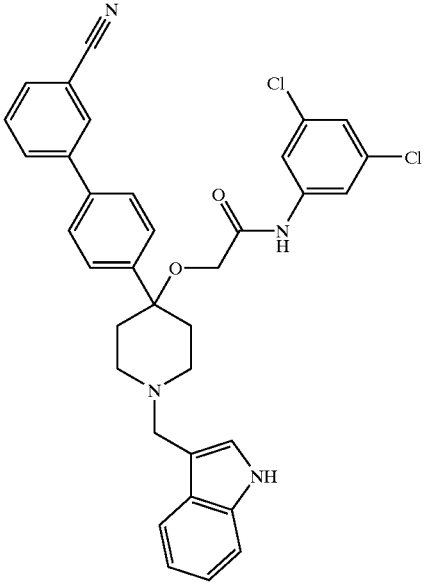 | |
| 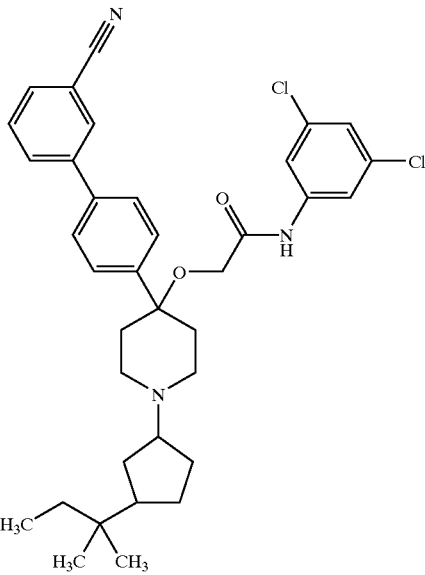 | |

TABLE 1-continued
| Structure | Avg. MCH Ki (nM) |
|---|---|
| 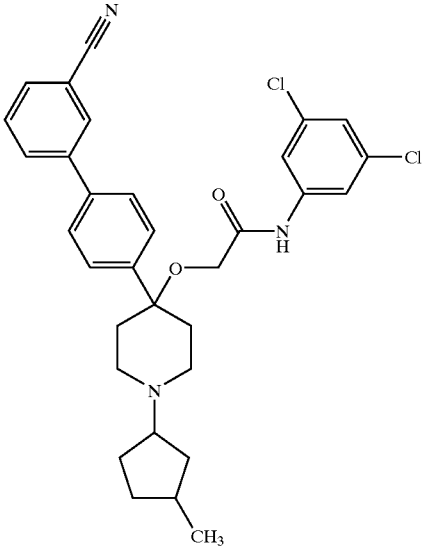 | 11 |
| 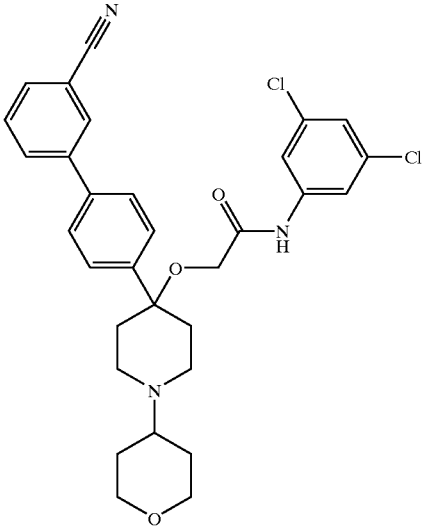 | 9 |

TABLE 1-continued
| Structure | Avg. MCH Ki (nM) |
|---|---|
| 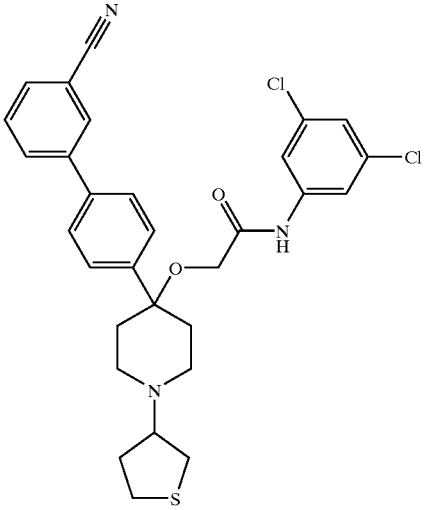 | 19 |
| 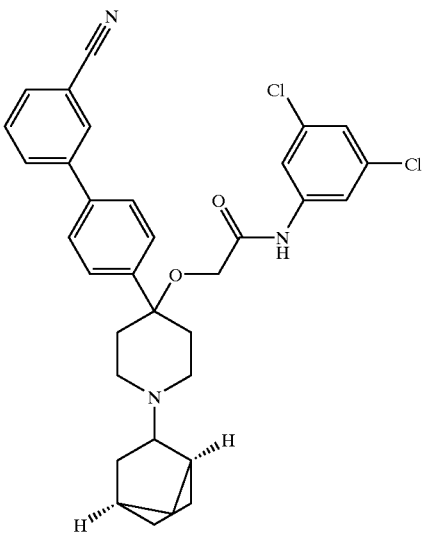 | 15 |

TABLE 1-continued
| Structure | Avg. MCH Ki (nM) |
|---|---|
| 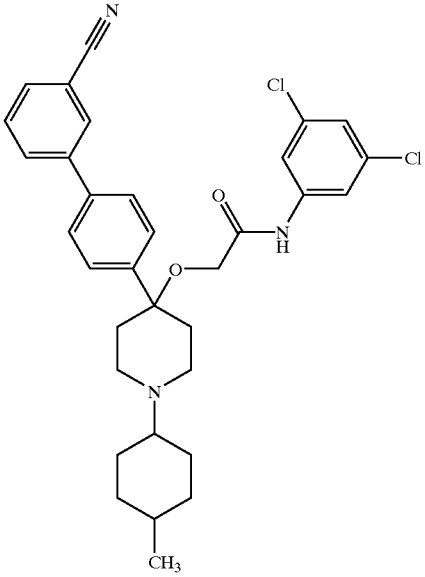 | 13 |
| 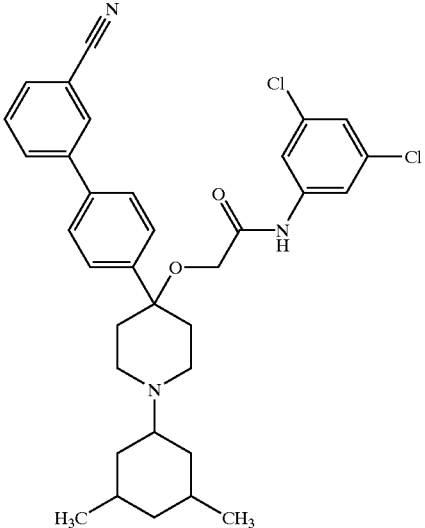 | 20 |

TABLE 1-continued

| Structure | Avg. MCH Ki (nM) |
|---|---|
| *[structure]* | 62 |
| *[structure]* | 20 |

TABLE 1-continued
| Structure | Avg. MCH Ki (nM) |
|---|---|
| 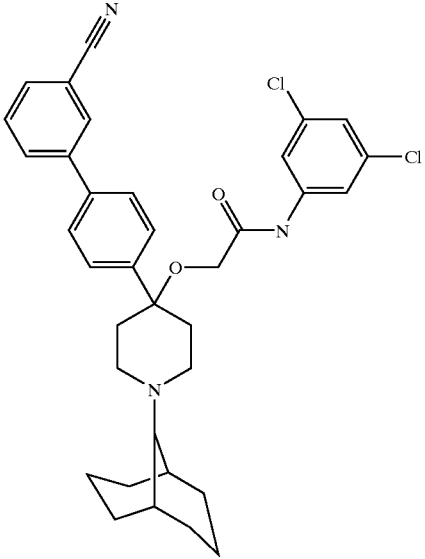 | 48 |
| 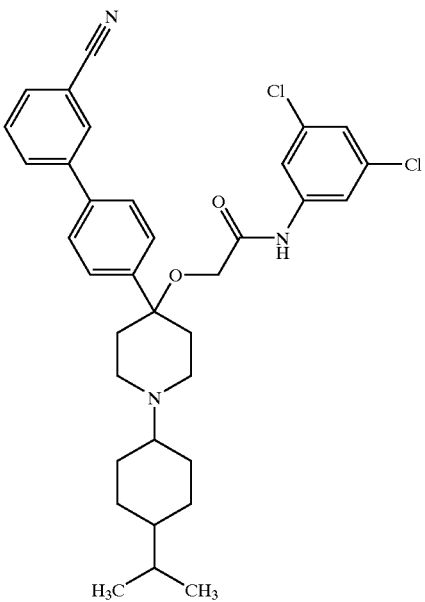 | 19 |

TABLE 1-continued
| Structure | Avg. MCH Ki (nM) |
|---|---|
| 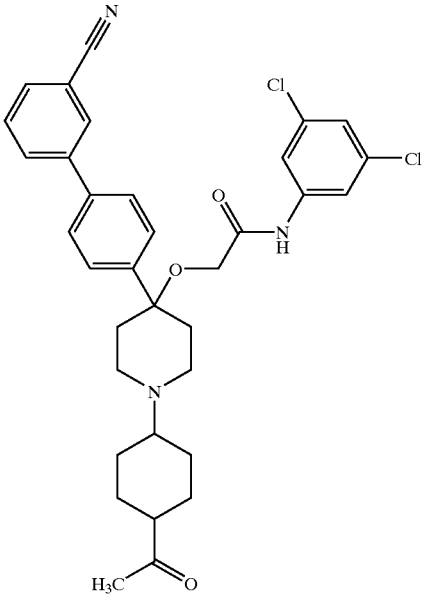 | 6 |
| 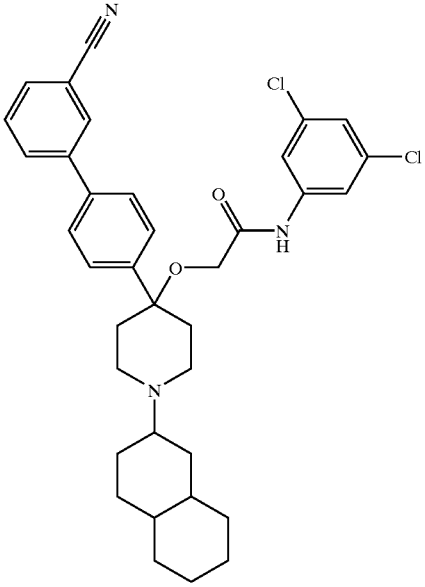 | 36 |

TABLE 1-continued
| Structure | Avg. MCH Ki (nM) |
|---|---|
| 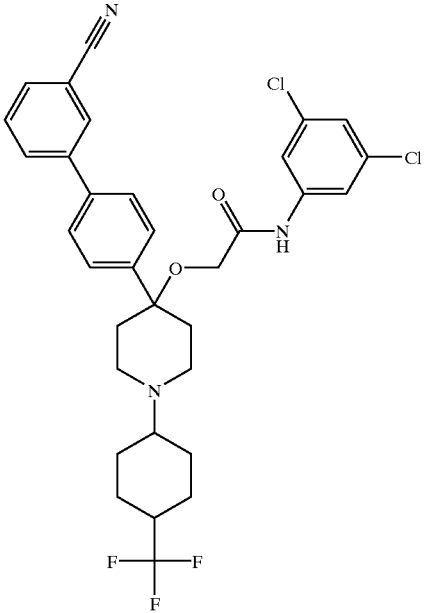 | 49 |
| 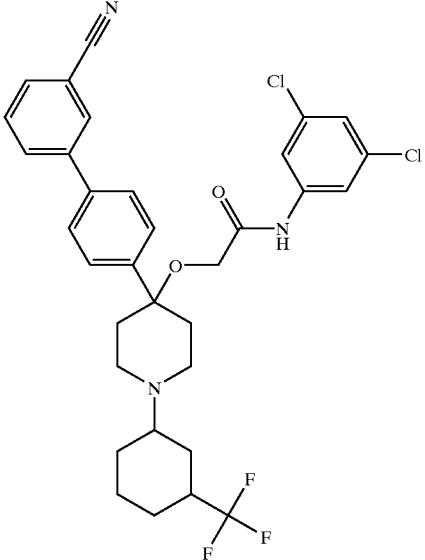 | 86 |

TABLE 1-continued
| Structure | Avg. MCH Ki (nM) |
|---|---|
| 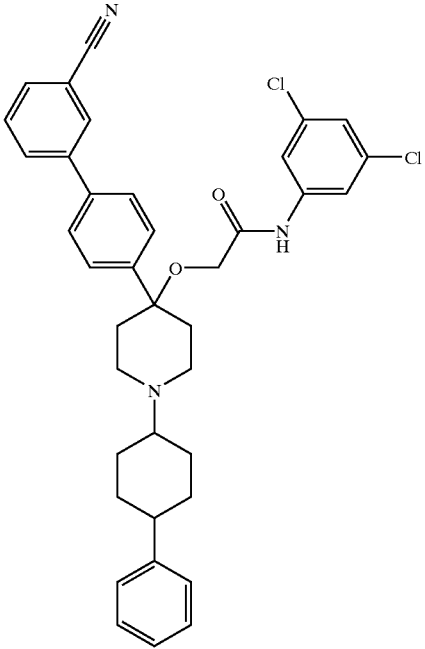 | 95 |
| 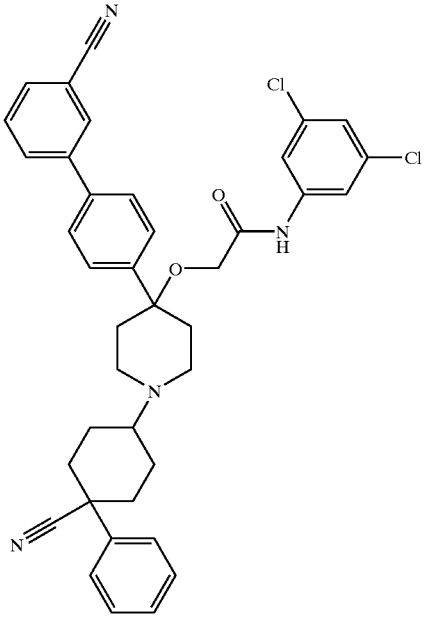 | |

TABLE 1-continued

| Structure | Avg. MCH Ki (nM) |
|---|---|
| *(structure)* | 30 |
| *(structure)* | 21 |

TABLE 1-continued
| Structure | Avg. MCH Ki (nM) |
|---|---|
| 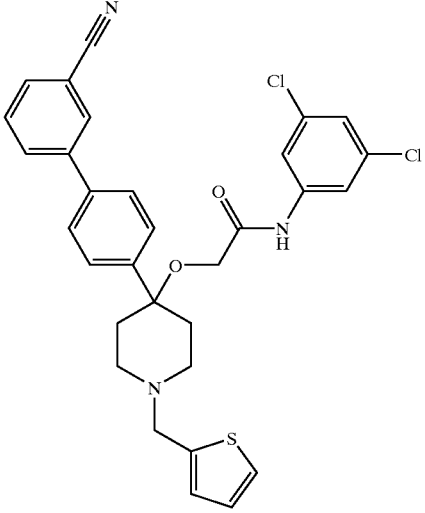 | 26 |
| 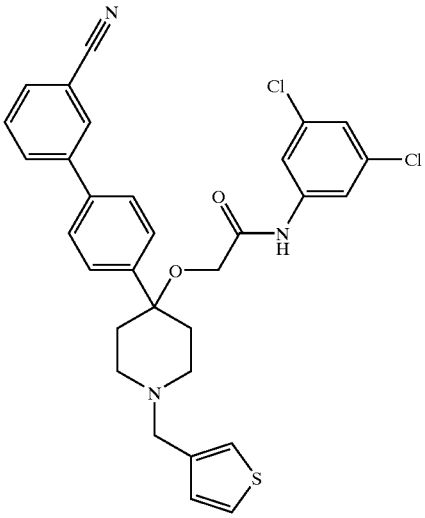 | 27 |
| 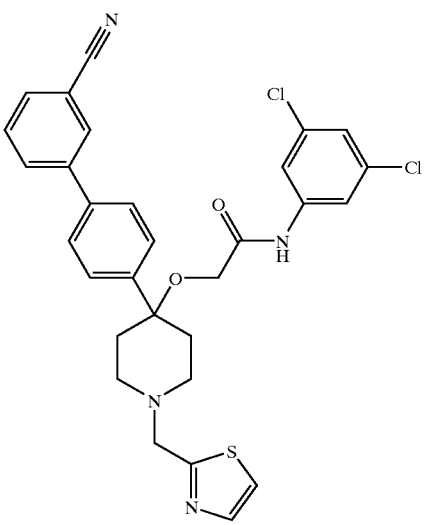 | |

TABLE 1-continued

| Structure | Avg. MCH Ki (nM) |
|---|---|

TABLE 1-continued
| Structure | Avg. MCH Ki (nM) |
|---|---|
| 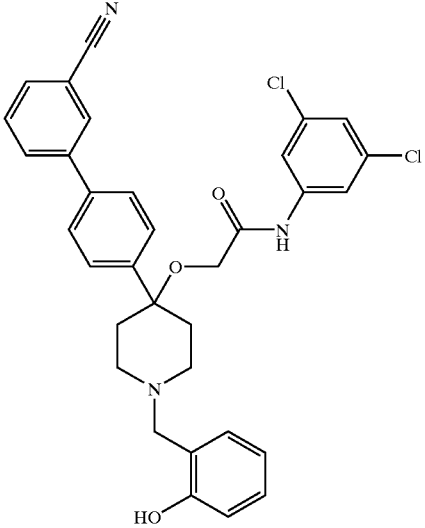 | |
| 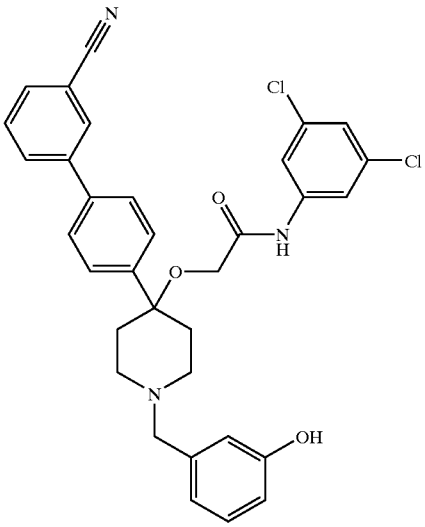 | 19 |

TABLE 1-continued
| Structure | Avg. MCH Ki (nM) |
|---|---|
| 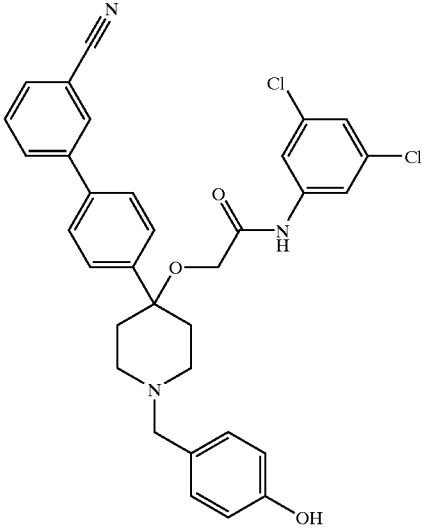 | 20 |
| 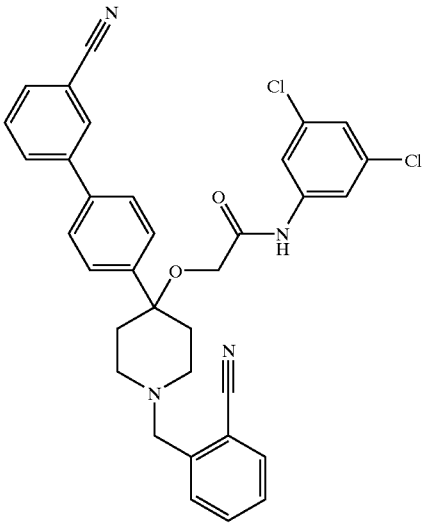 | |

TABLE 1-continued
| Structure | Avg. MCH Ki (nM) |
|---|---|
| 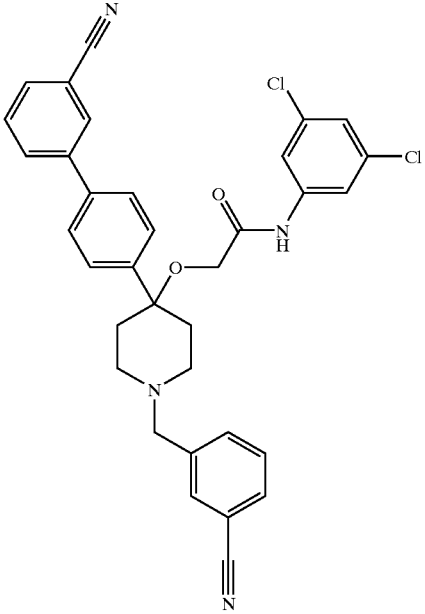 | |
| 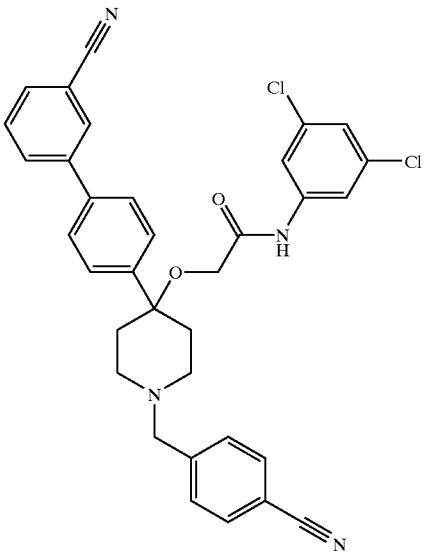 | |

TABLE 1-continued
| Structure | Avg. MCH Ki (nM) |
|---|---|
| 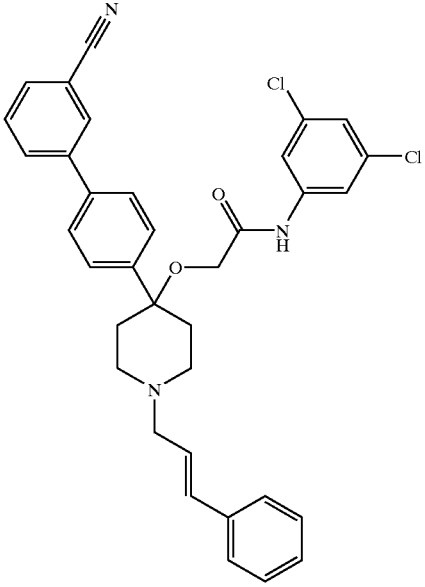 | |
| 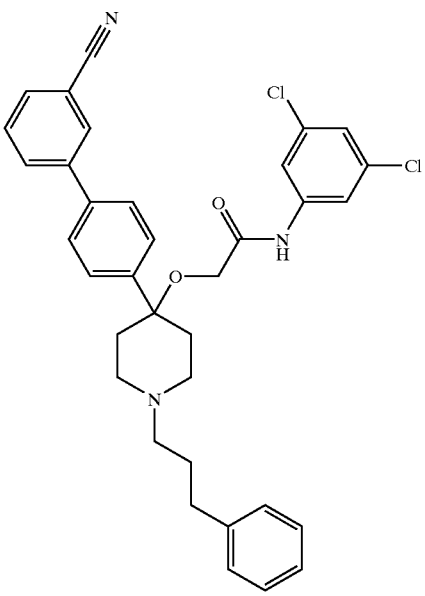 | 50 |

TABLE 1-continued
| Structure | Avg. MCH Ki (nM) |
|---|---|
| 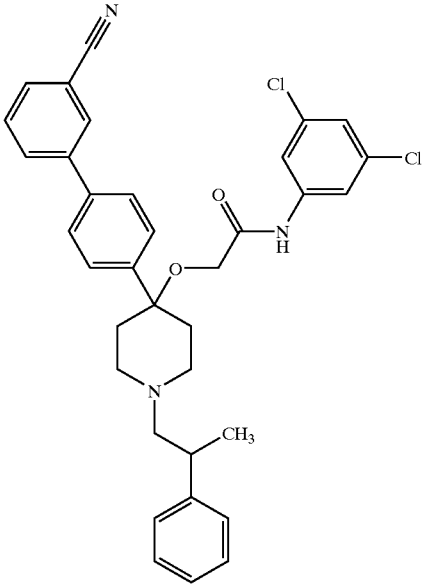 | 42 |
| 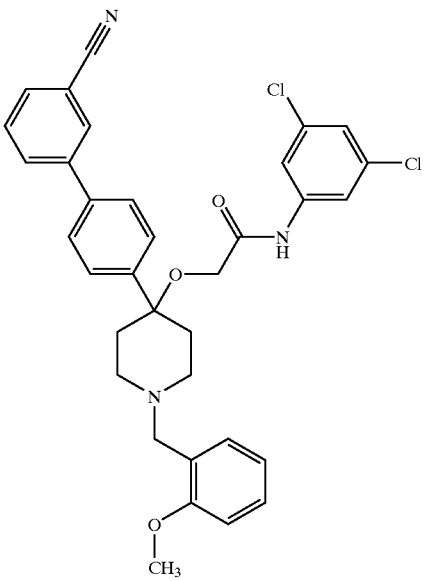 | 15 |

TABLE 1-continued
| Structure | Avg. MCH Ki (nM) |
|---|---|
| 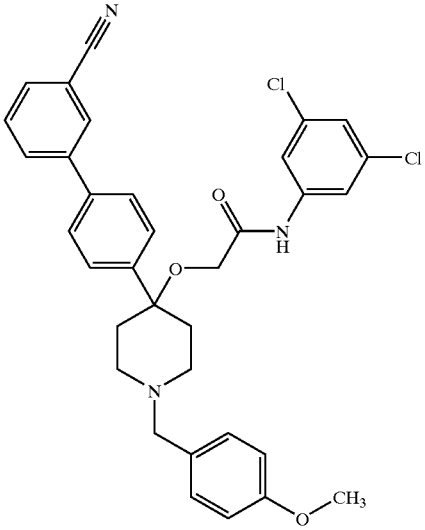 | 39 |
| 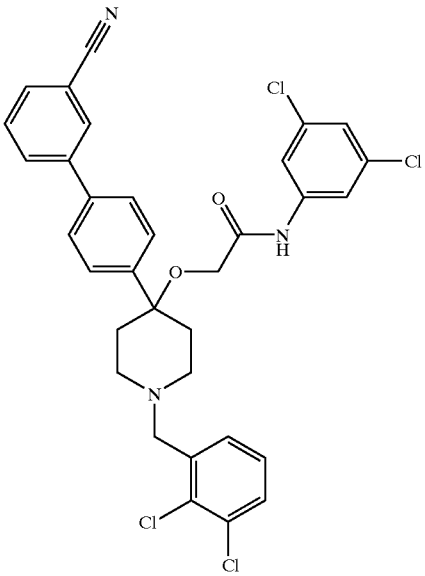 | |

TABLE 1-continued
| Structure | Avg. MCH Ki (nM) |
|---|---|
| 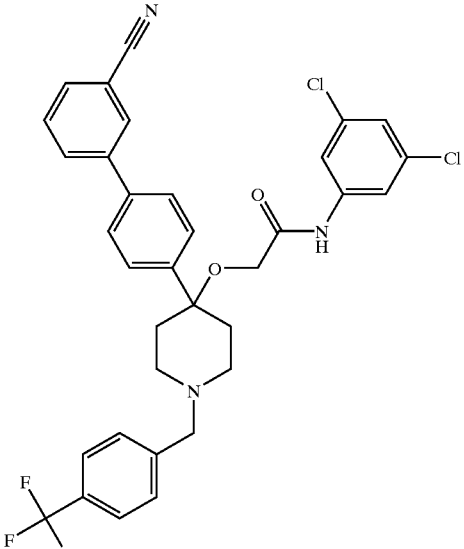 | |
| 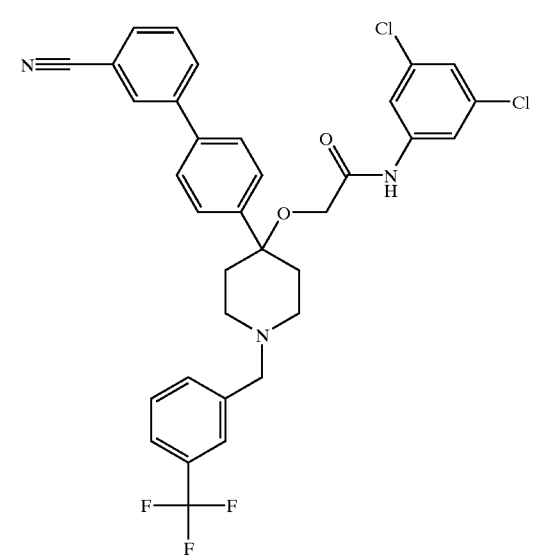 | |

TABLE 1-continued
| Structure | Avg. MCH Ki (nM) |
|---|---|
| 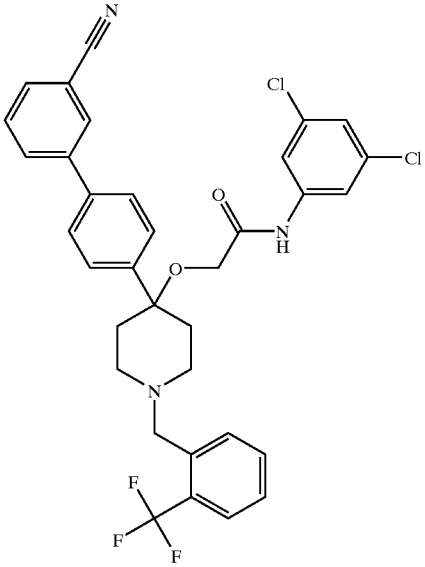 | |
| 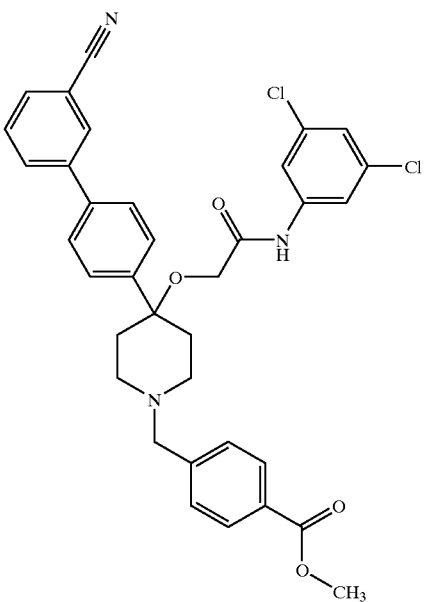 | |

TABLE 1-continued
| Structure | Avg. MCH Ki (nM) |
|---|---|
| 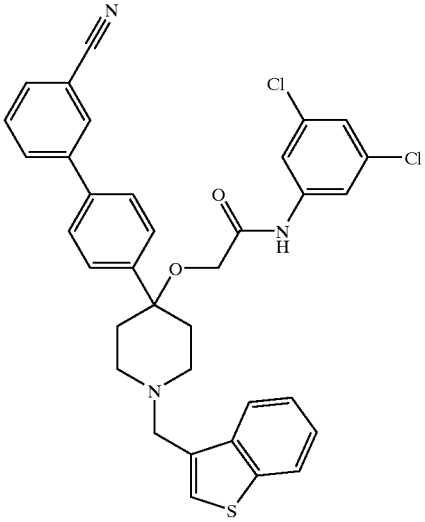 | |
| 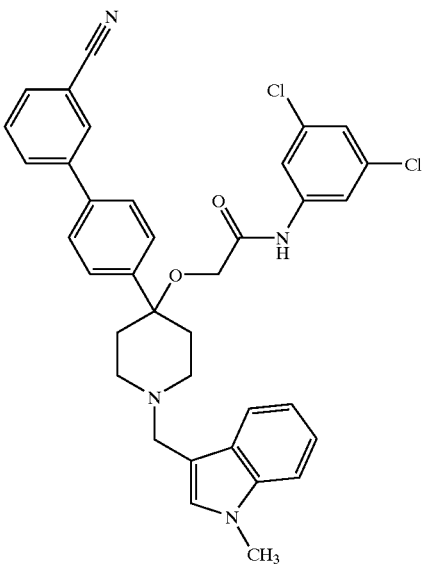 | |

TABLE 1-continued
| Structure | Avg. MCH Ki (nM) |
|---|---|
| 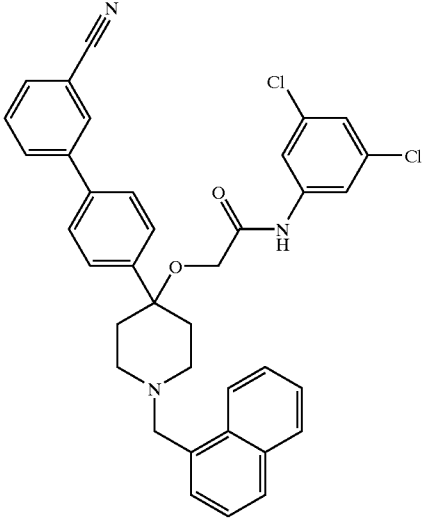 | |
| 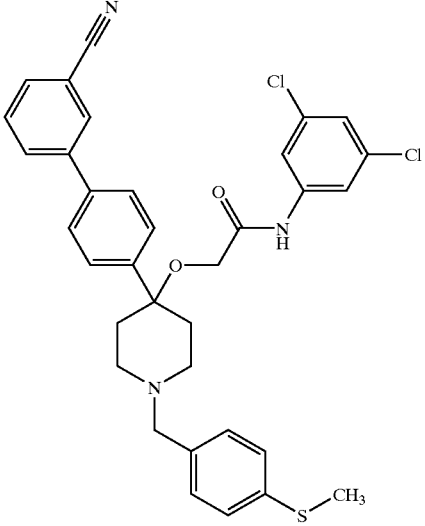 | |

TABLE 1-continued
| Structure | Avg. MCH Ki (nM) |
|---|---|
| 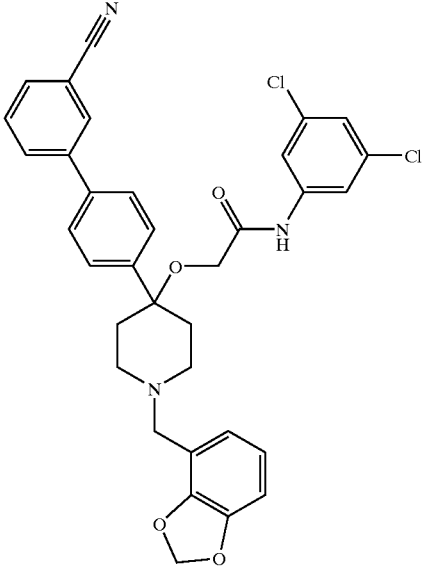 | |
| 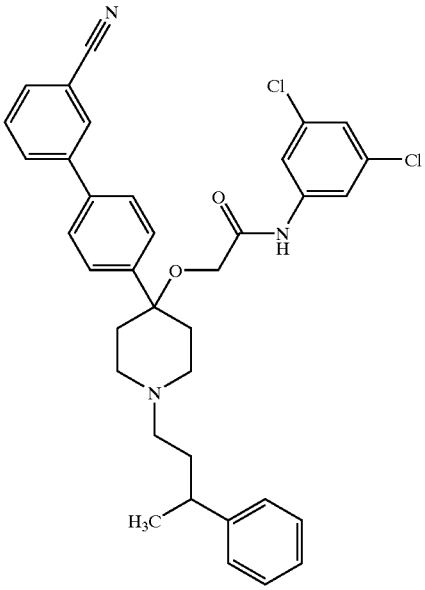 | 72 |

TABLE 1-continued
| Structure | Avg. MCH Ki (nM) |
|---|---|
| 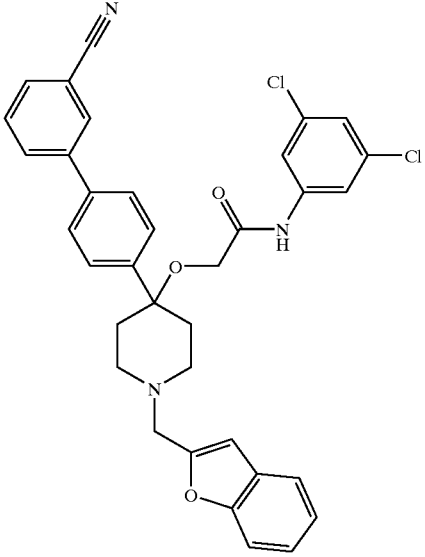 | |
| 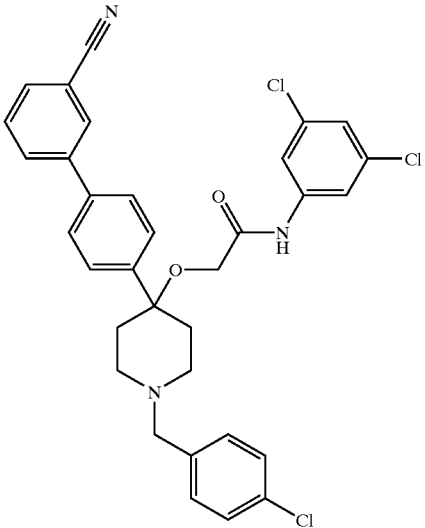 | |

TABLE 1-continued

| Structure | Avg. MCH Ki (nM) |
|---|---|

TABLE 1-continued
| Structure | Avg. MCH Ki (nM) |
|---|---|
| 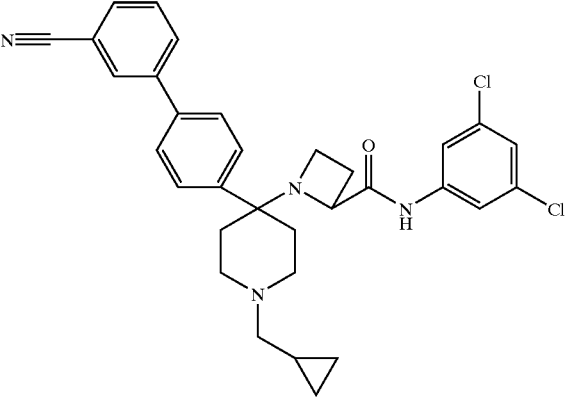 | |
| 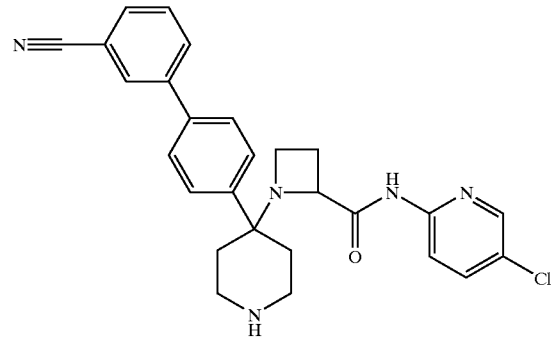 | |
| 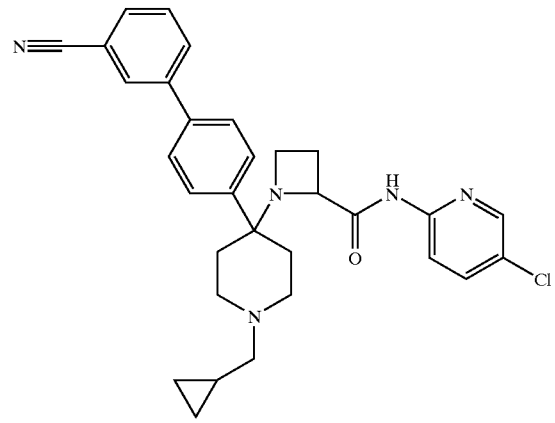 | |

TABLE 1-continued

| Structure | Avg. MCH Ki (nM) |
|---|---|

TABLE 1-continued

| Structure | Avg. MCH Ki (nM) |
|---|---|
| | |
| 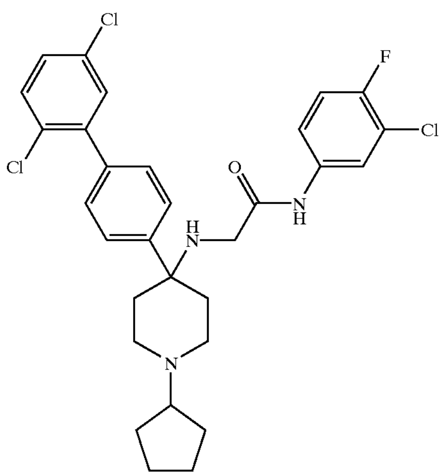 | 52 |
| | |

TABLE 1-continued

| Structure | Avg. MCH Ki (nM) |
|---|---|

10

TABLE 1-continued
| Structure | Avg. MCH Ki (nM) |
|---|---|
| 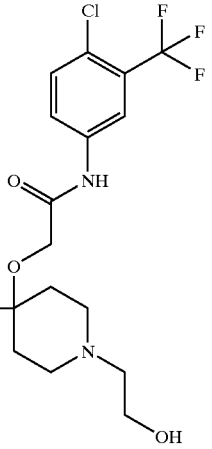 | 48 |
| 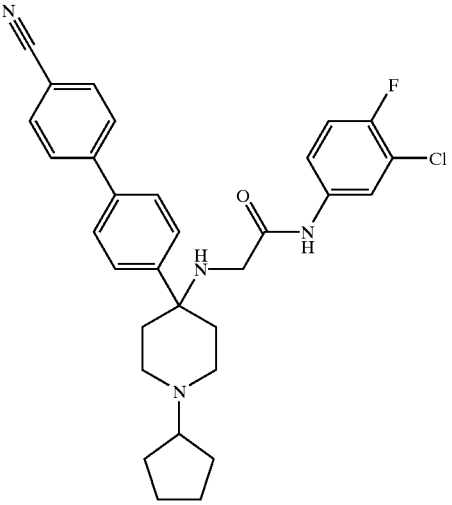 | |
| 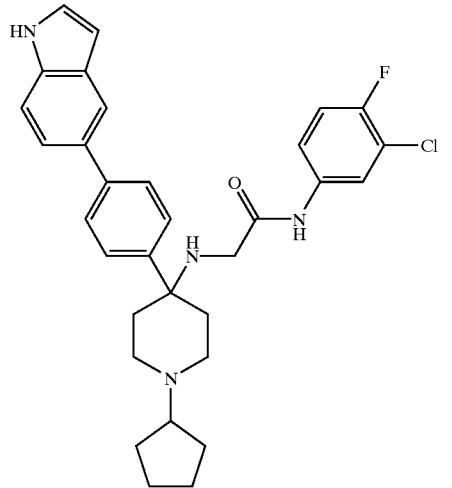 | |

TABLE 1-continued
| Structure | Avg. MCH Ki (nM) |
|---|---|
| 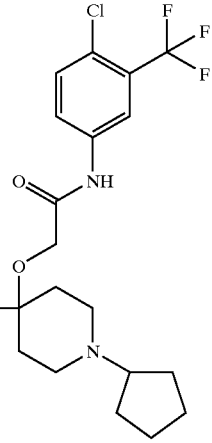 | 49 |
| 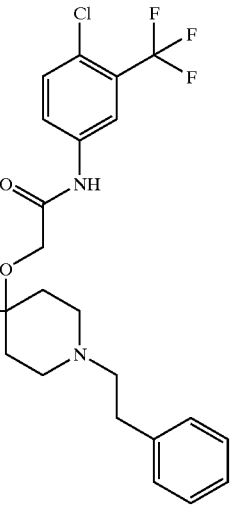 | |
| 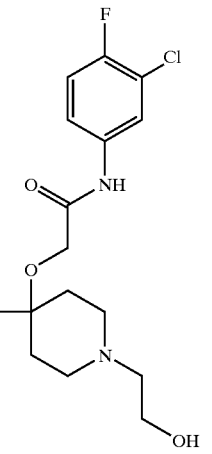 | 8.2 |

TABLE 1-continued
| Structure | Avg. MCH Ki (nM) |
|---|---|
| 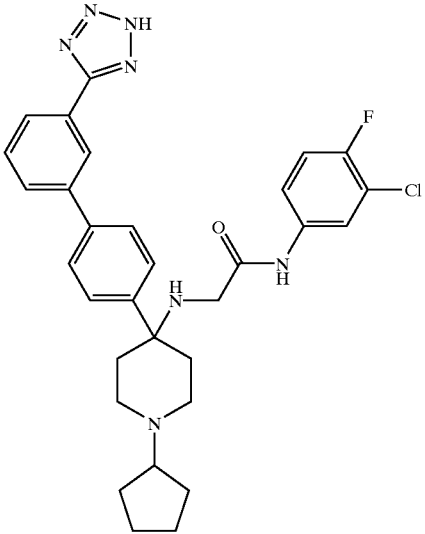 | |
| 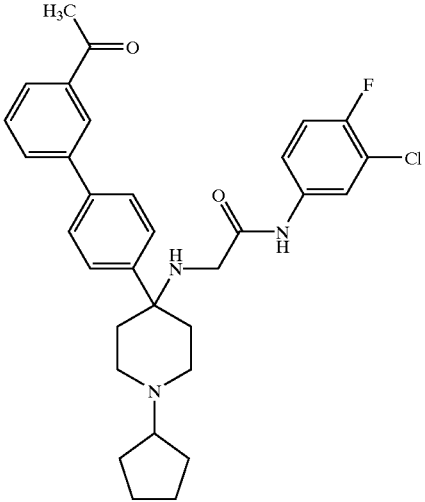 | |
| 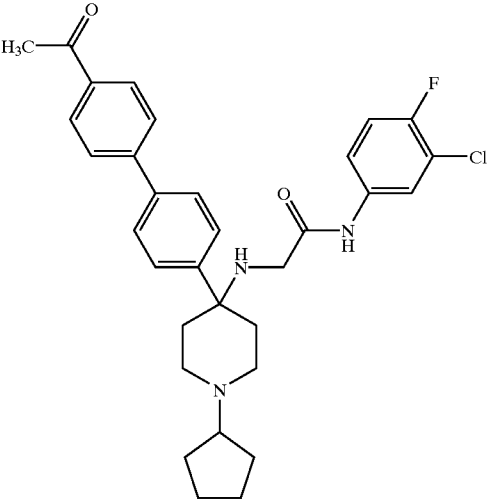 | |

TABLE 1-continued
| Structure | Avg. MCH Ki (nM) |
|---|---|
| 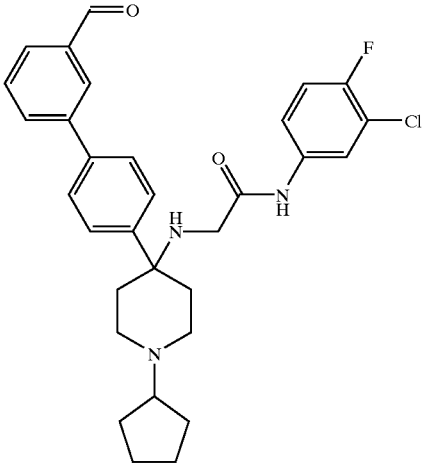 | 21 |
| 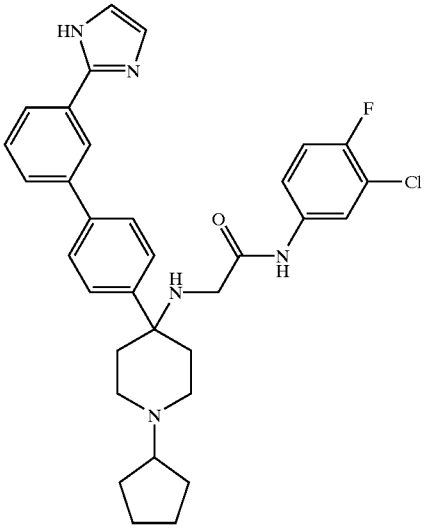 | 8.3 |
| 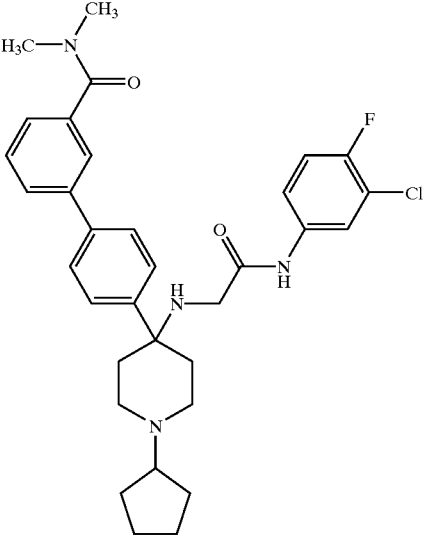 | |

TABLE 1-continued

| Structure | Avg. MCH Ki (nM) |
|---|---|
| | |
| | |
| | |

TABLE 1-continued
| Structure | Avg. MCH Ki (nM) |
|---|---|
| 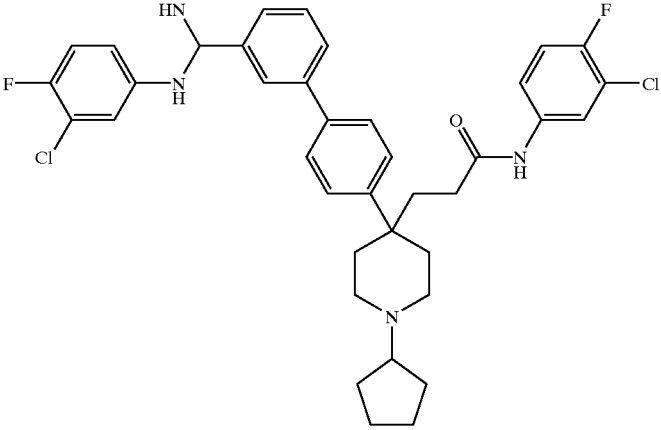 | |
| 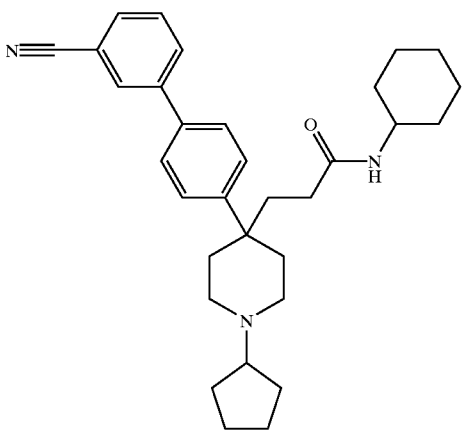 | |
| 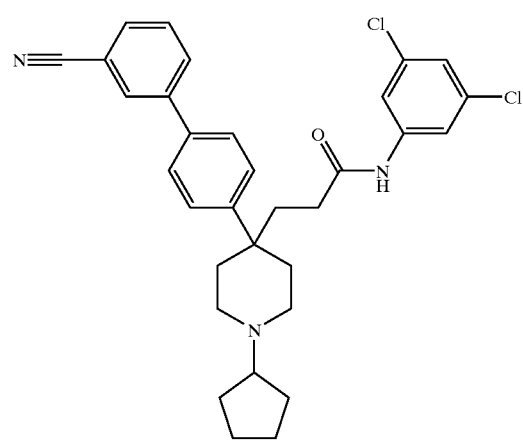 | 35.5 |

TABLE 1-continued
| Structure | Avg. MCH Ki (nM) |
|---|---|
| 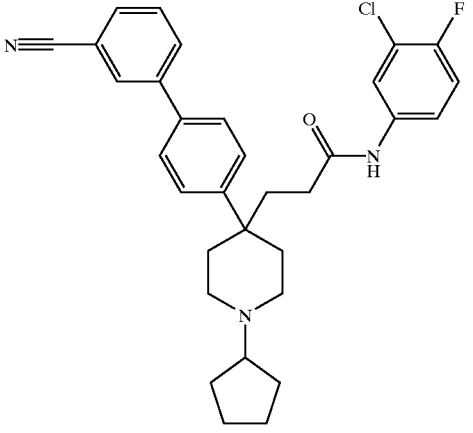 | 26 |
| 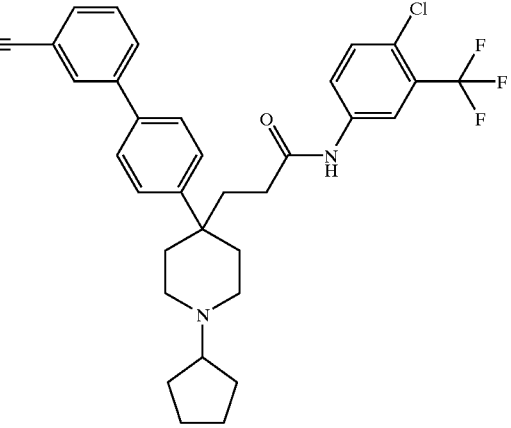 | |
| 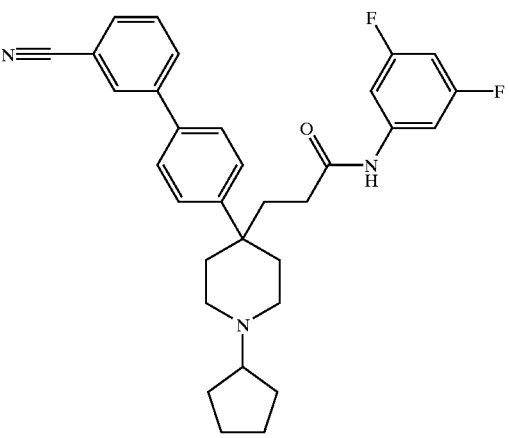 | 36 |

TABLE 1-continued
| Structure | Avg. MCH Ki (nM) |
|---|---|
| 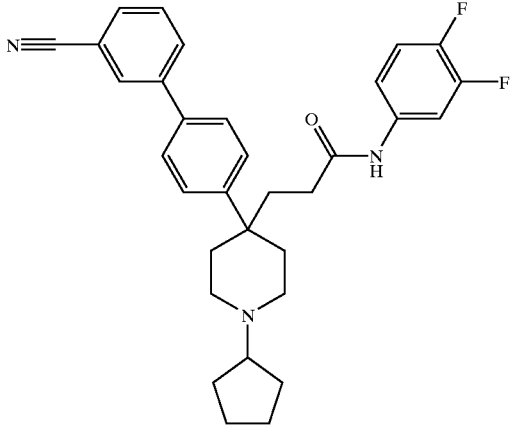 | 15 |
| 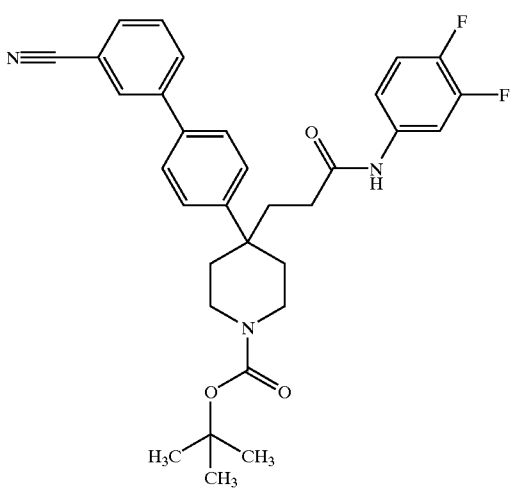 | 51 |
| 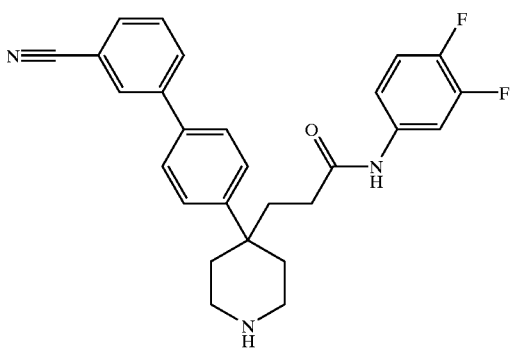 | 25 |

TABLE 1-continued
| Structure | Avg. MCH Ki (nM) |
|---|---|
| 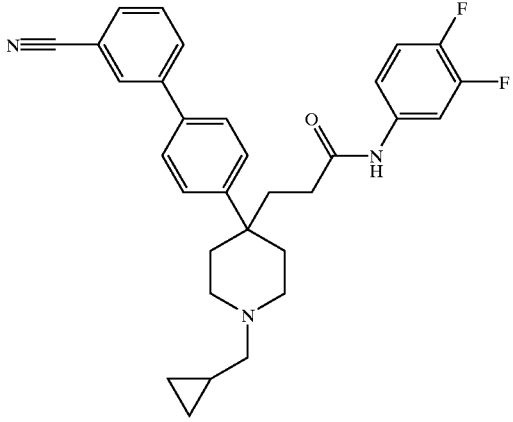 | 8 |
| 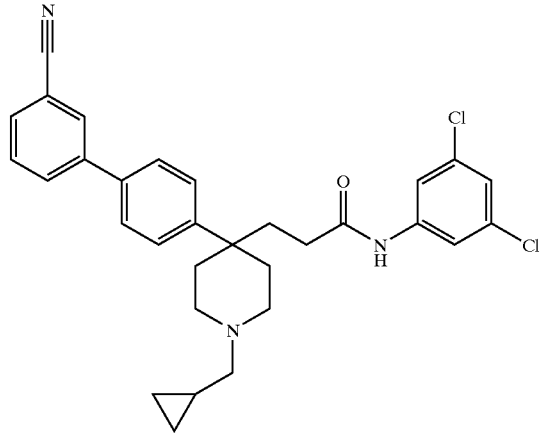 | 27 |
| 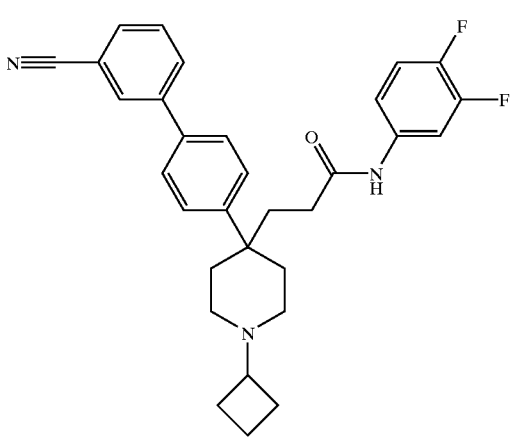 | 19 |

TABLE 1-continued
| Structure | Avg. MCH Ki (nM) |
|---|---|
| 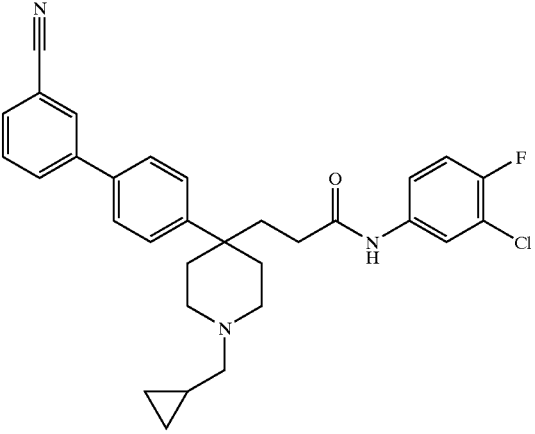 | 34 |
| 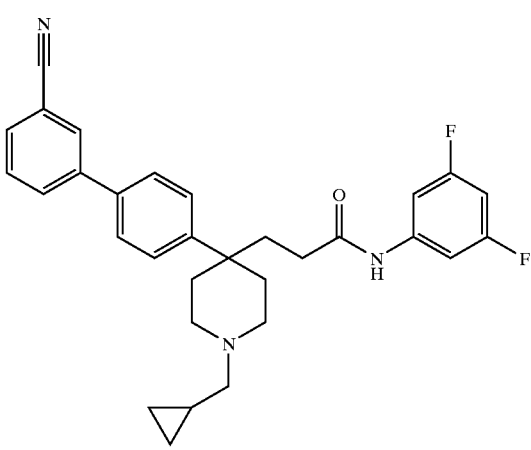 | 31 |
| 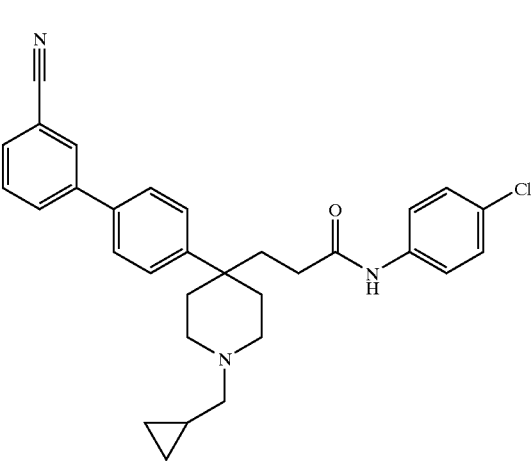 | |

TABLE 1-continued

| Structure | Avg. MCH Ki (nM) |
|---|---|
| 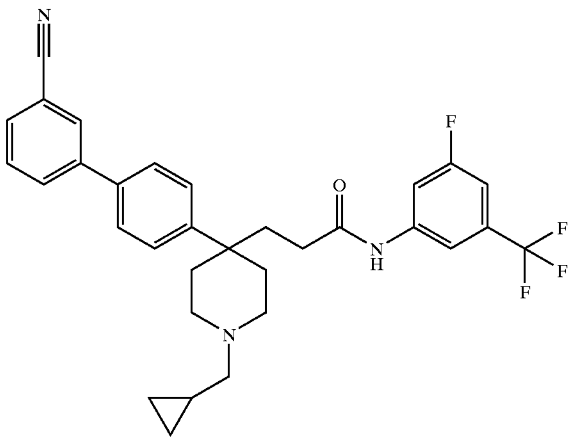 | 49 |
| 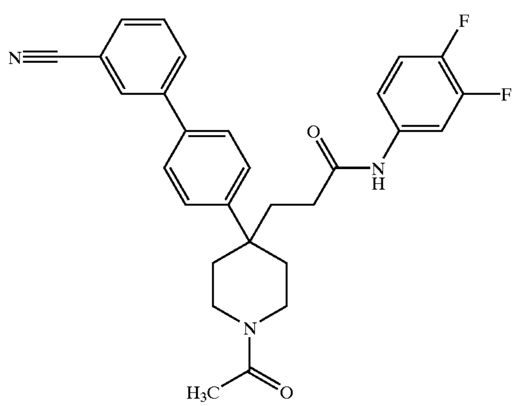 | 61 |
| | |

TABLE 1-continued

| Structure | Avg. MCH Ki (nM) |
|---|---|
| | |
| 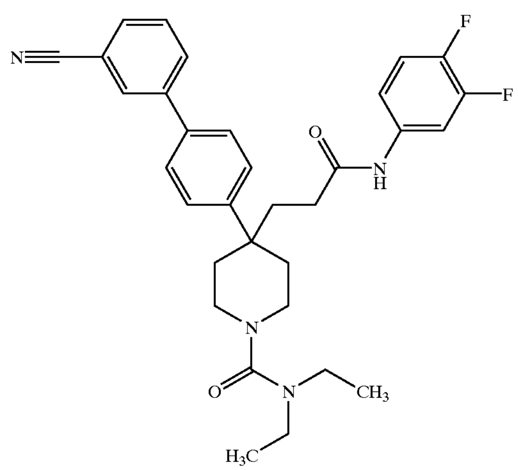 | 45 |
| | |

TABLE 1-continued
| Structure | Avg. MCH Ki (nM) |
|---|---|
| 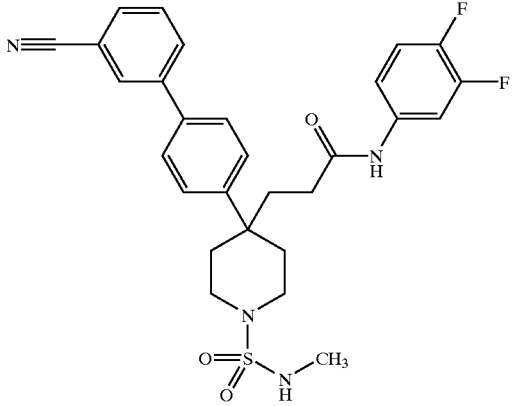 | |
| 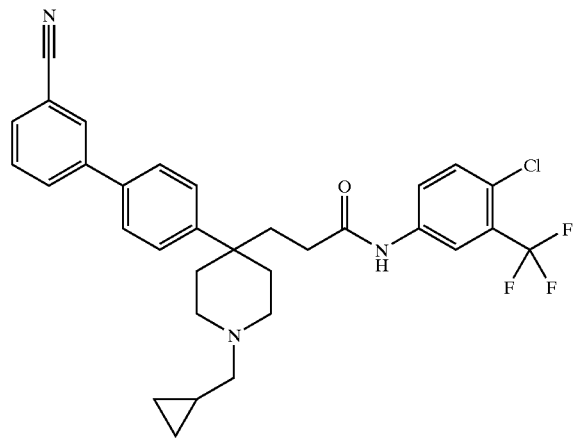 | 80 |
| 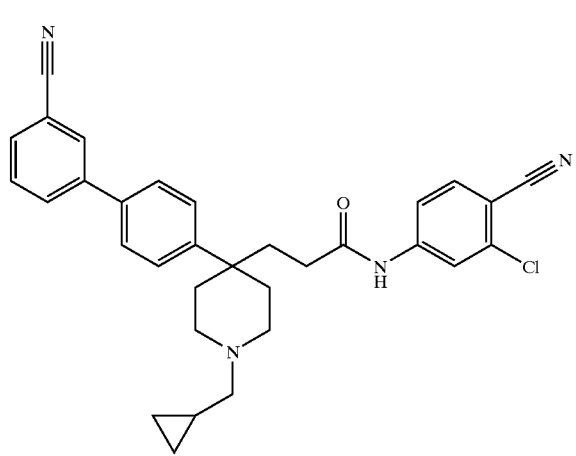 | |

TABLE 1-continued

| Structure | Avg. MCH Ki (nM) |
|---|---|
| 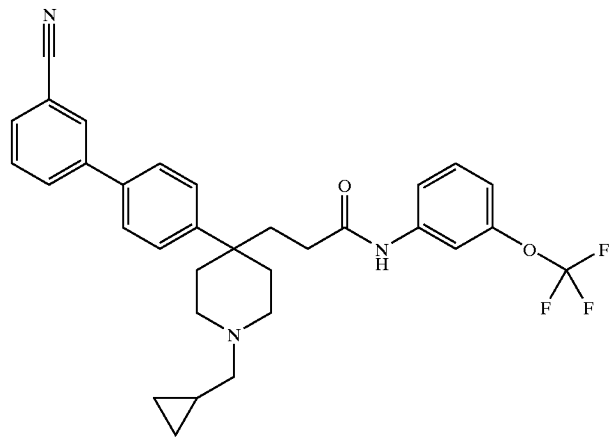 | 69 |
| | |
| | |

While the present invention has been described in conjunction with the specific embodiments set forth above, many alternatives, modifications and other variations thereof will be apparent to those of ordinary skill in the art. All such alternatives, modifications and variations are intended to fall with the spirit and scope of the present invention.

What is claimed:

1. A compound of formula I:

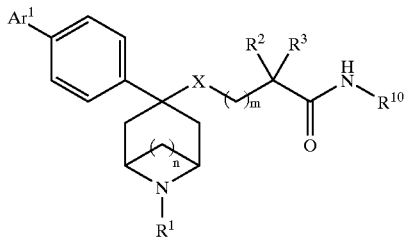

formula I or a pharmaceutically acceptable salt or solvate of said compound, wherein:

$Ar^1$ is aryl, heteroaryl, $(R^7)_p$-substituted aryl or $(R^7)_p$-substituted heteroaryl, wherein p is a number from 1 to 5 and when p is more than 1, each $R^7$ can be the same or different and each $R^7$ is hydrogen or independently selected from the group consisting of OH, alkoxy, CN, halogen, $NR^8R^9$, $C(O)NR^8R^9$, $N(R^8)C(O)R^5$, $N(R^8)S(O_2)R^5$, $S(O_2)NR^8R^9$, $C(O)OR^8$, $OCF_3$, $CF_3$, $S(O_2)R^5$ and $C(O)R^5$, or two adjacent $R^7$ can be joined together to form an alkylenedioxy selected from

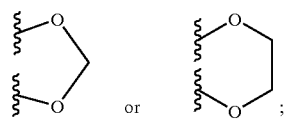

or when $Ar^1$ is an $(R^7)_p$-substituted aryl, where $R^7$ and the phenyl ring to which it is shown attached in Formula I can be bridged by Y as shown by

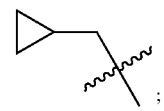

$R^1$ is H, alkyl, aryl, aralkyl, aryloxyalkyl, hydroxyalkyl, alkoxyalkyl, heteroaryl, (styrenyl)methyl, heteroaralkyl, cycloalkylalkyl, heterocyclyl, cycloalkyl, wherein each of said alkyl, aralkyl, aryloxyalkyl, hydroxyalkyl, alkoxyalkyl, heteroaralkyl, cycloalkylalkyl, heterocyclyl and cycloalkyl can be unsubstituted or optionally substituted with one or more $R^7$ moieties which can be the same or different, $-S(O_2)NR^8R^9$, $S(O_2)R^5$, $C(O)OR^8$, $C(O)R^5$, $C(O)NR^8R^9$, $(R^7)_p$-substituted aryl or $(R^7)_p$-substituted heteroaryl, wherein p is a number from 1 to 5 and when p is more than 1, each $R^7$ can be the same or different and each $R^7$ is hydrogen or independently selected from the group consisting of alkyl, cycloalkyl, OH, alkoxy, CN, halogen, heteroaryl, OC(O)OH; aryloxy, $NR^8R^9$, $C(O)NR^8R^9$, $N(R^8)C(O)R^5$, $N(R^8)S(O_2)R^5$, $S(O_2)NR^8R^9$, $C(O)OR^8$, $OCF_3$, $CF_3$, $SR^5$, $S(O_2)R^5$ and $C(O)R^5$, or two adjacent $R^7$ can be joined together to form an alkylenedioxy selected from

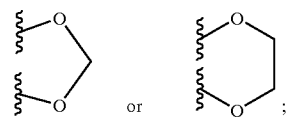

$R^2$, $R^3$, $R^8$ and $R^9$ can each be the same or different and each independently H or alkyl;

or $R^2$ and $R^3$ together are alkylene and with the carbon to which they are attached form a 3 to 7 membered ring;

$R^4$ is H, alkyl, aralkyl, $R^5C(O)$, $R^5S(O_2)$ or

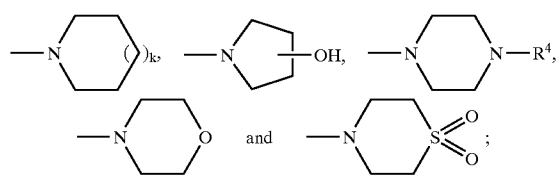

$R^5$ is alkyl or aryl;

$R^6$ is alkyl, aralkyl or $(R^7)_p$-substituted aralkyl, wherein p is a number from 1 to 5 and when p is more than 1, each $R^7$ can be the same or different and each $R^7$ is hydrogen or independently selected from the group consisting of OH, alkoxy, CN, halogen, $NR^8R^9$, $C(O)NR^8R^9$, $N(R^8)C(O)R^5$, $N(R^8)S(O_2)R^5$, $-S(O_2)NR^8R^9$, $C(O)OR^8$, $OCF_3$, $CF_3$, $S(O_2)R^5$ and $C(O)R^5$, $R^{10}$ is aryl, heteroaryl, $(R^7)_p$-substituted aryl or $(R^7)_p$-substituted heteroaryl, wherein p is a number from 1 to 5 and when p is more than 1, each $R^7$ can be the same or different and each $R^7$ is hydrogen or independently selected from the group consisting of OH, alkoxy, CN, halogen, $NR^8R^9$, $C(O)NR^8R^9$, $N(R^8)C(O)R^5$, $N(R^8)S(O_2)R^5$, $S(O_2)NR^8R^9$, $C(O)OR^8$, $OCF_3$, $CF_3$, $S(O_2)R^5$, $C(O)R^5$ and heterocycloalkyl or $R^{10}$ is an alkylene or heteroalkylene where said alkylene or heteroalkylene is attached to the N of $NR^{10}$ to form a heterocyclyl ring selected from the group consisting of X is $N(R^4)$, O, S, S→O, $S(O_2)$, C(O) or $CH_2$;

Y is O, $CH_2$, C(O), N(H), $N(R^6)$ or S;

k is 0, 1 or 2;

m is 0, 1 or 2;

n is 0 or 2; and wherein each of said alkyl, alkylene, heteroalkylene, aryl, aralkyl, alkoxy, aryloxy, aryloxyalkyl, hydroxyalkyl, alkoxyalkyl, heterocyclyl, heterocycloalkyl, heteroaryl, heteroaralkyl, cycloalkylalkyl, heterocyclyl and cycloalkyl can be unsubstituted or optionally substituted with one or more $R^7$ moieties which can be the same or different.

2. The compound of claim 1 of formula Ia:

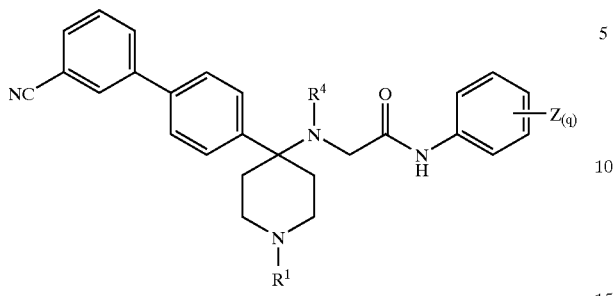

formula Ia or a pharmaceutically acceptable salt or solvate of said compound, wherein:

q is 1 or 2;
$R^1$ is H, alkyl or cycloalkyl;
$R^4$ is H or alkyl; and
Z is 1 or 2 substituents which can be the same or different and independently selected from the group consisting of halogen, $CF_3$ and $OCF_3$.

3. The compound of claim 1 of formula Ib:

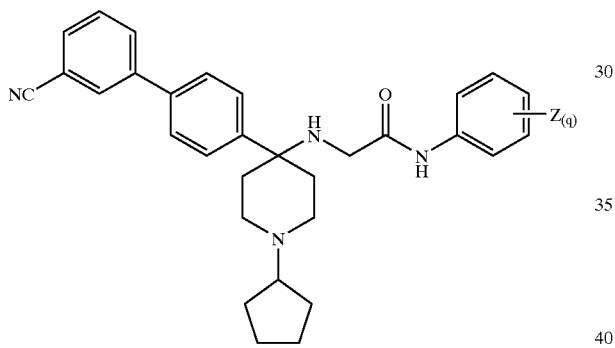

formula Ib or a pharmaceutically acceptable salt or solvate of said compound, wherein:

q is 1 or 2;
Z is 1 or 2 substituents which can be the same or different and independently selected from the group consisting of halogen, $CF_3$ and $OCF_3$.

4. The compound of claim 1 of formula Ic:

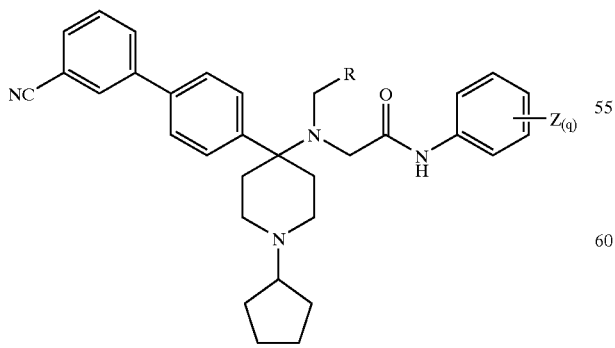

formula Ic or a pharmaceutically acceptable salt or solvate of said compound, wherein:

q is 1 or 2;
R is H, alkyl or cycloalkyl; and
Z is 1 or 2 substituents which can be the same or different and independently selected from the group consisting of halogen, $CF_3$ and $OCF_3$.

5. The compound of claim 1 of formula Id:

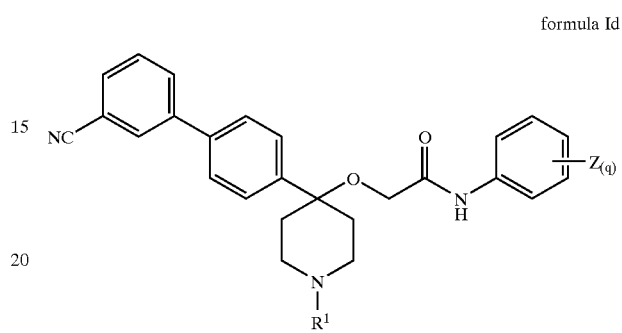

formula Id or a pharmaceutically acceptable salt or solvate of said compound, wherein:

q is 1 or 2;
$R^1$ is independently selected from the group consisting of H, alkyl and cycloalkyl; and
Z is 1 or 2 substituents which can be the same or different and independently selected from the group consisting of halogen, $CF_3$ and $OCF_3$.

6. The compound of claim 1 of formula Ie:

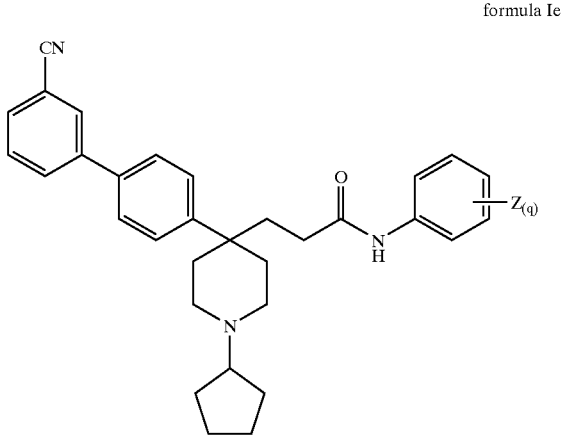

formula Ie or a pharmaceutically acceptable salt or solvate of said compound, wherein:

q is 1 or 2;
Z is independently selected from the group consisting of Cl, $CF_3$ and F.

7. The compound of claim 1 of formula If:
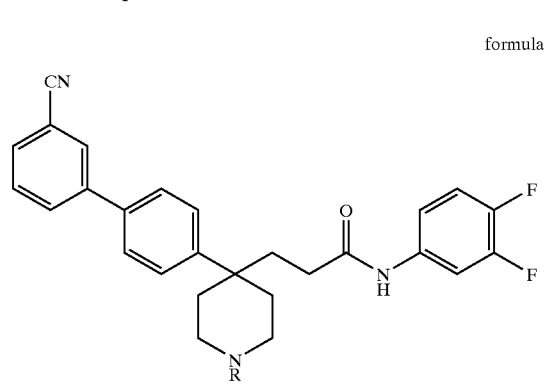
formula If
or a pharmaceutically acceptable salt or solvate of said compound, wherein
R is selected from the group consisting of $CH_3C(O)$, $CH_3S(O_2)$, $CH_3CH_2OC(O)$, $(CH_3CH_2)_2NC(O)$, $(CH_3)_2NS(O_2)$, $CH_3CH_2NHS(O_2)$ and cyclopropylmethyl.
8. The compound of claim 1 selected from the group consisting of
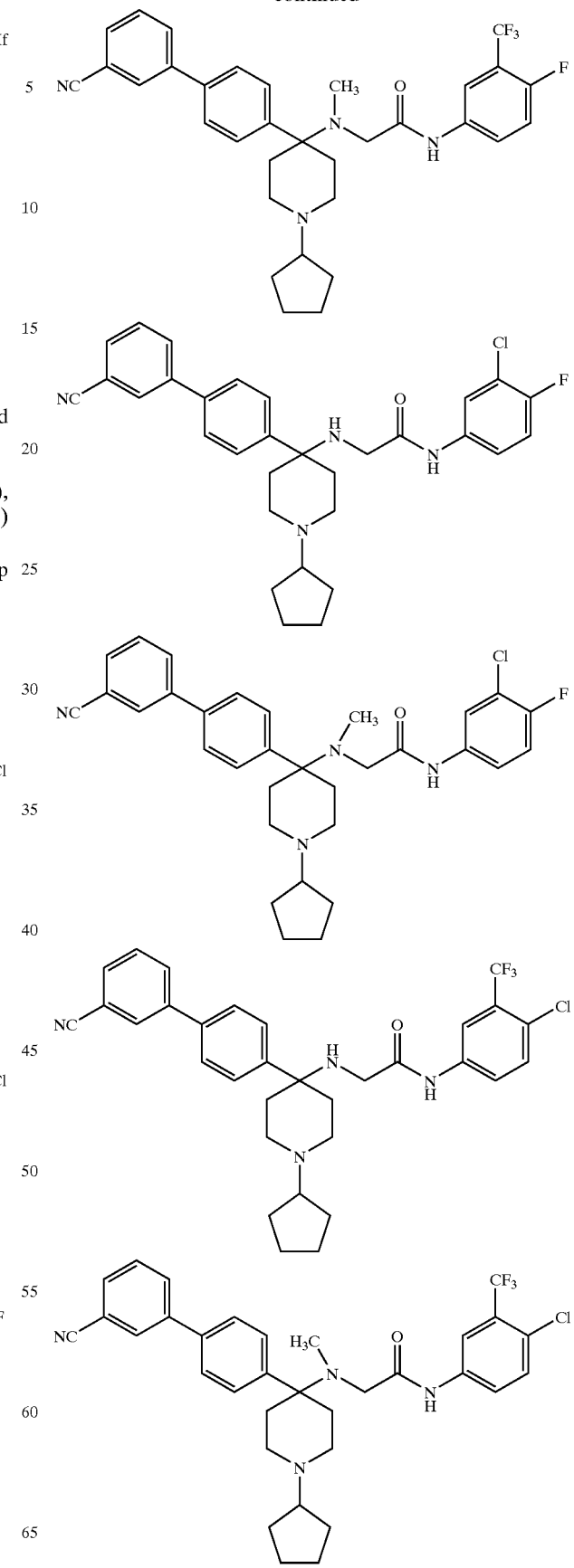

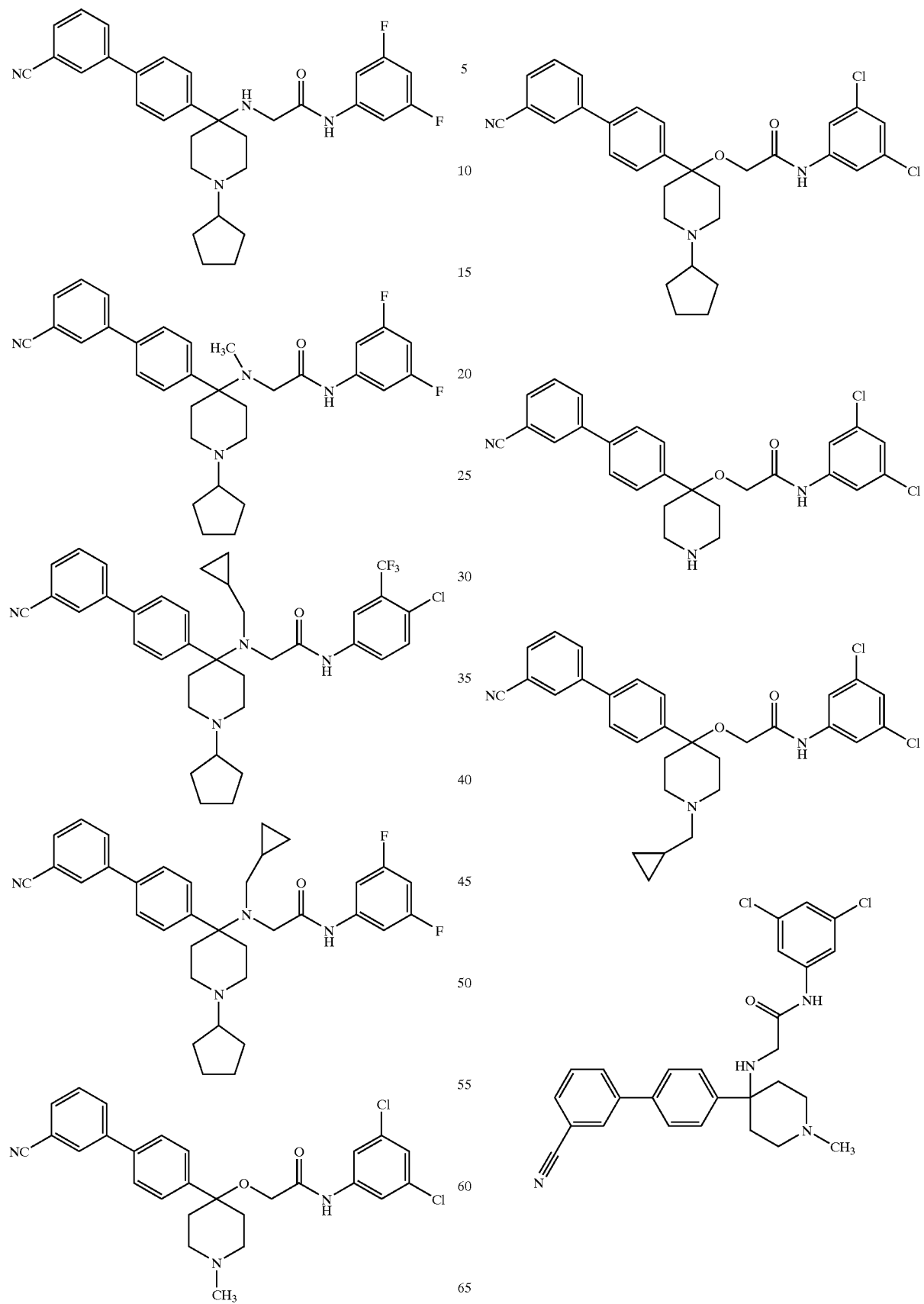

-continued
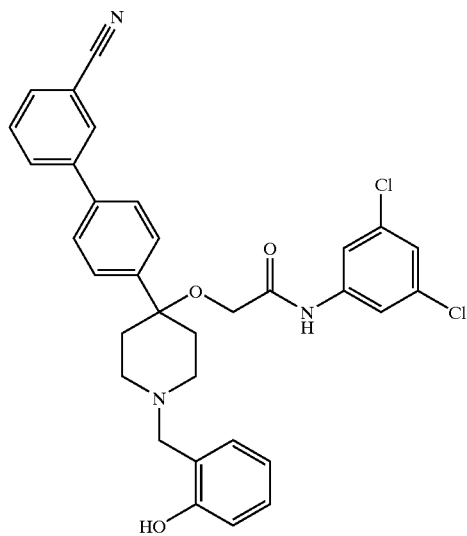
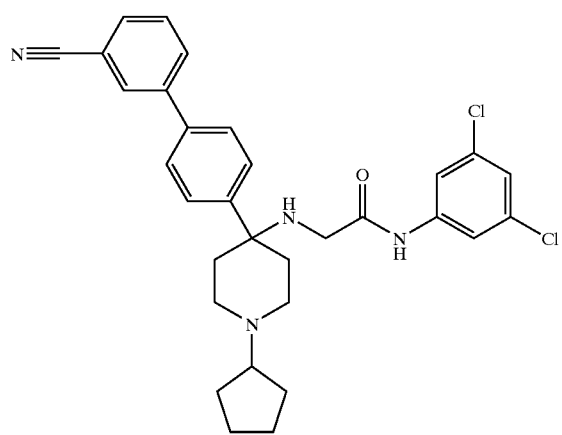
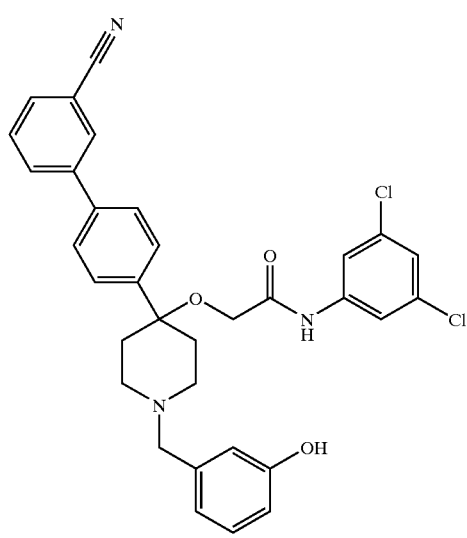
-continued
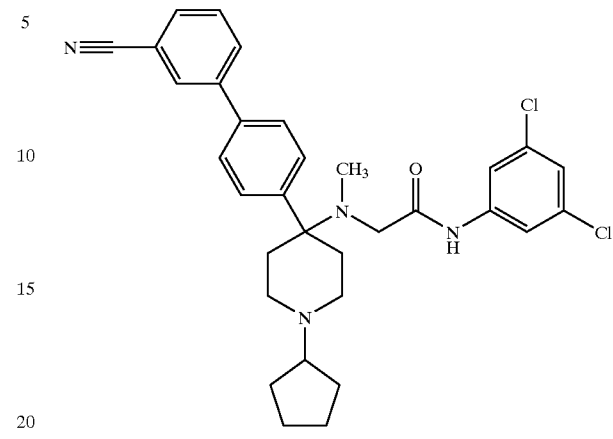
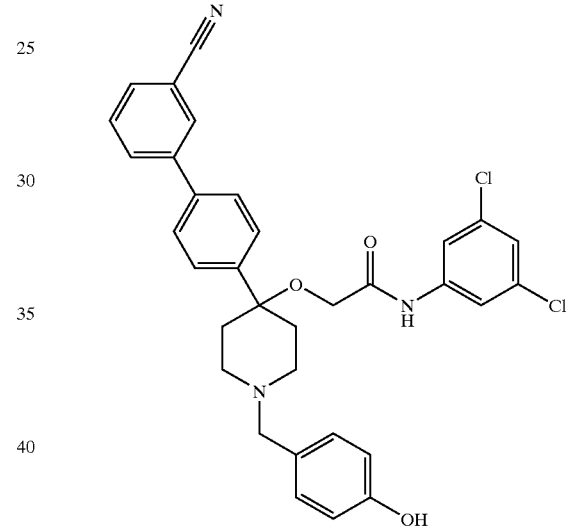
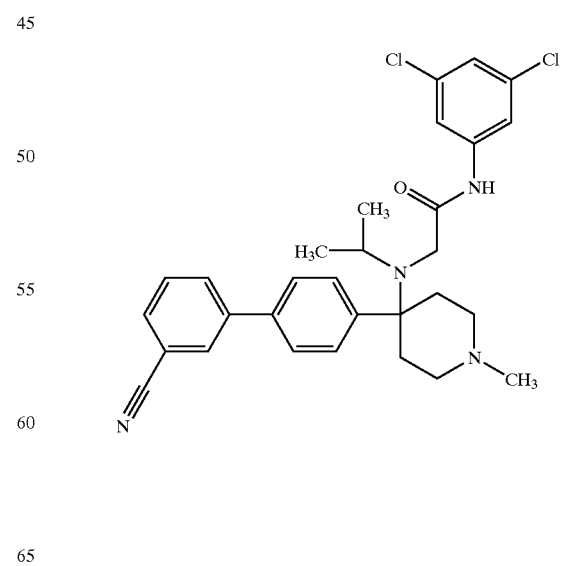

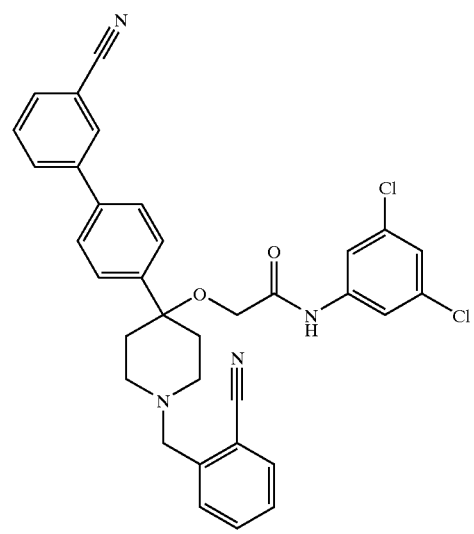
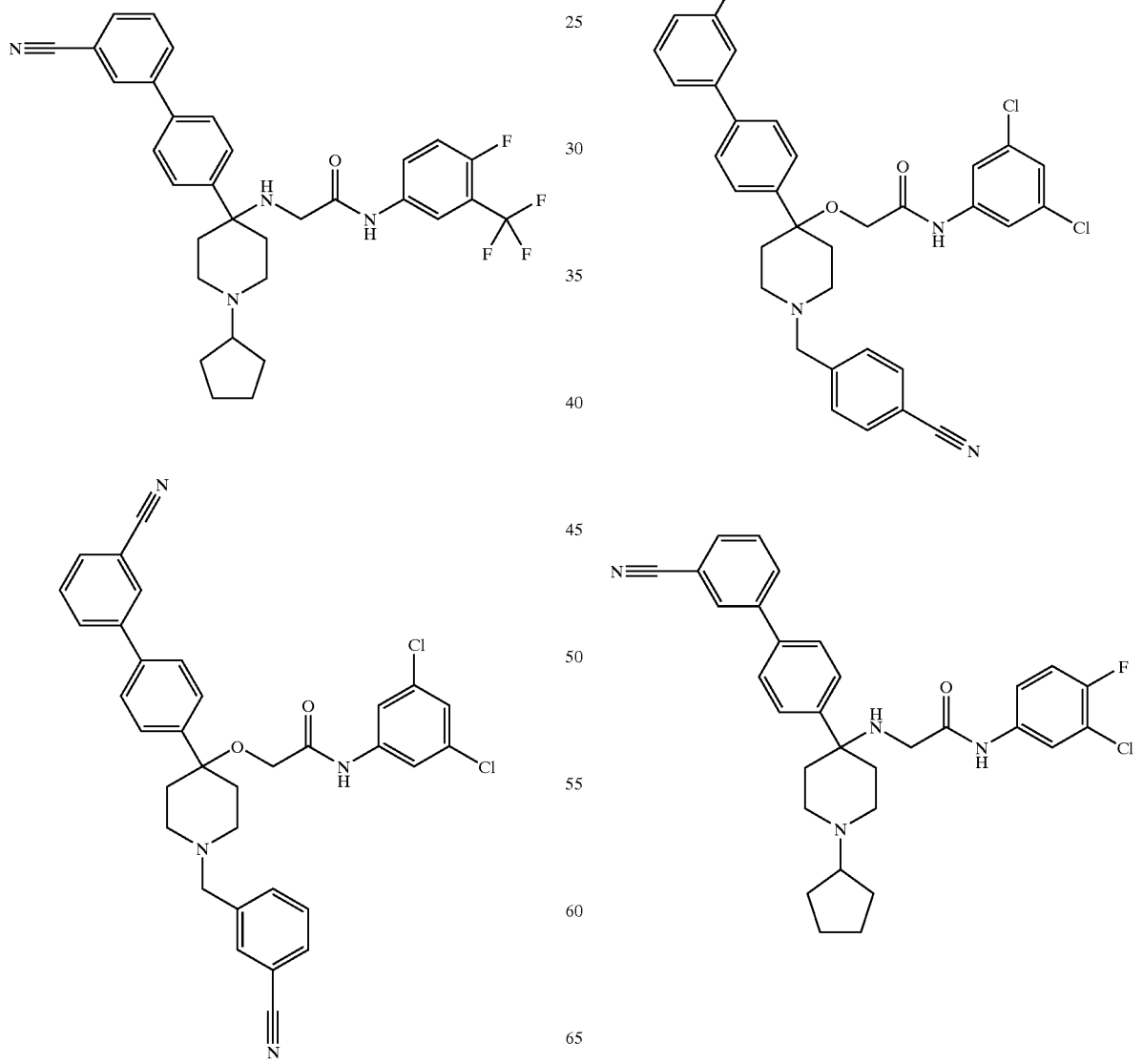

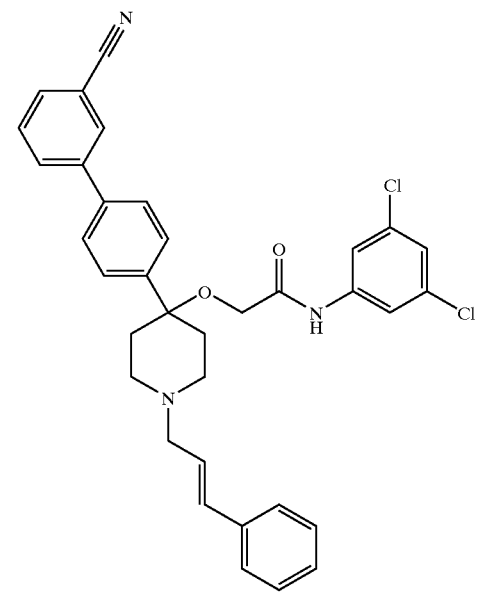
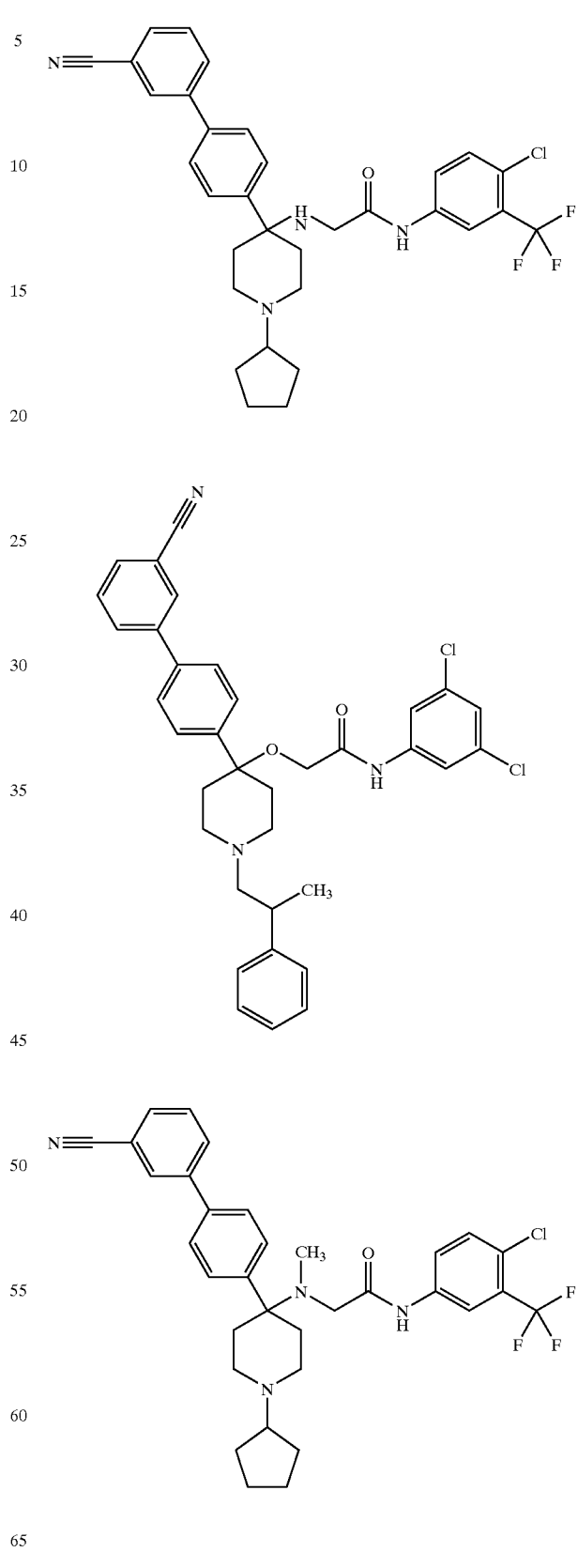

175
-continued
176
-continued
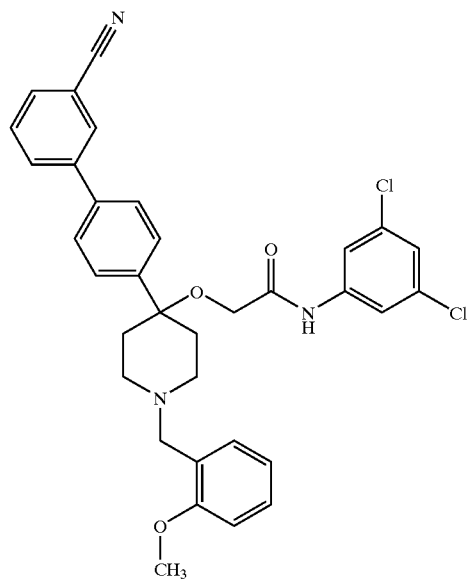
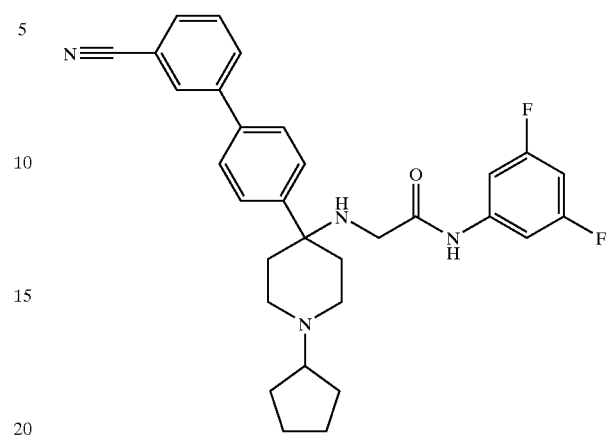
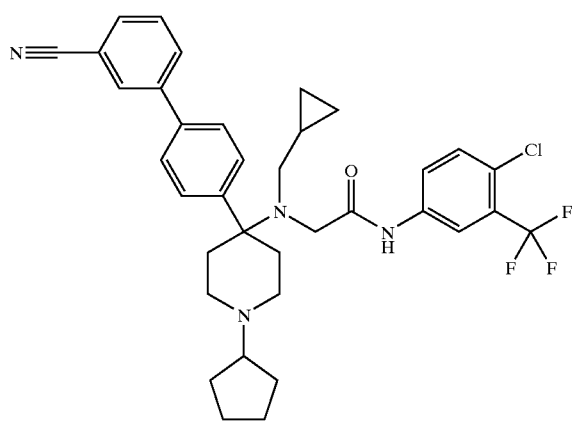
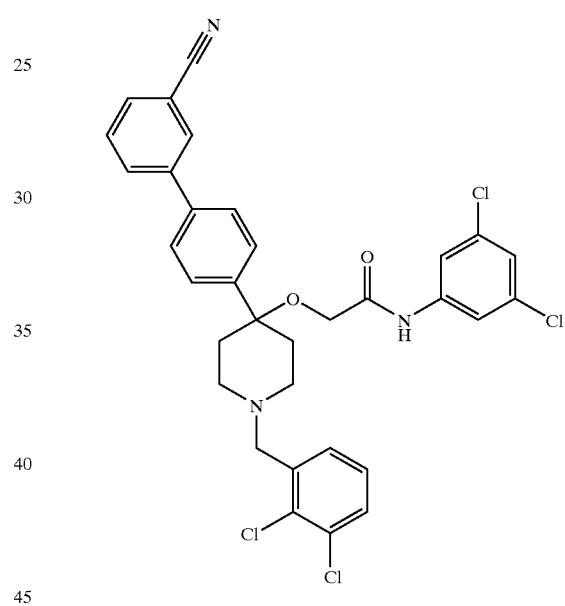
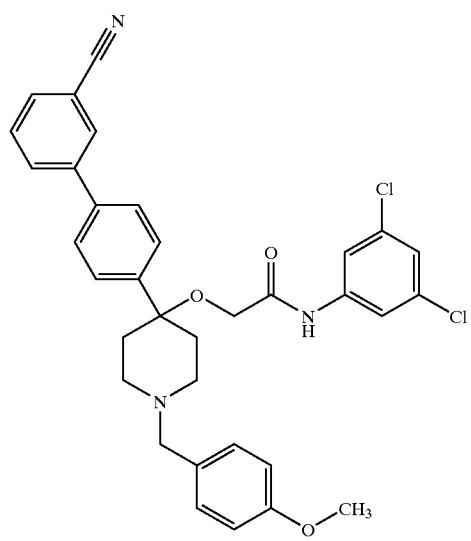

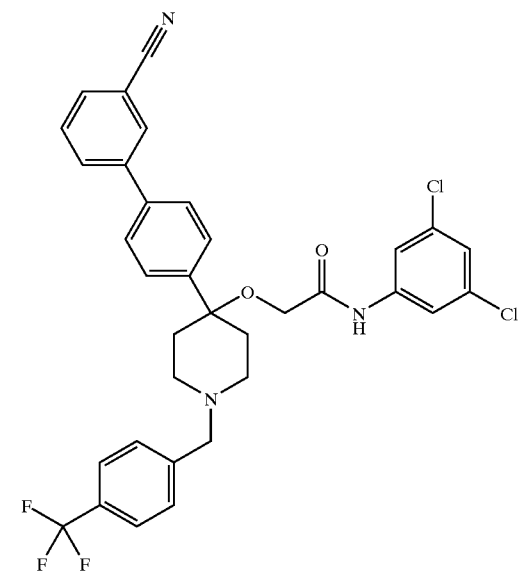
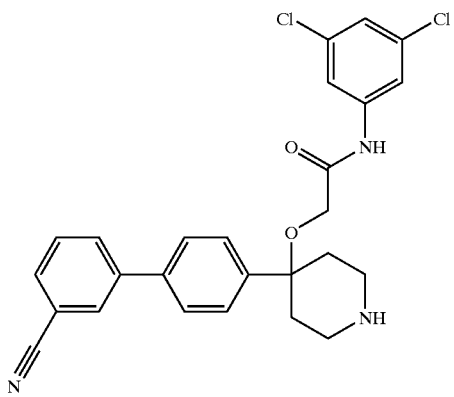
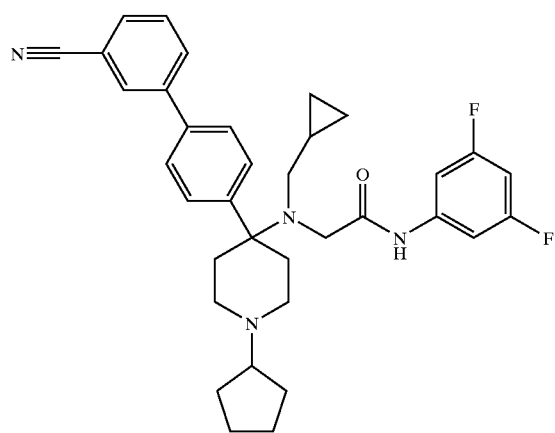
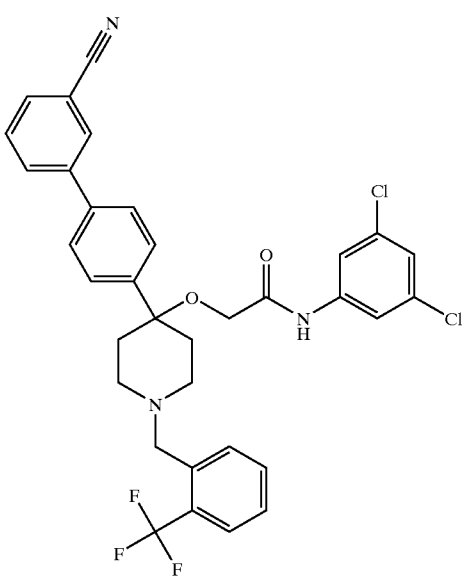
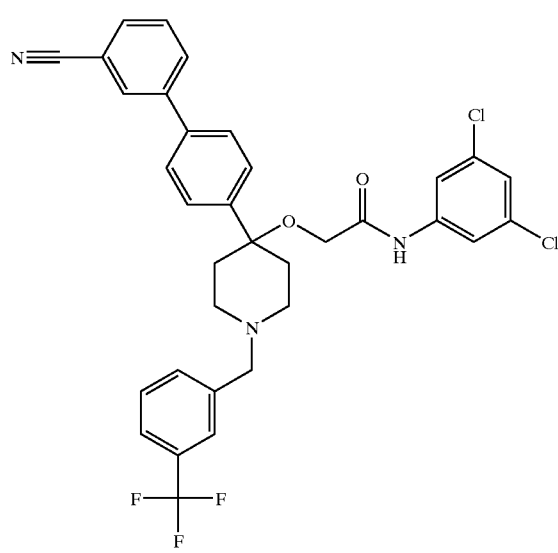
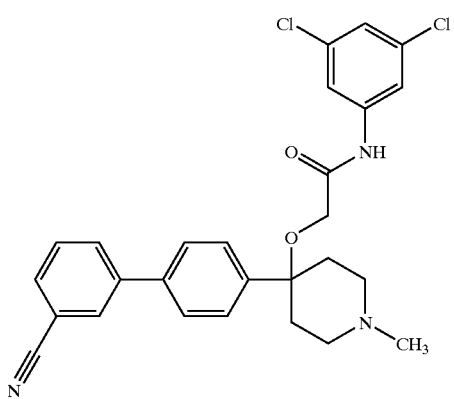

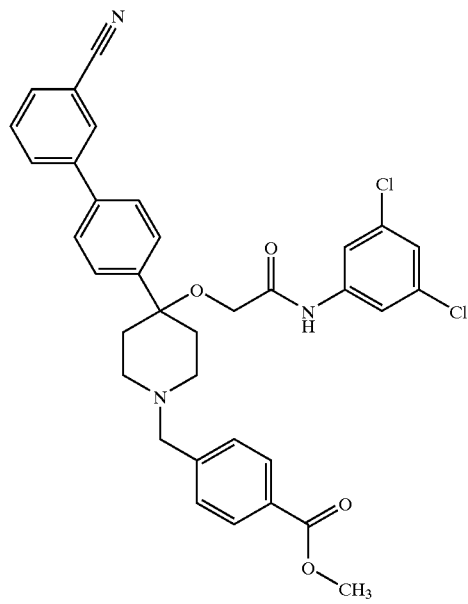
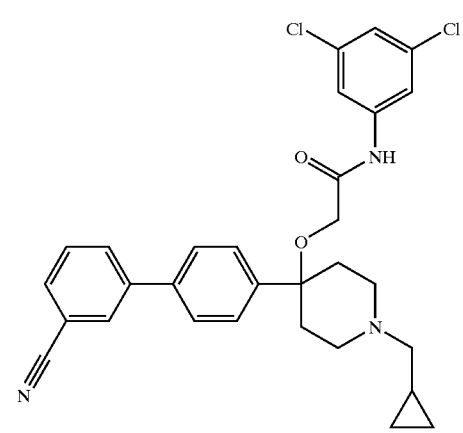
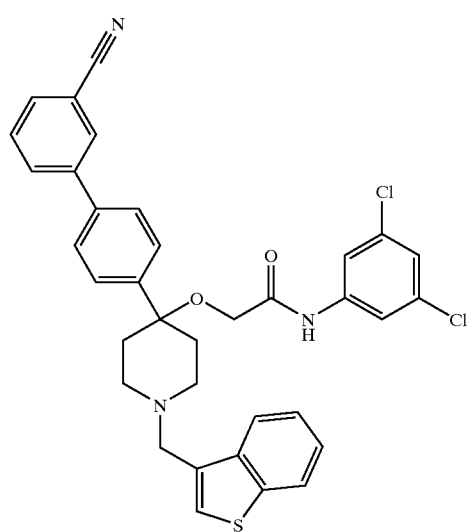
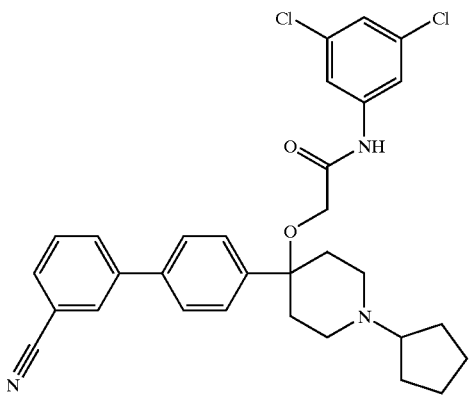
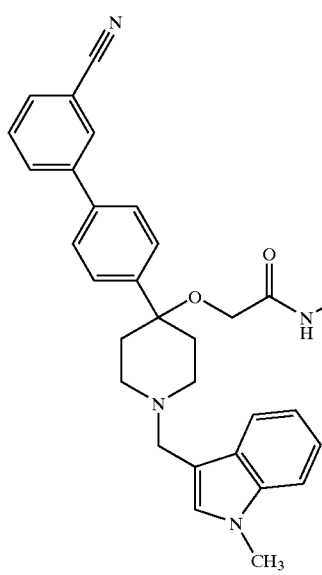
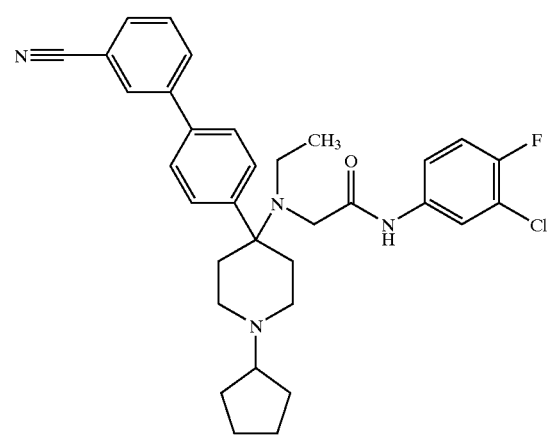

181
-continued
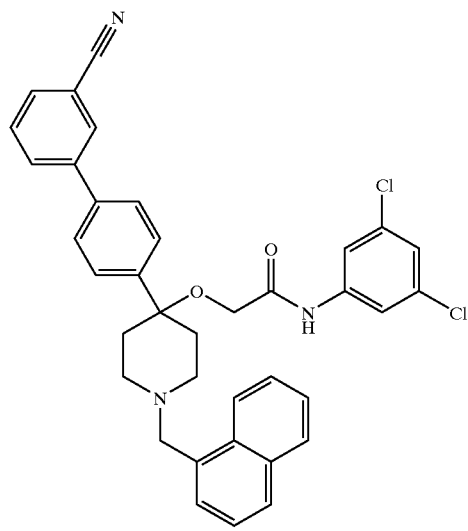
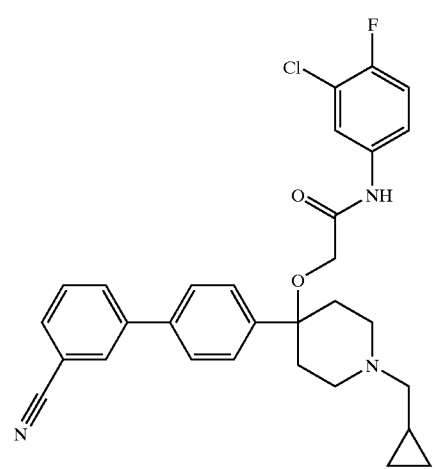
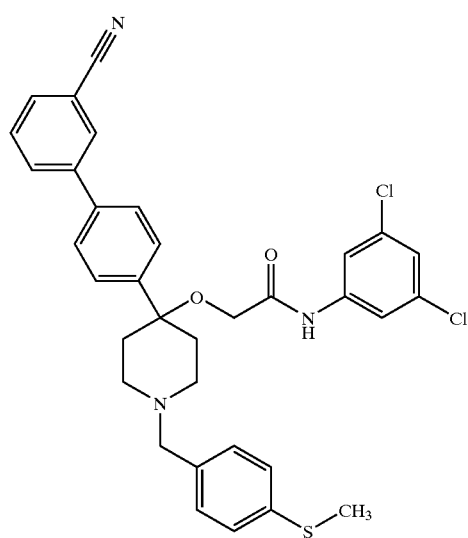
182
-continued
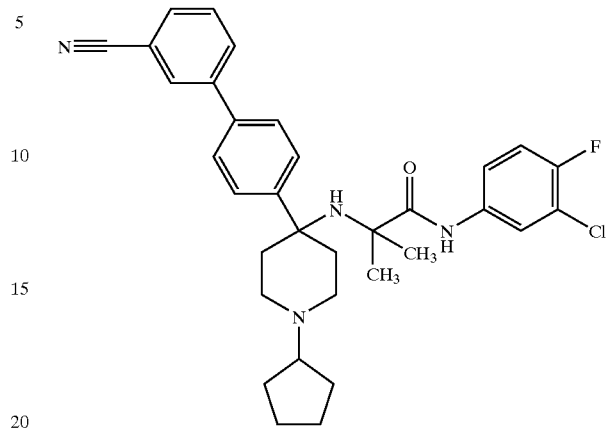
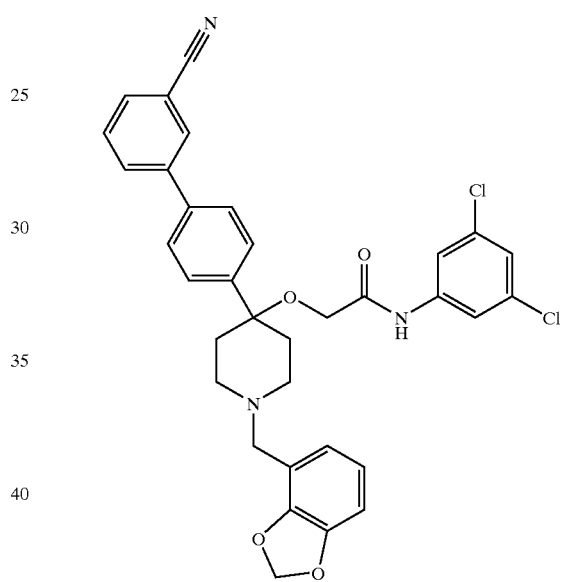
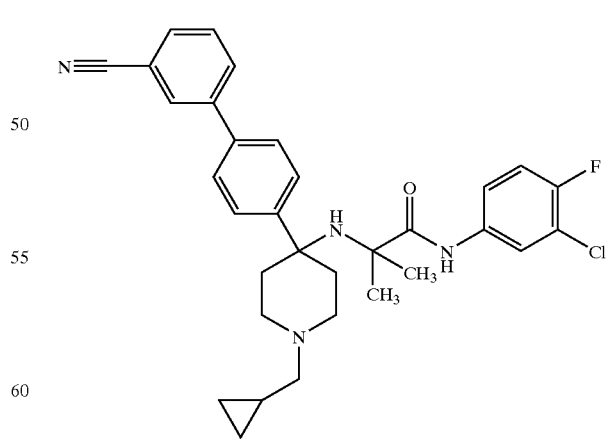

-continued
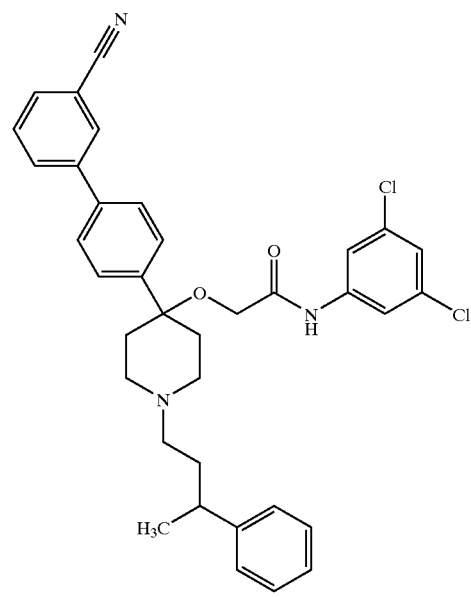
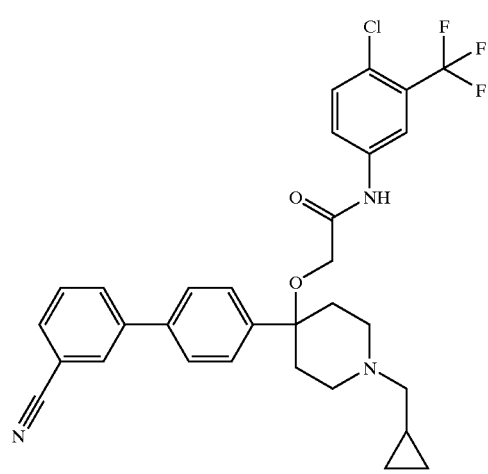
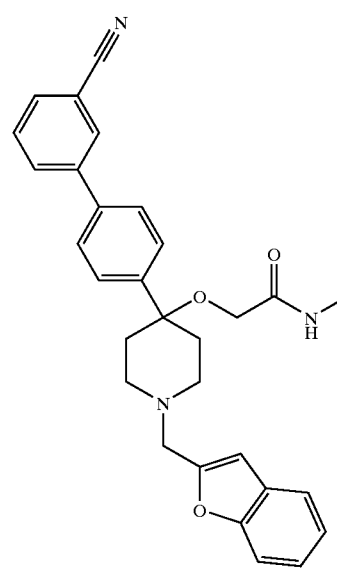
-continued
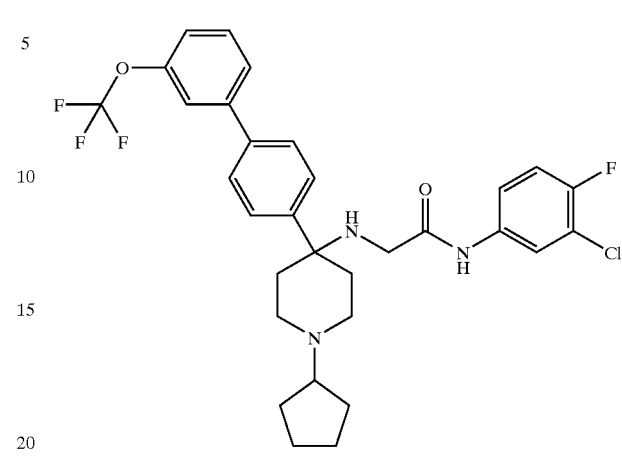
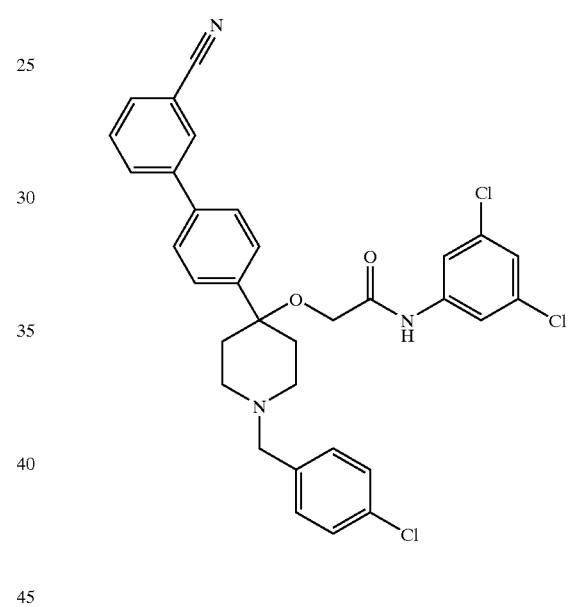
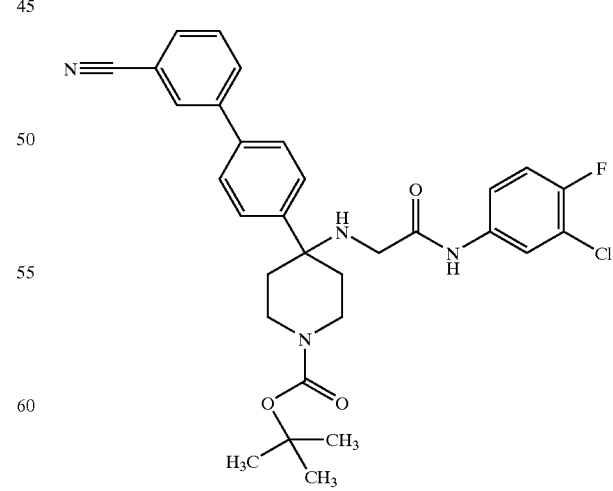

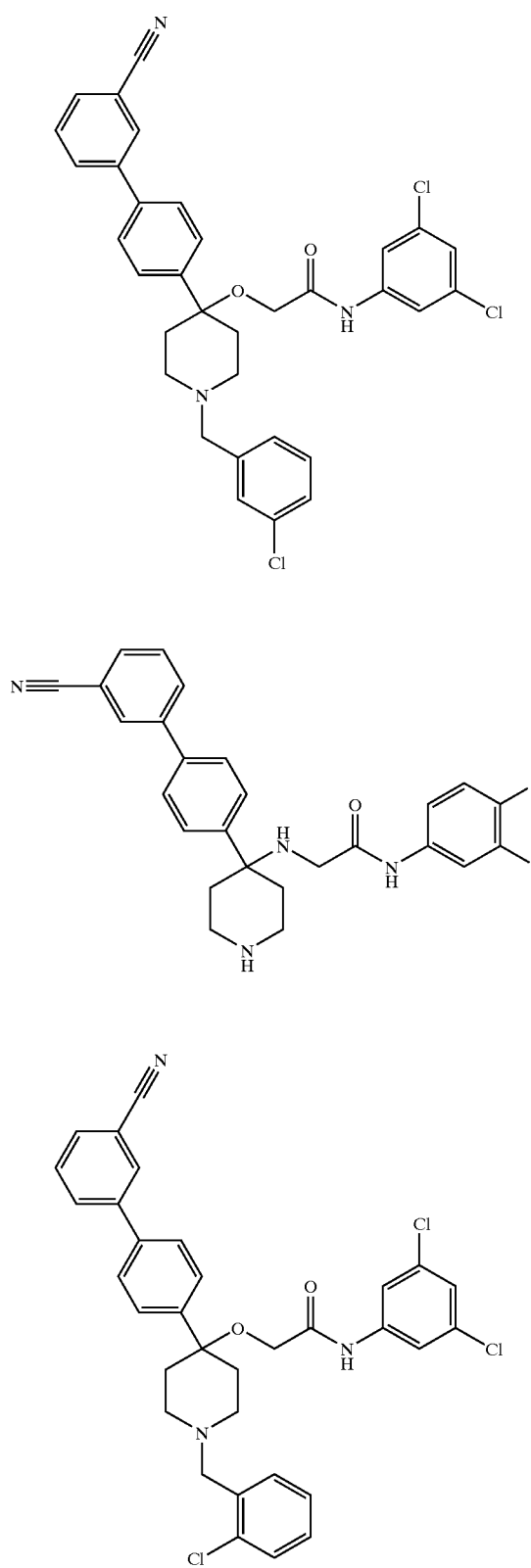
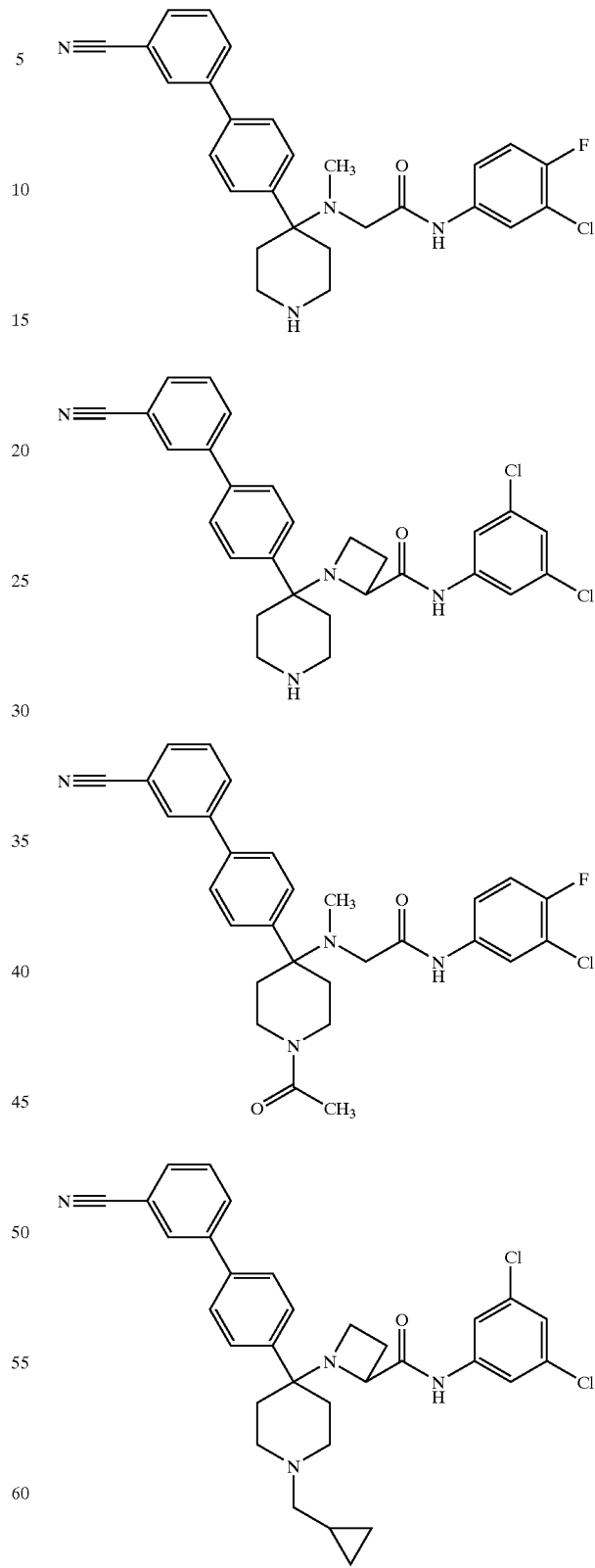

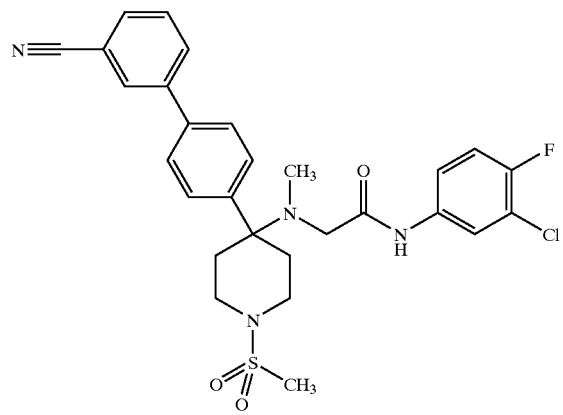
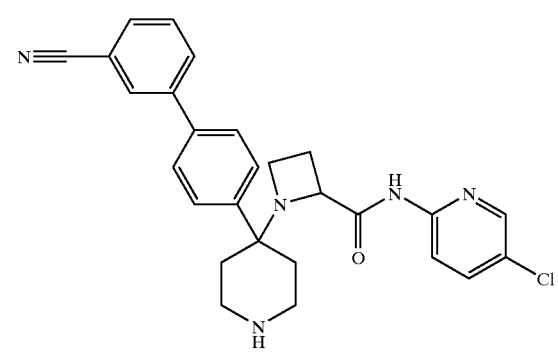
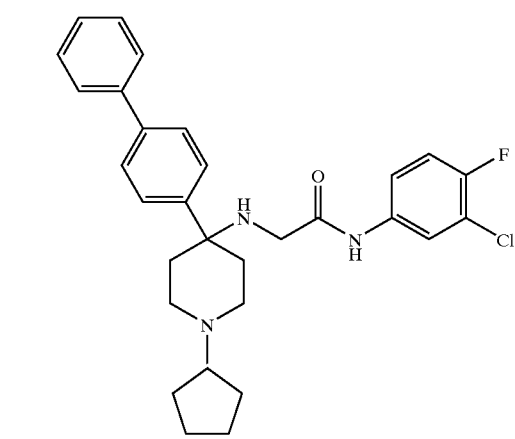
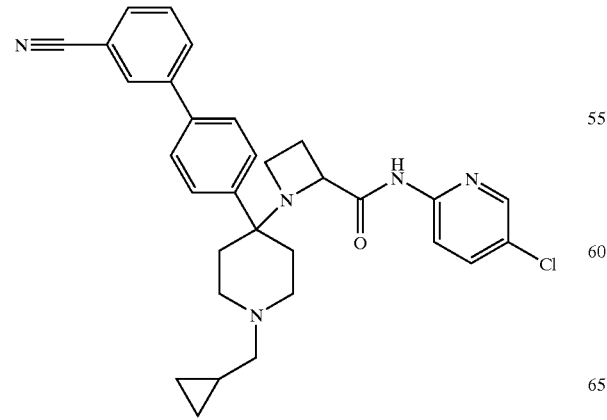
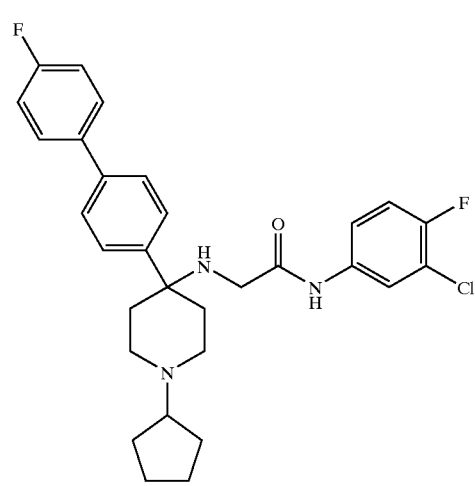
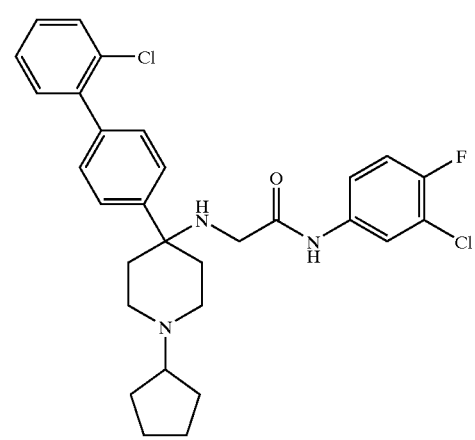
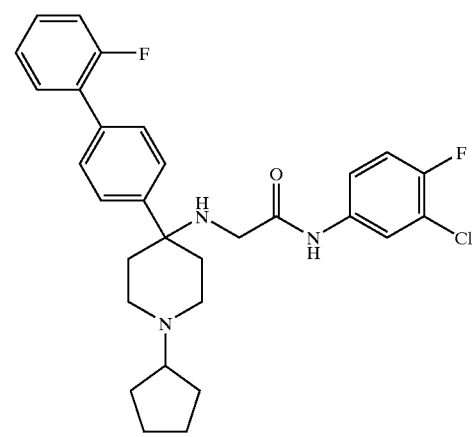

189
-continued
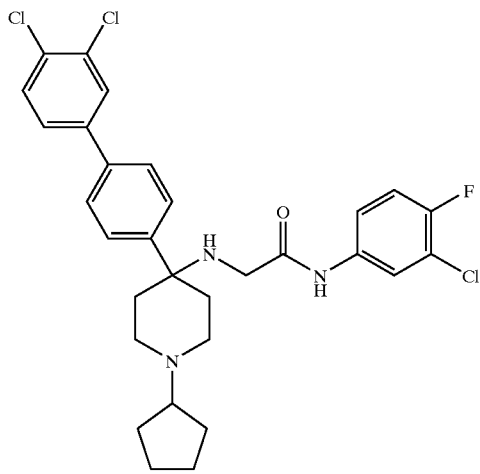
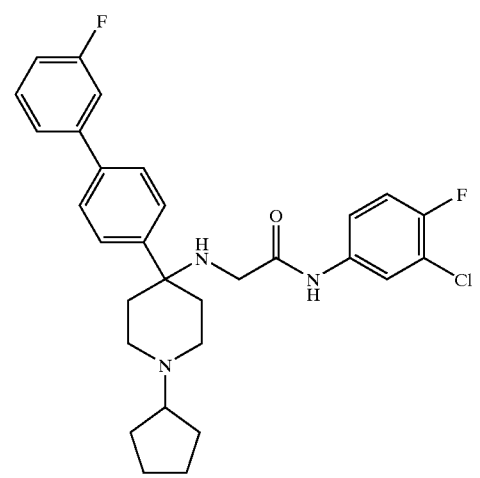
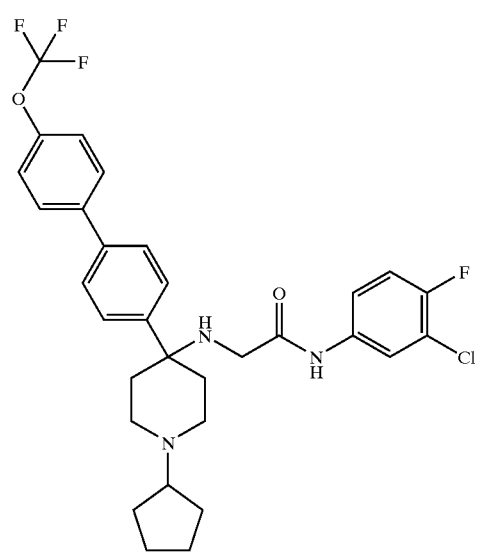
190
-continued
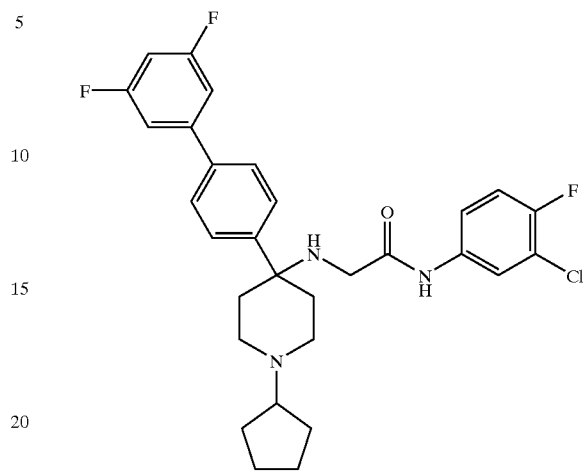
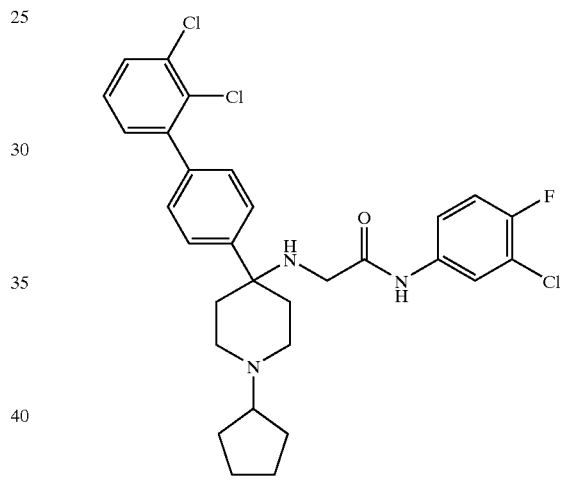
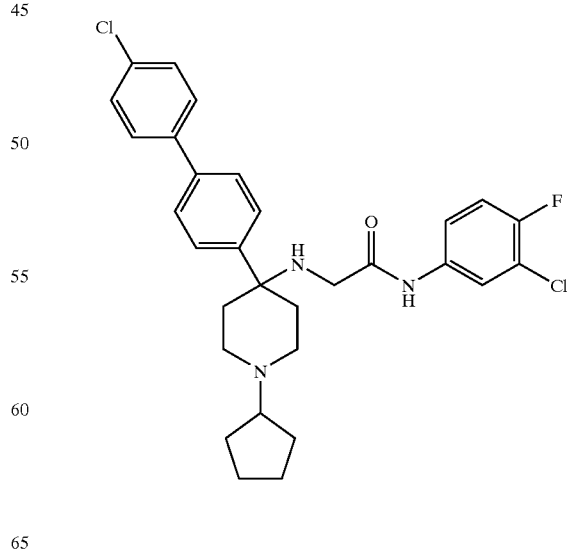

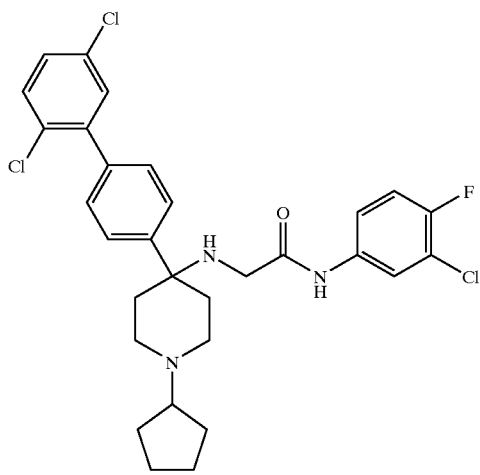
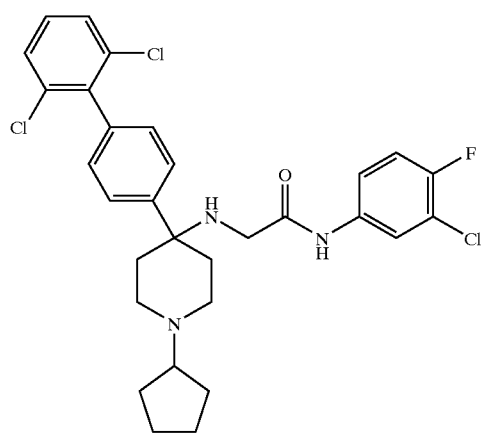
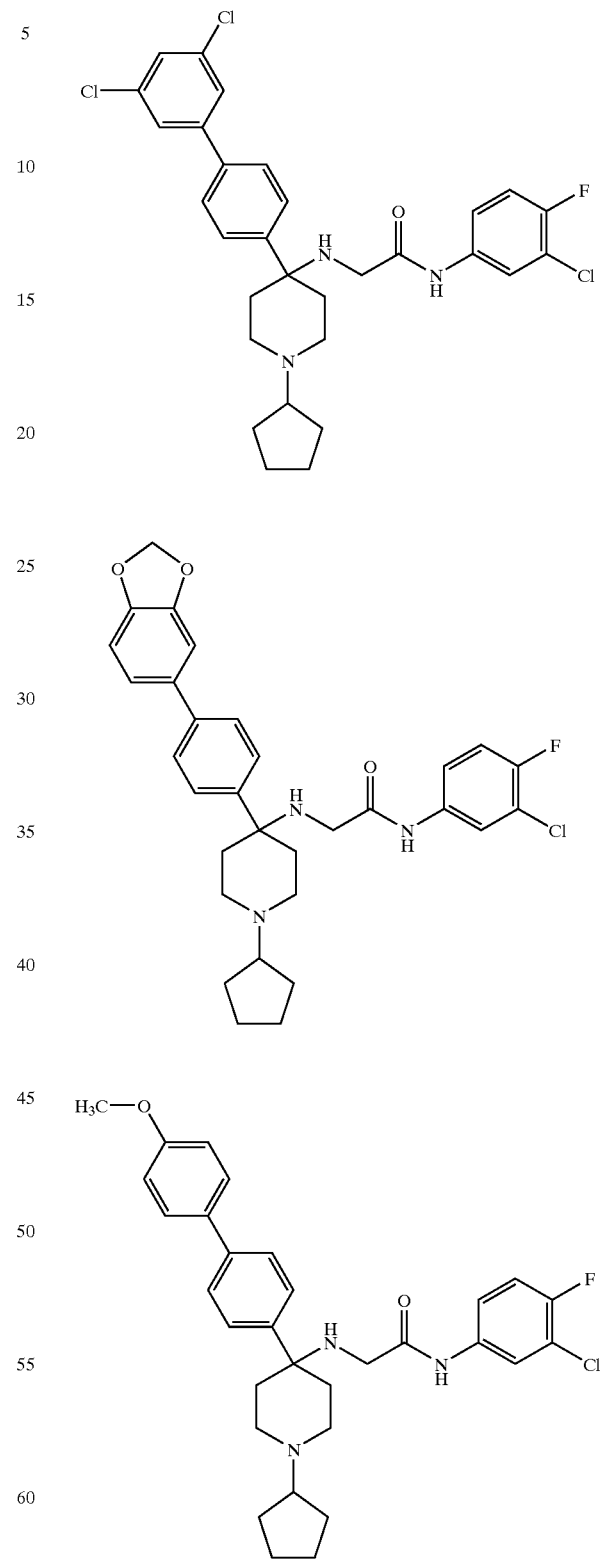

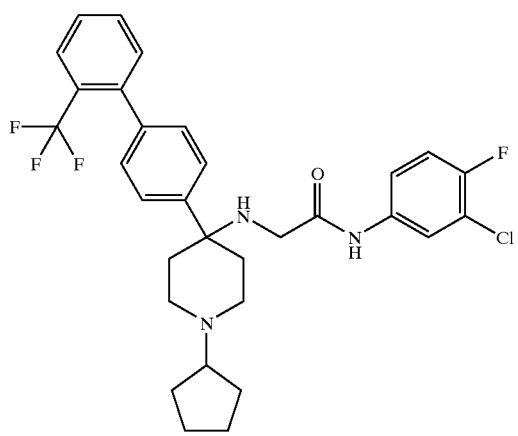
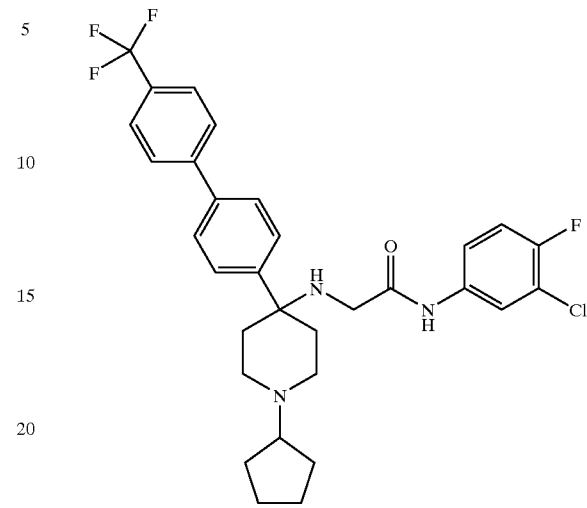
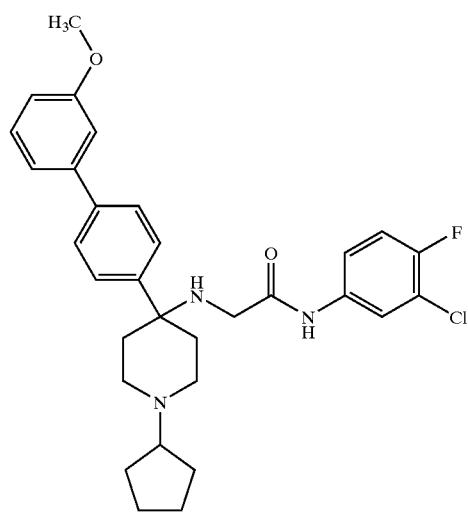
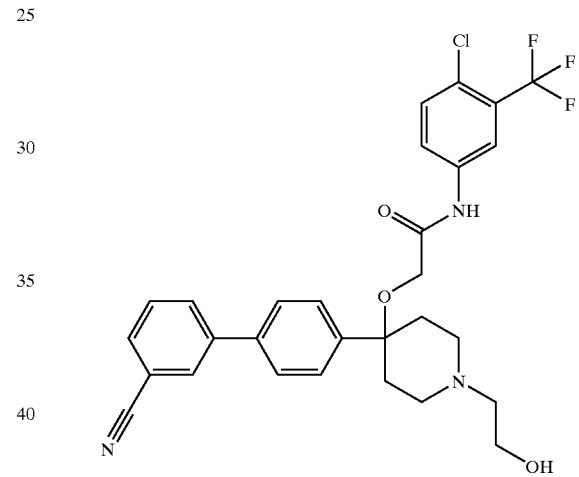
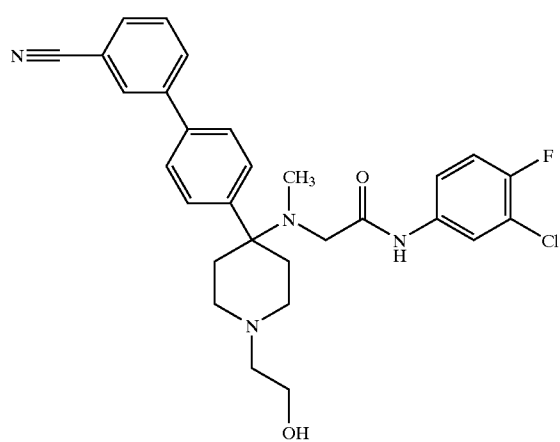
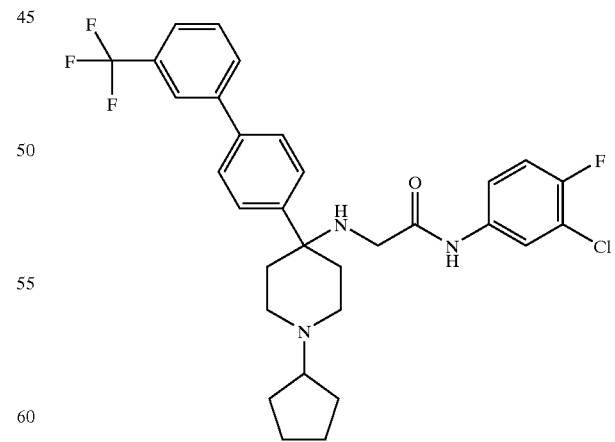

195
-continued
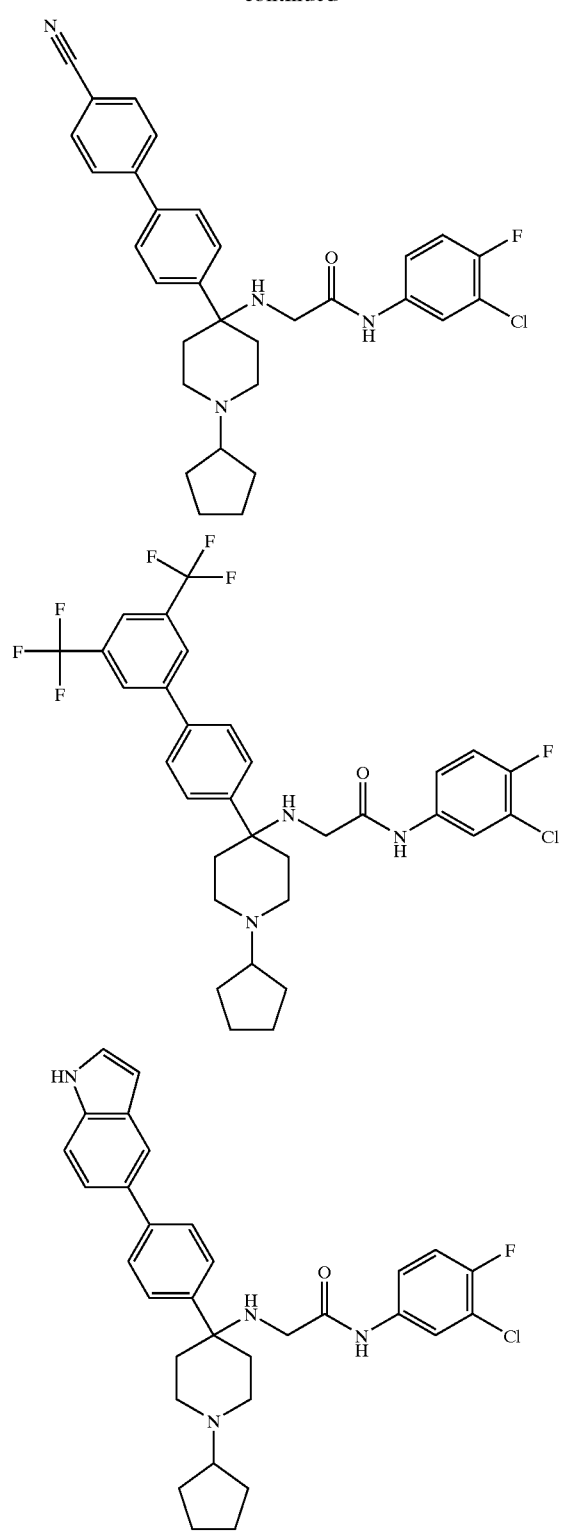
196
-continued
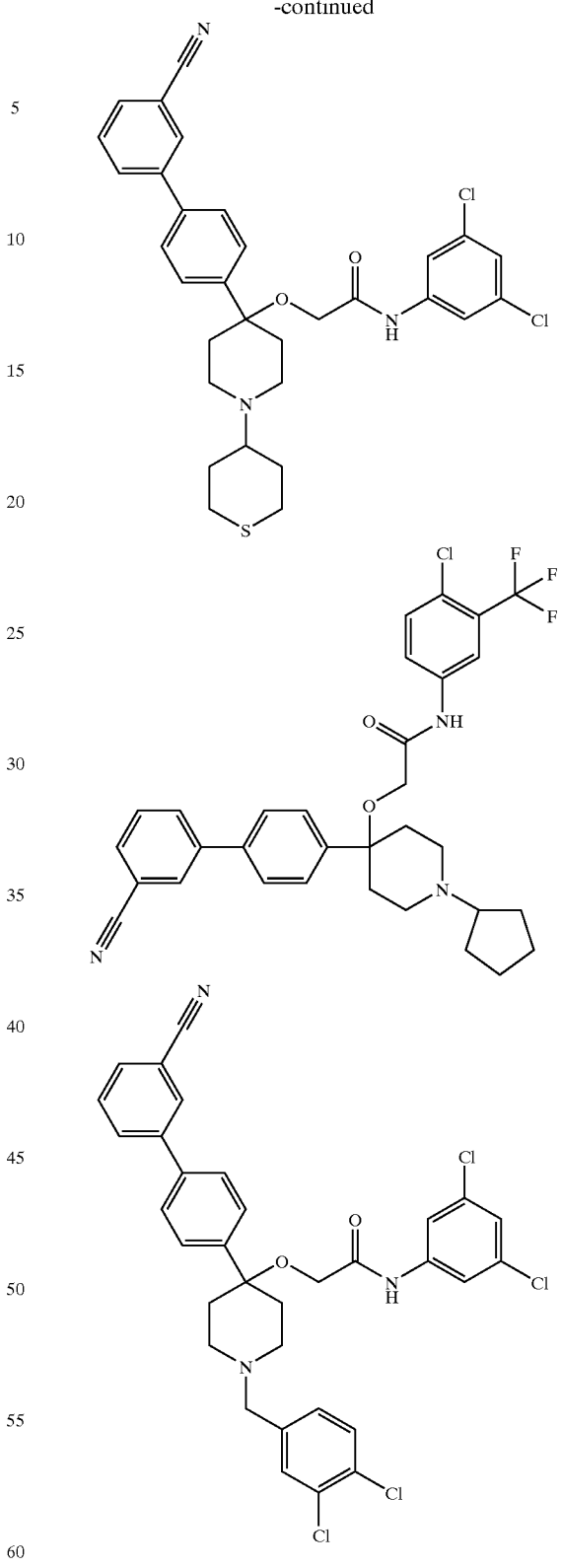

197
-continued
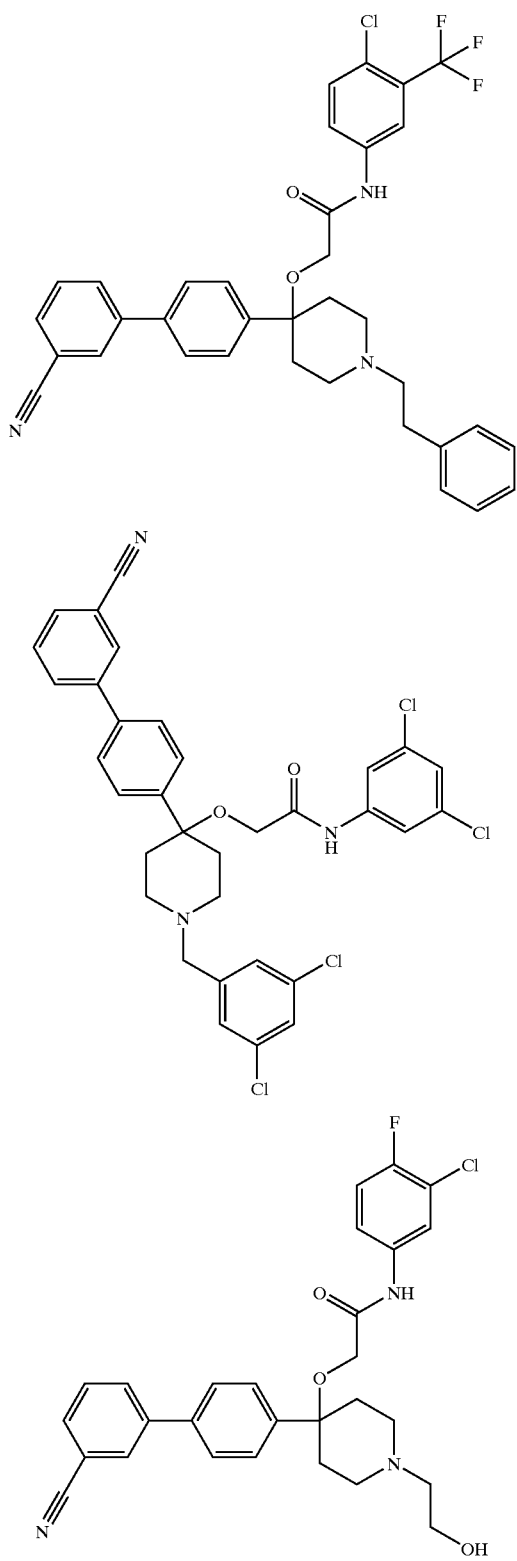
198
-continued
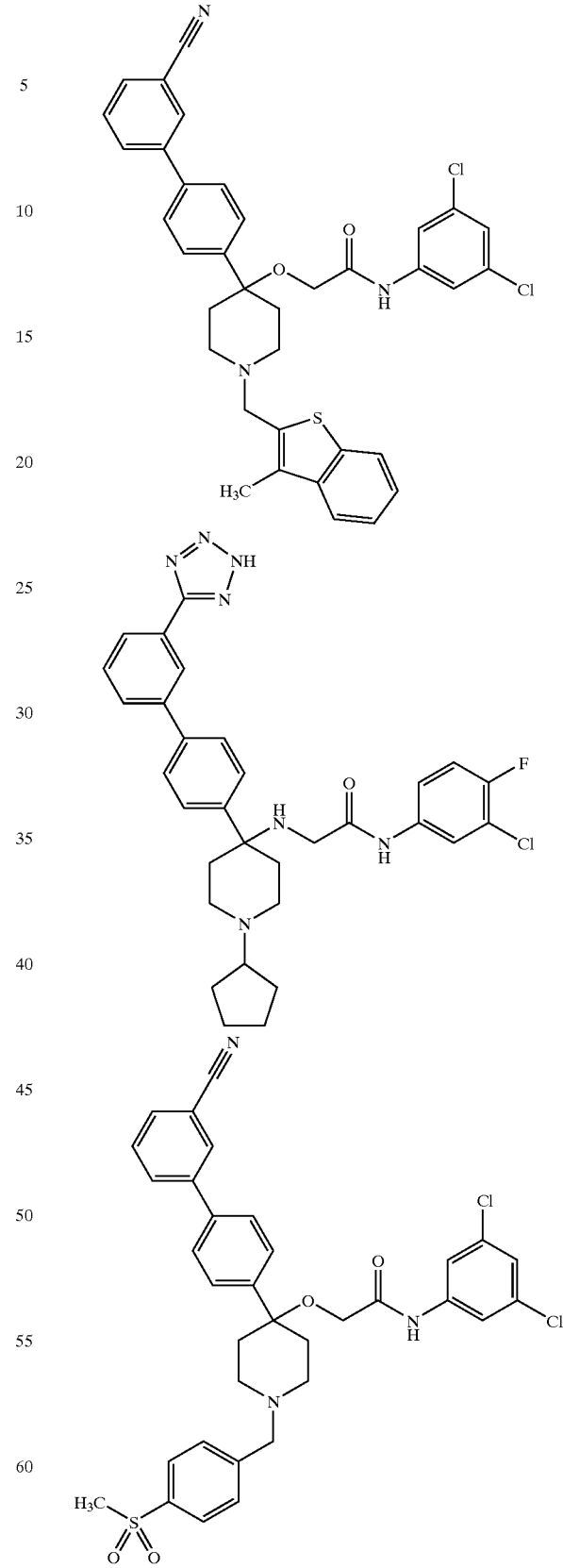

199
-continued
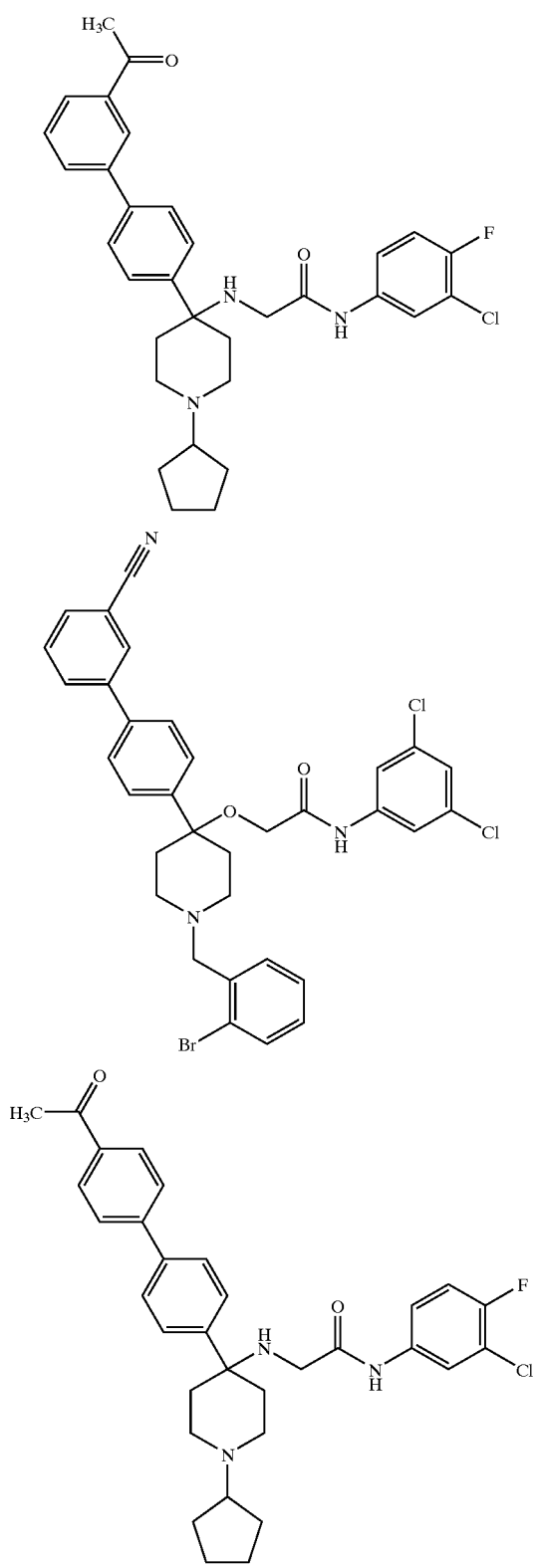
200
-continued
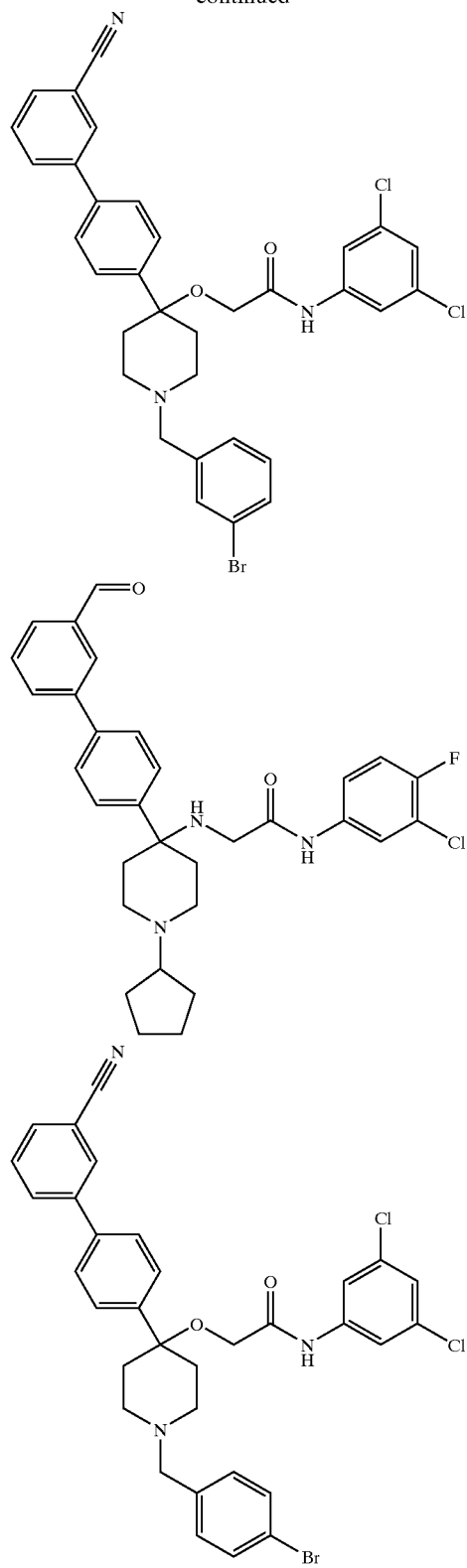

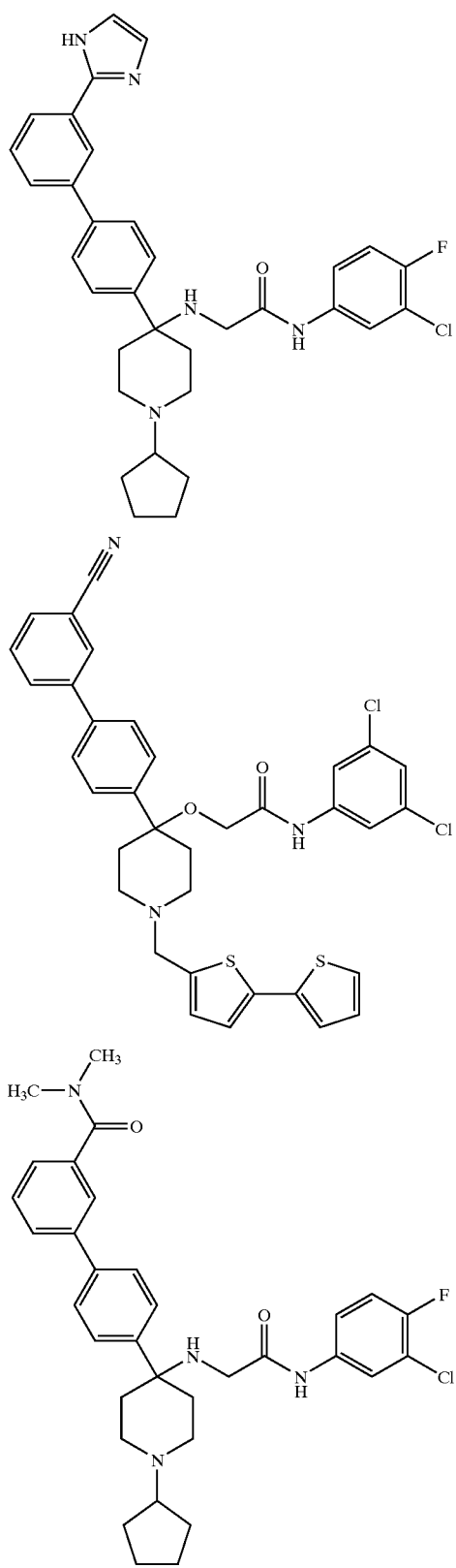
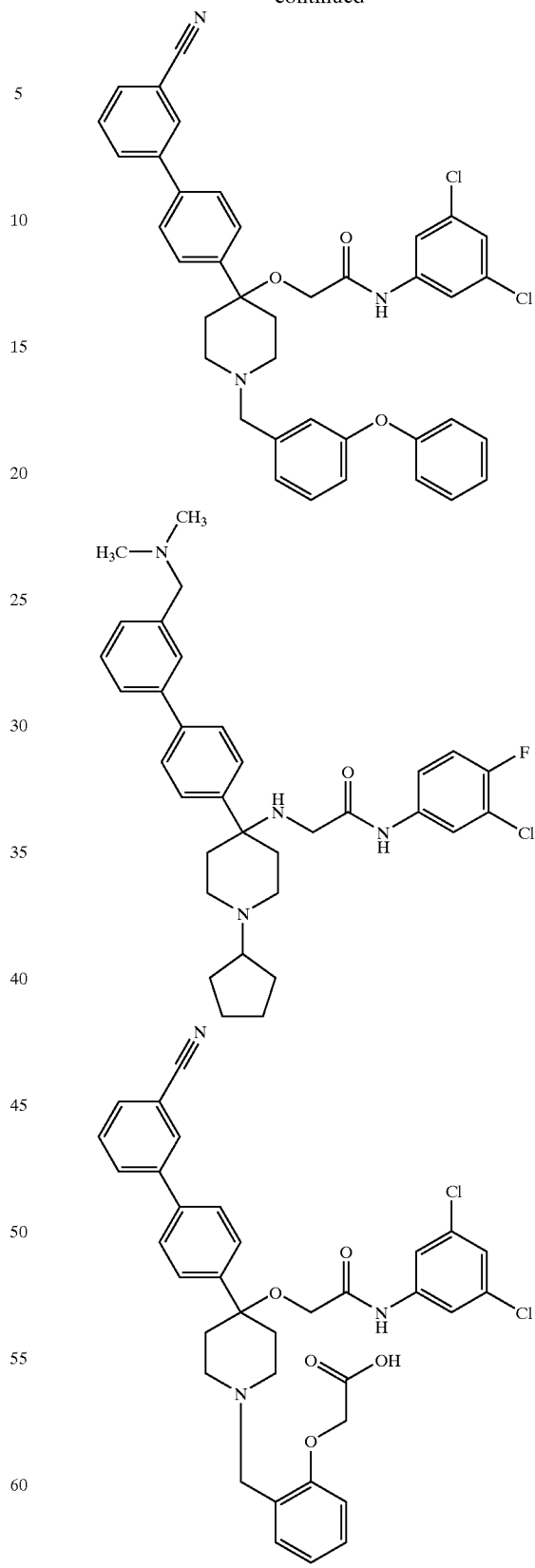

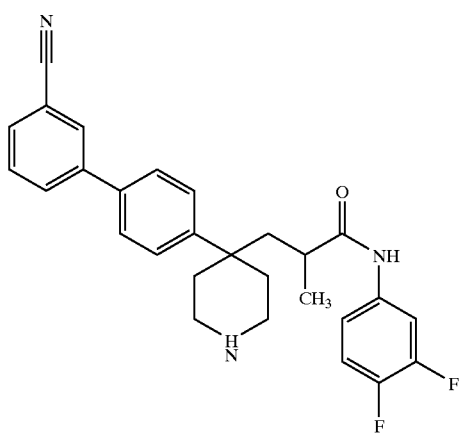
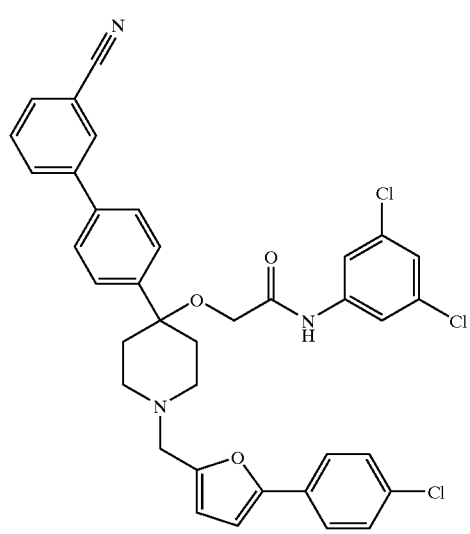
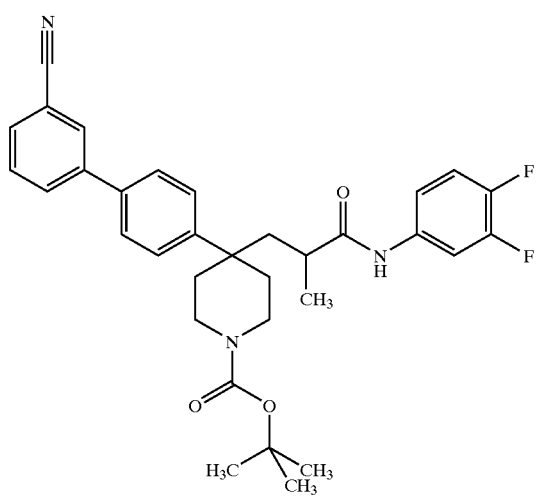
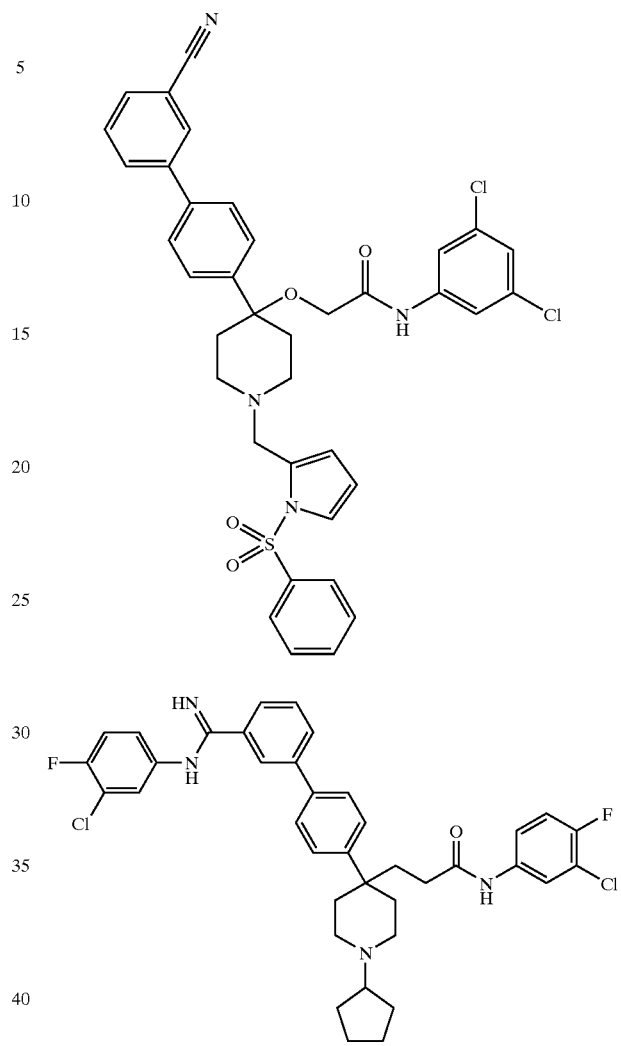
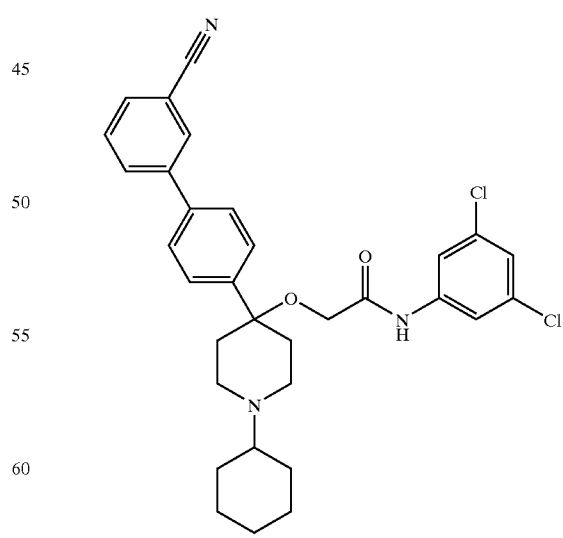

205
-continued
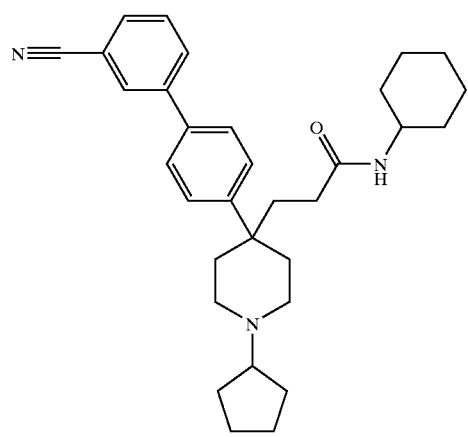
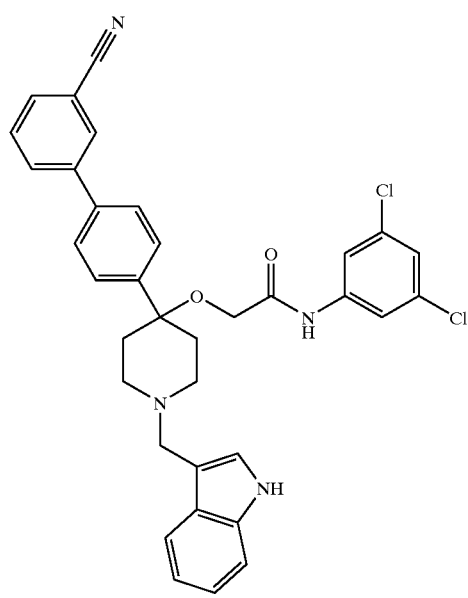
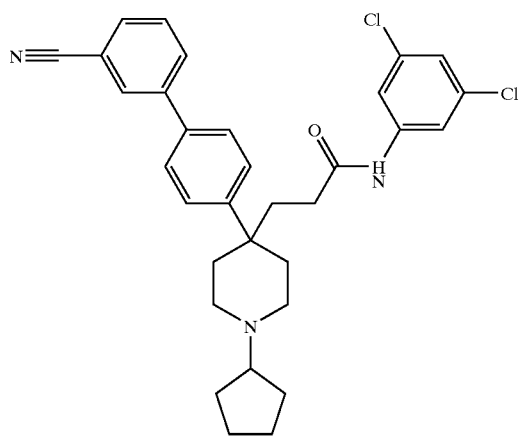
206
-continued
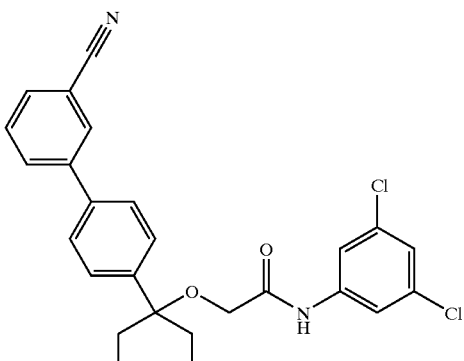
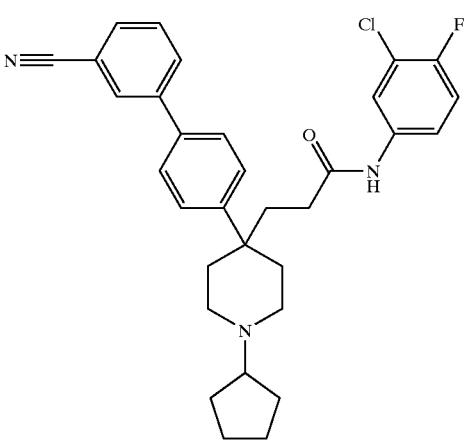
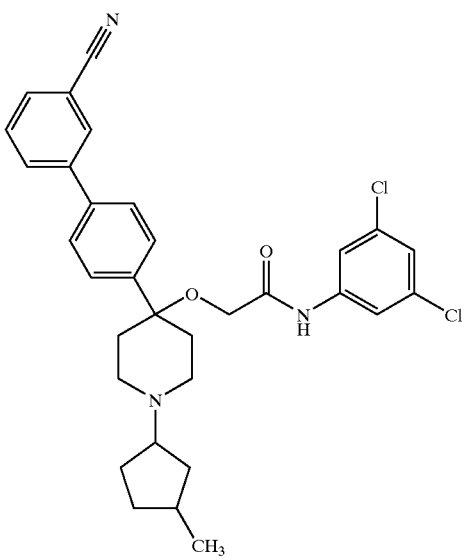

207
-continued
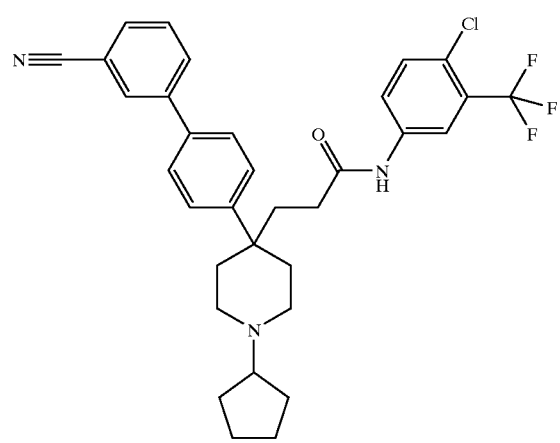
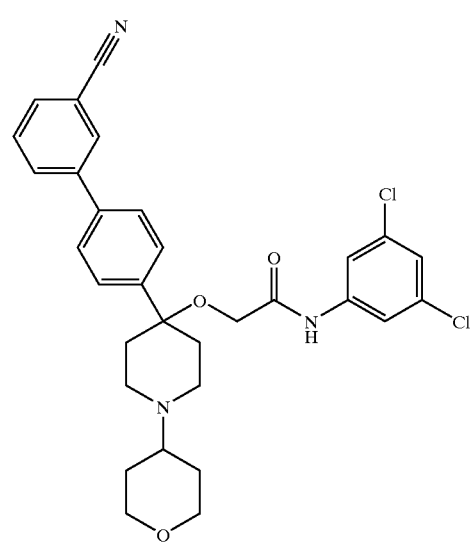
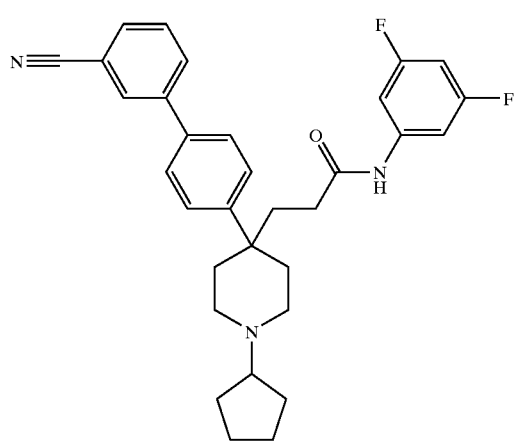
208
-continued
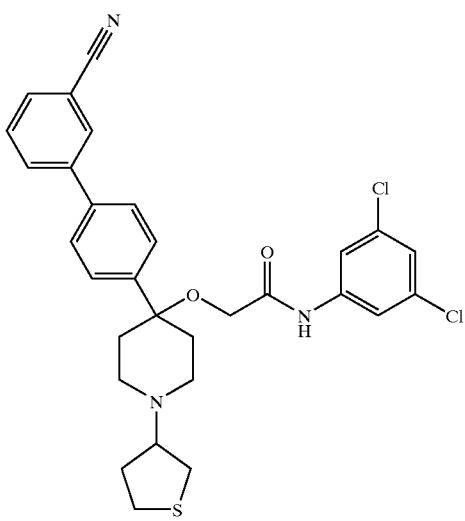
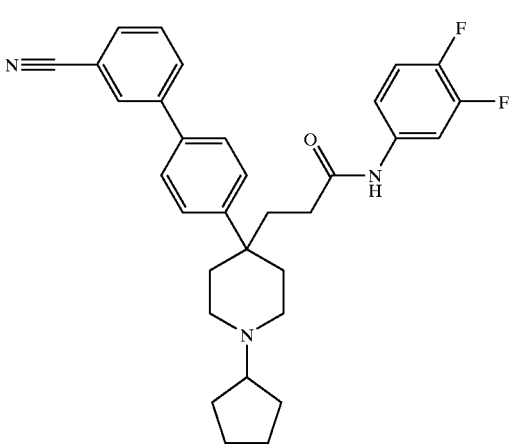
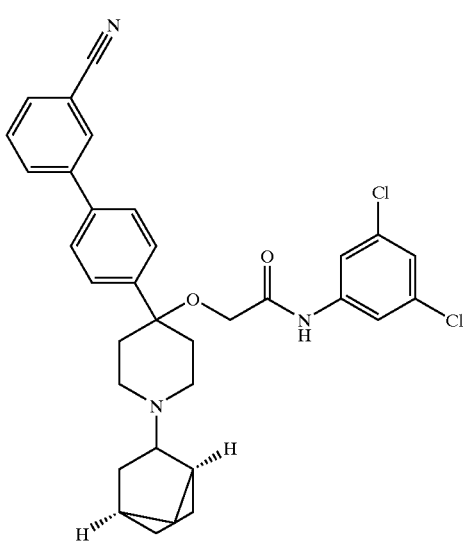

209
-continued
210
-continued
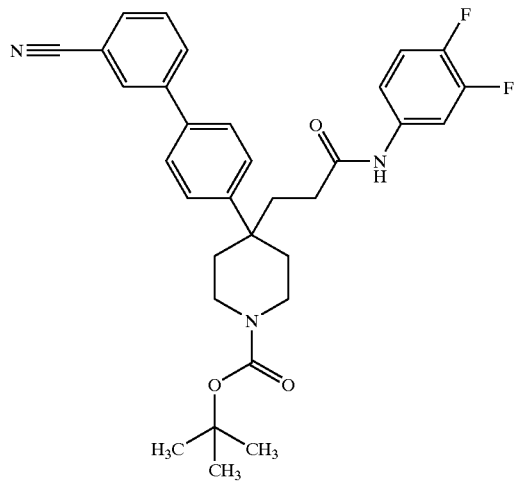
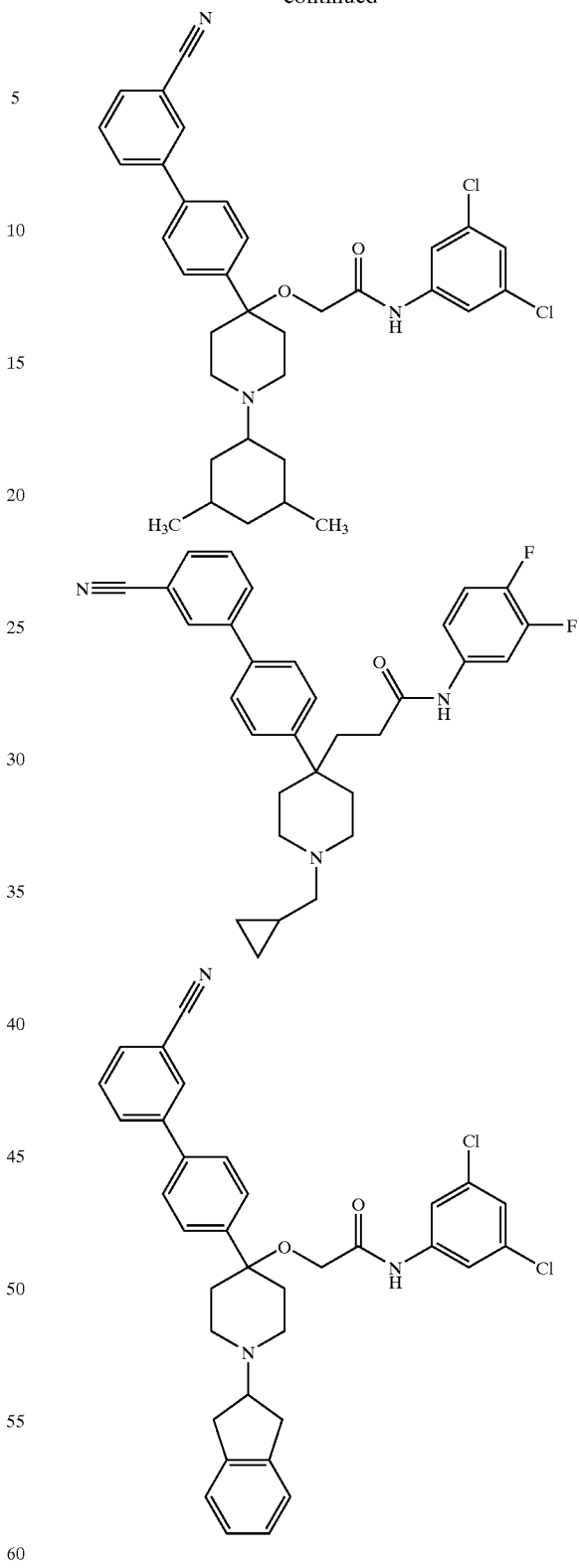

211
-continued
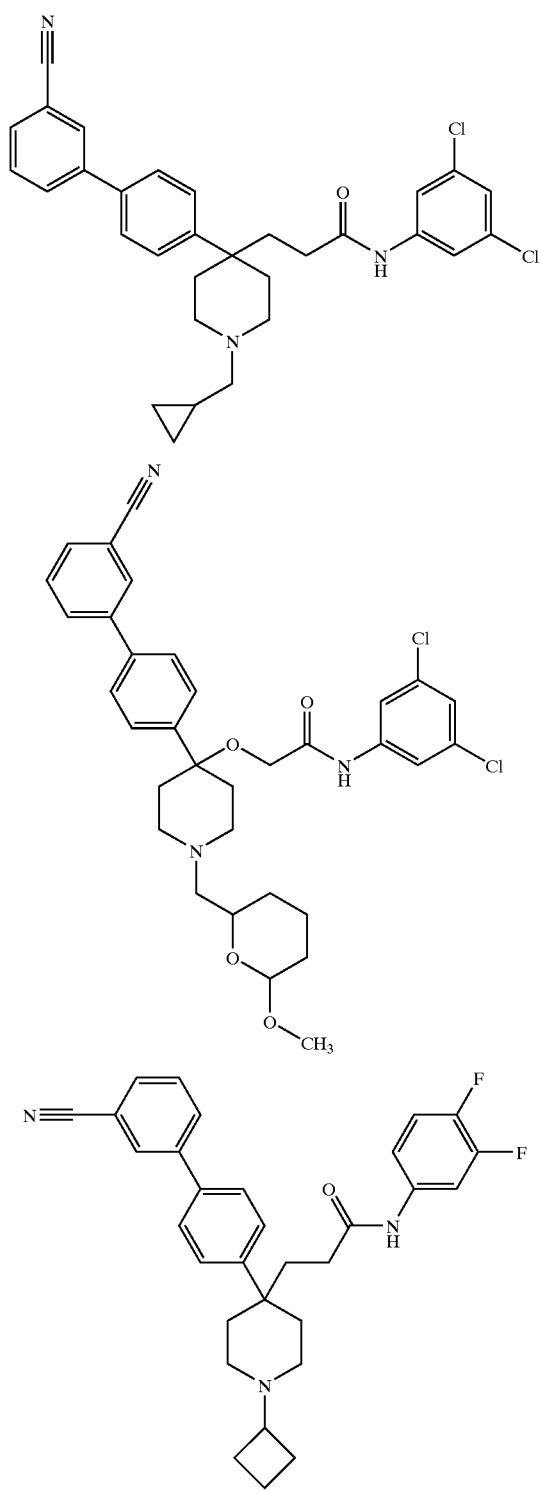
212
-continued
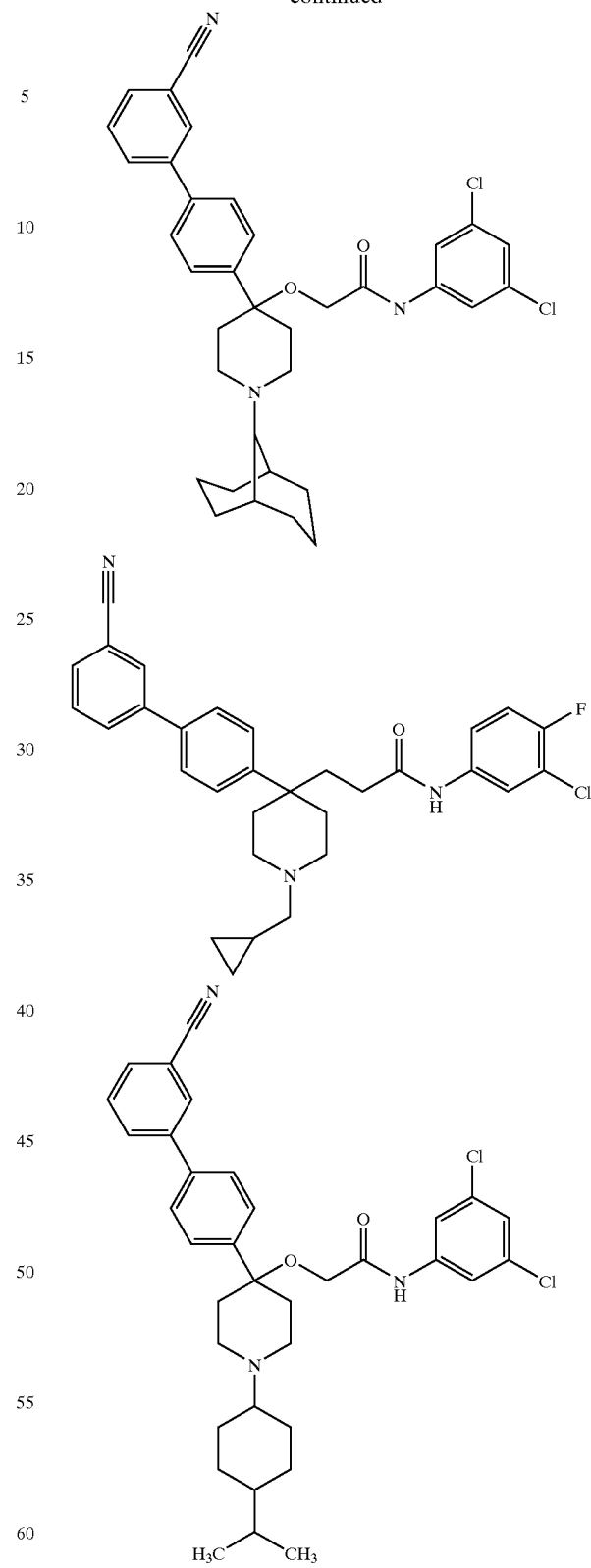

213
-continued
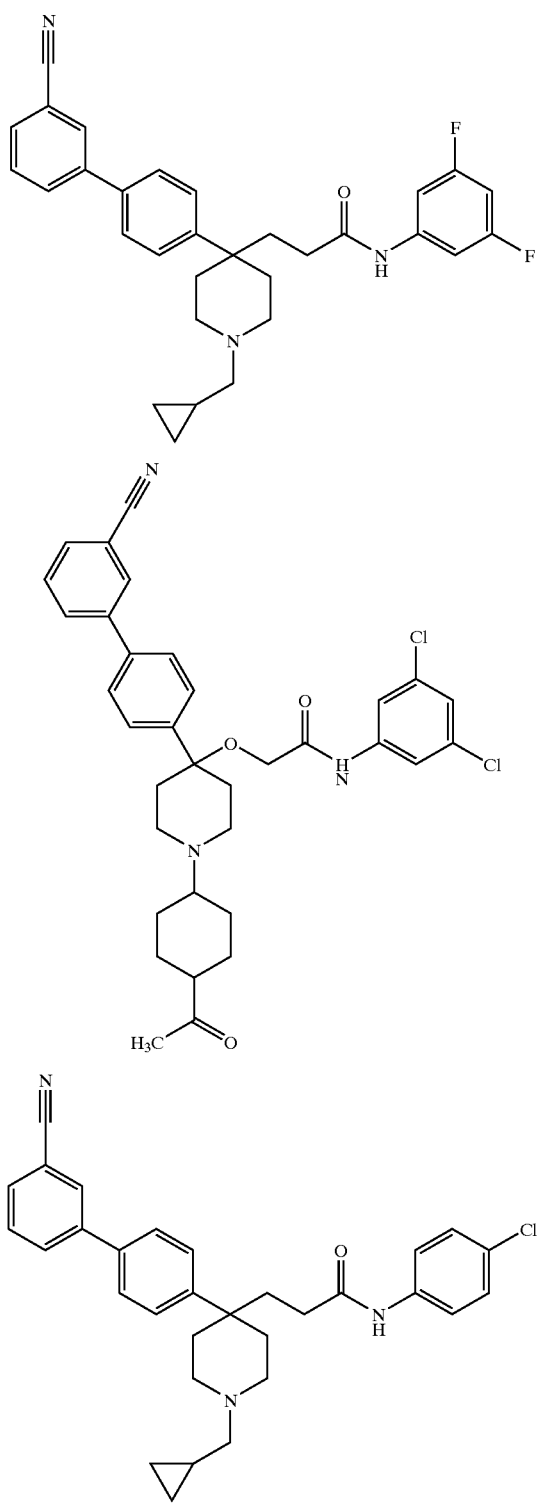
214
-continued
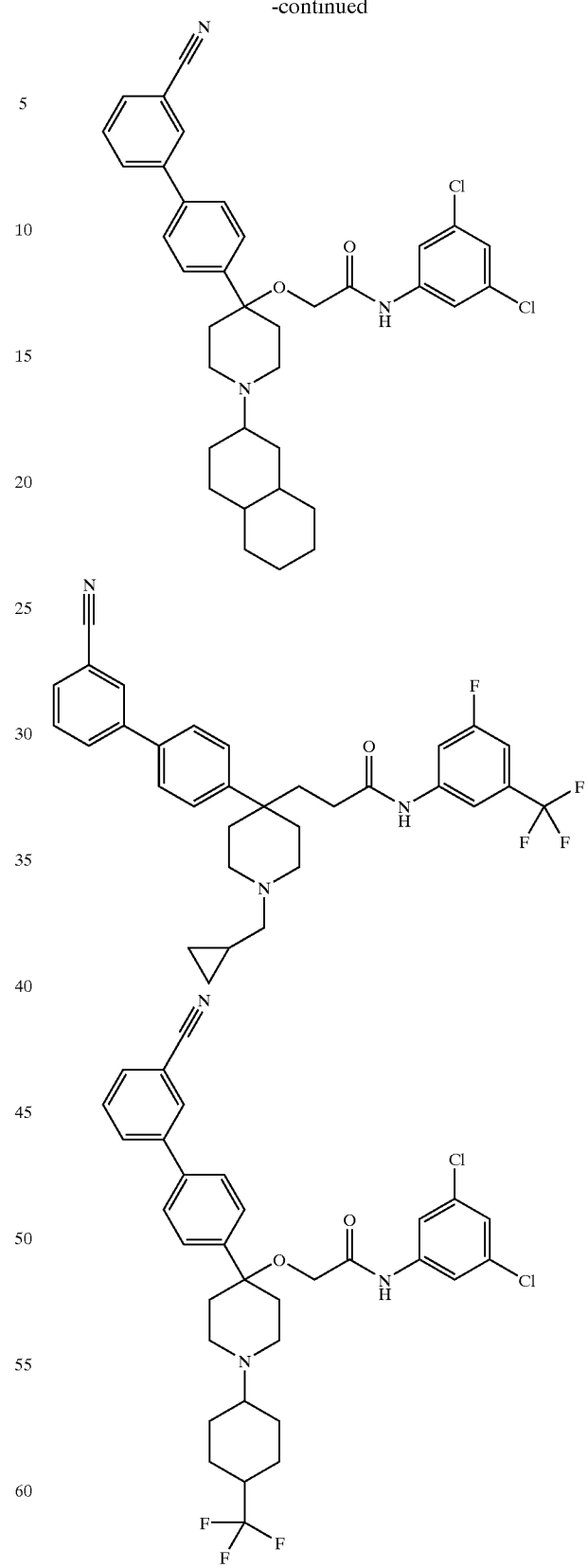

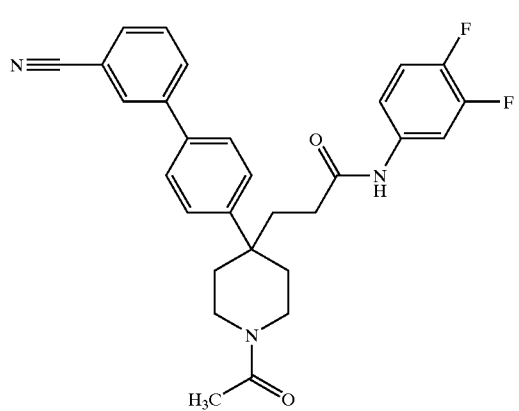
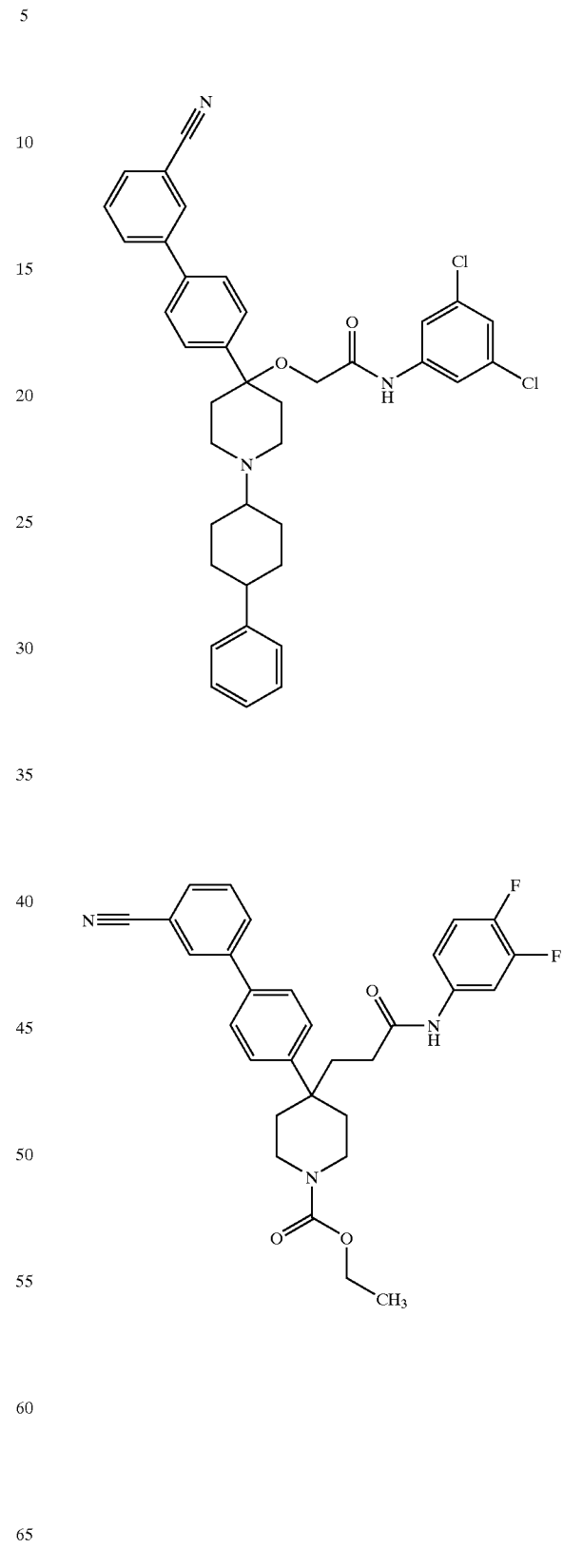

217
-continued
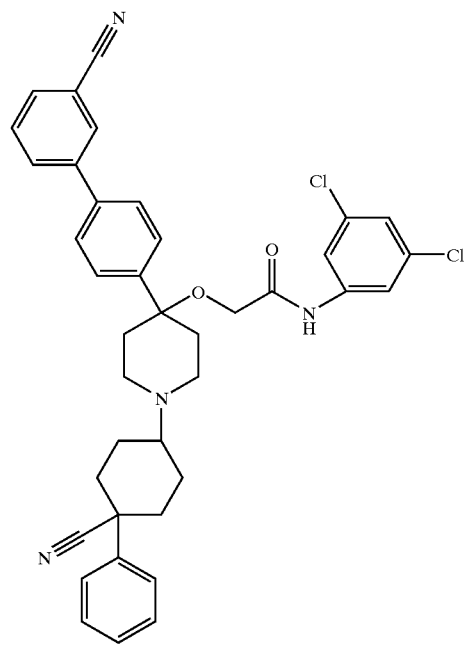
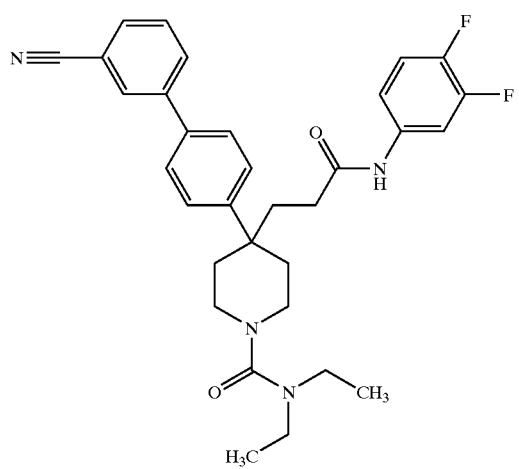
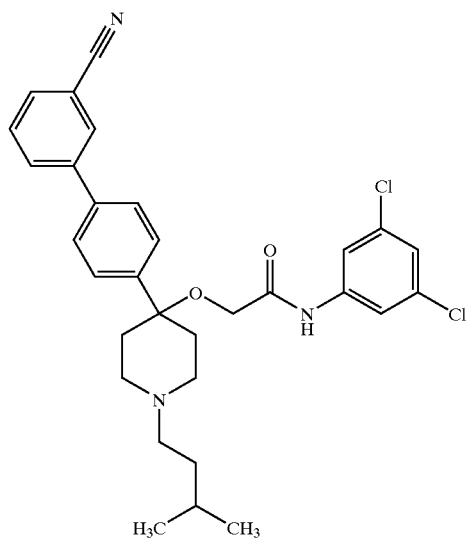
218
-continued
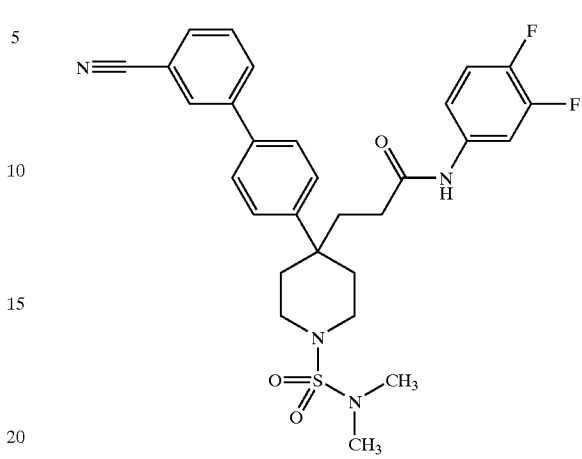
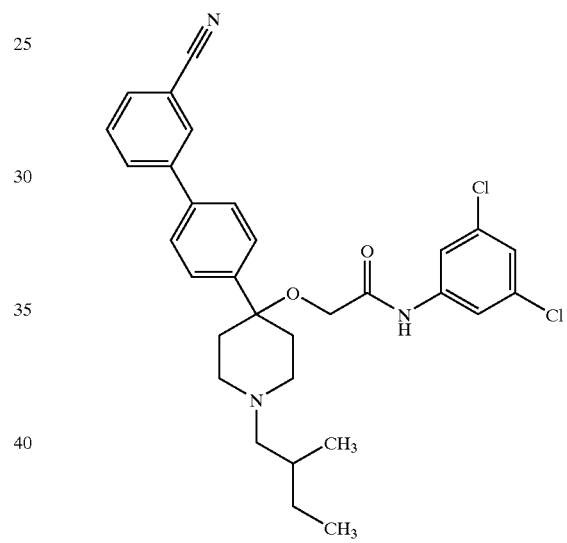
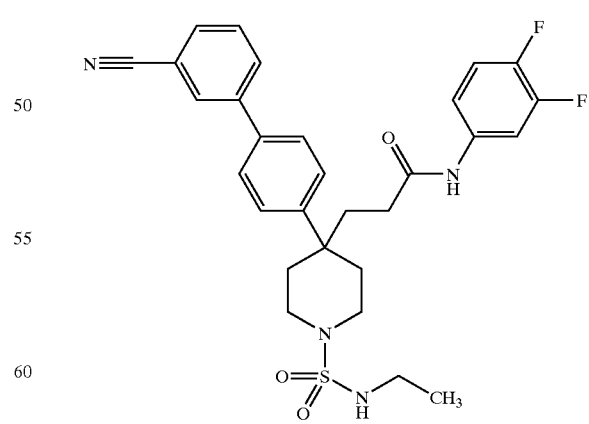

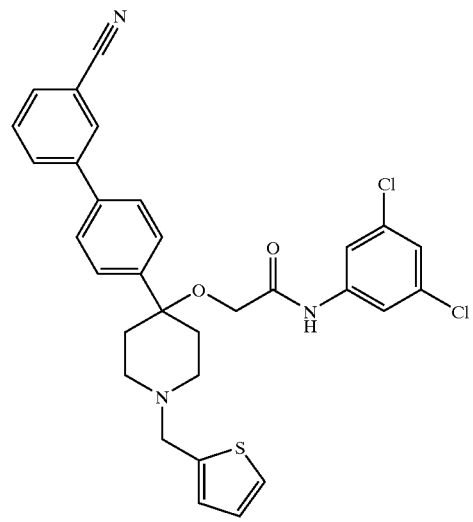
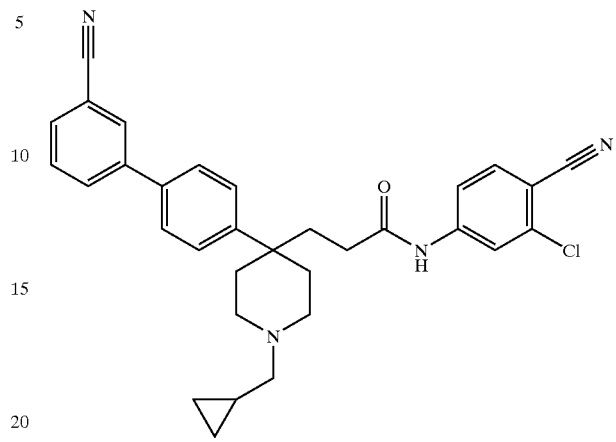
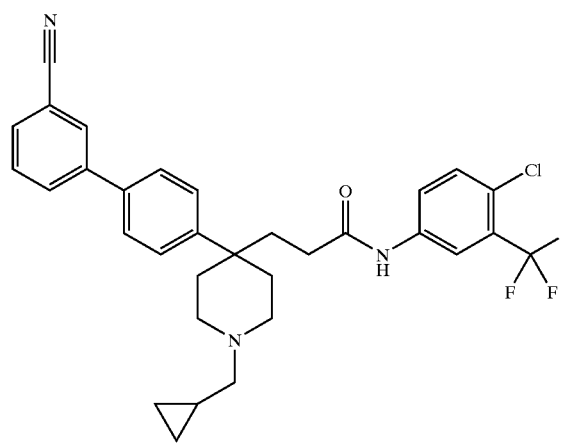
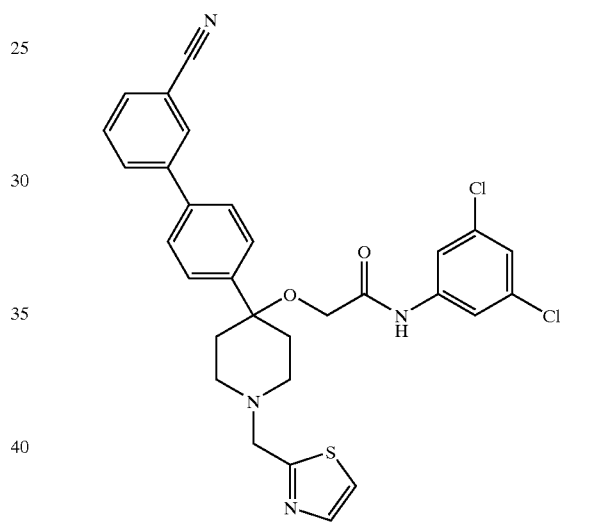
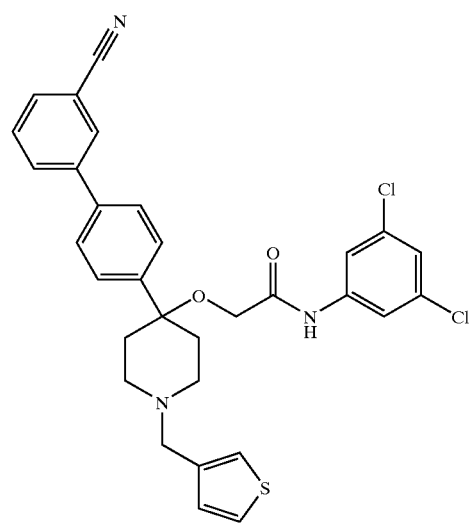
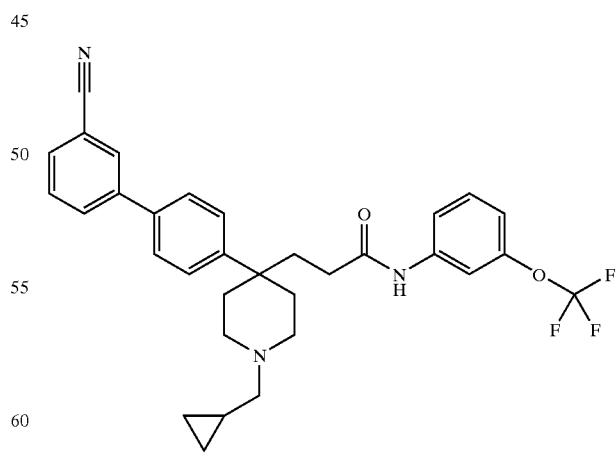

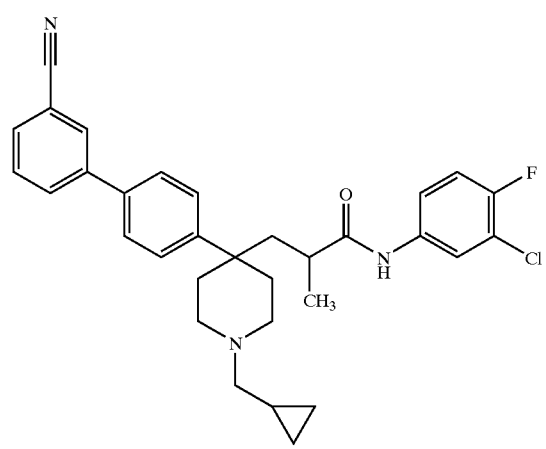

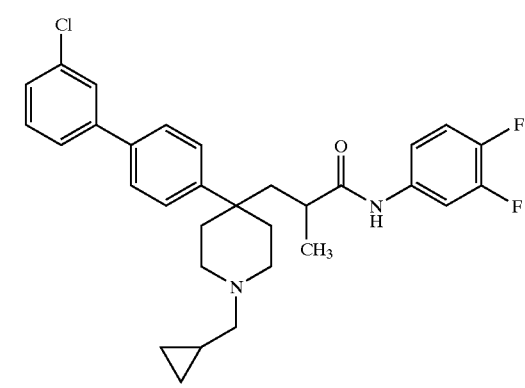

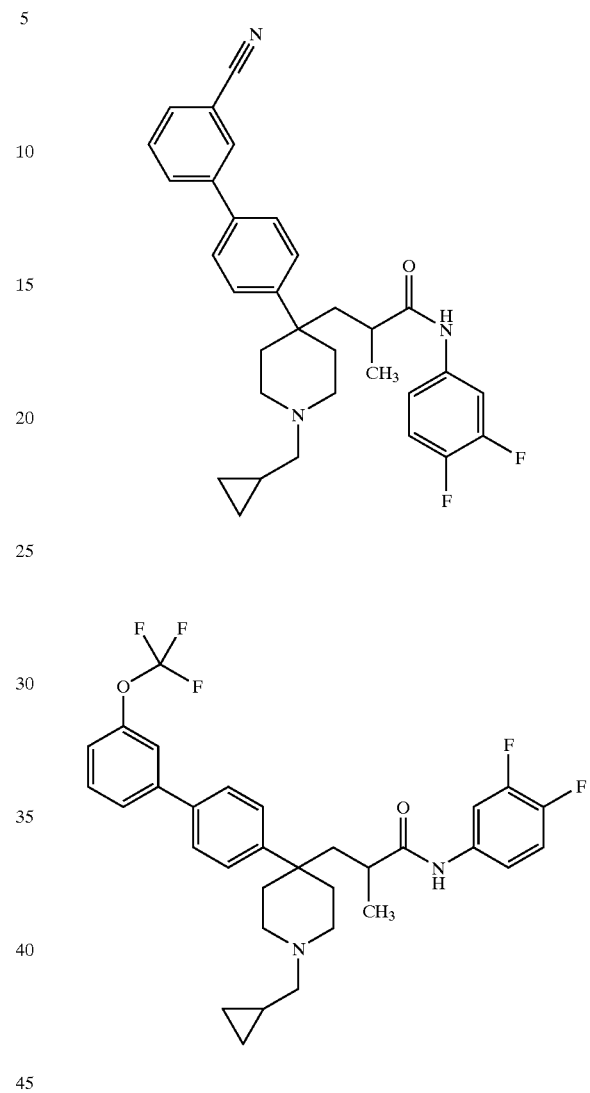

or a pharmaceutically acceptable salt or solvate of said compound.

9. A method of treating major depression, manic depression, anxiety, schizophrenia and sleep disorders comprising administering to a mammal in need of such treatment a therapeutically effective amount of at least one compound of claim 1 or a pharmaceutically acceptable salt or solvate of said compound.

10. A method of treating major depression, manic depression, anxiety, schizophrenia and sleep disorders comprising administering to a mammal in need of such treatment a therapeutically effective amount of at least one compound of claim 8 or a pharmaceutically acceptable salt or solvate of said compound.

11. A method of treating a metabolic disorder, eating disorder or diabetes comprising administering an effective amount of at least one compound of claim 1 to a patient in need of such treatment.

12. A method of treating a metabolic disorder, eating disorder or diabetes comprising administering an effective amount of at least one compound of claim 8 to a patient in need of such treatment.

13. The method of claim 11 wherein said eating disorder is hyperphagia.

14. The method of claim 12 wherein said eating disorder is hyperphagia.

15. The method of claim 11 wherein said metabolic disorder is obesity.

16. The method of claim 12 wherein said metabolic disorder is obesity.

17. A method of treating disorders associated with obesity comprising administering to a patient in need of such treatment a therapeutically effective amount of at least one compound of claim 1 or a pharmaceutically acceptable salt of said compound.

18. A method of treating disorders associated with obesity comprising administering to a patient in need of such treatment a therapeutically effective amount of at least one compound of claim 8 or a pharmaceutically acceptable salt of said compound.

19. The method of claim 17 wherein said disorders associated with obesity are type II diabetes, insulin resistance, hyperlipidemia and hypertension.

20. The method of claim 18 wherein said disorders associated with obesity are type II diabetes, insulin resistance, hyperlipidemia and hypertension.

21. A method of treating an eating disorder which comprises administering to a patient in need of such treatment
    an amount of a first compound, said first compound being a compound of claim 1, or a pharmaceutically acceptable salt of said compound;
    an amount of at least one more compound, said other compound (b) is selected from an antiobesity and/or anorectic agent such as a $\beta_3$ agonist, a thyromimetic agent, an anoretic agent, and an NPY antagonist;
wherein the amounts of the (a) and (b) compounds result in a therapeutic effect.

22. A method of treating an eating disorder which comprises administering to a patient in need of such treatment
    an amount of a first compound, said first compound being a compound of claim 8, or a pharmaceutically acceptable salt of said compound;
    an amount of at least one more compound, said other compound (b) is selected from an antiobesity and/or anorectic agent such as a $\beta_3$ agonist, a thyromimetic agent, an anoretic agent, and an NPY antagonist;
wherein the amounts of the (a) and (b) compounds result in a therapeutic effect.

23. A pharmaceutical composition which comprises a therapeutically effective amount of a composition comprising:
    a first compound, said first compound being a compound of claim 1, or a pharmaceutically acceptable salt of said compound;
    an amount of at least one more compound, said other compound (b) is selected from an antiobesity and/or anorectic agent such as a $\beta_3$ agonist, a thyromimetic agent, an anoretic agent, and an NPY antagonist; and
    a pharmaceutically acceptable carrier.

24. A pharmaceutical composition which comprises a therapeutically effective amount of a composition comprising:
    a first compound, said first compound being a compound of claim 8, or a pharmaceutically acceptable salt of said compound;
    an amount of at least one more compound, said other compound (b) is selected from an antiobesity and/or anorectic agent such as a $\beta_3$ agonist, a thyromimetic agent, an anoretic agent, and an NPY antagonist; and
    a pharmaceutically acceptable carrier.

25. A pharmaceutical composition which comprises a therapeutically effective amount of a composition comprising:
    a first compound, said first compound being a compound of claim 1, or a pharmaceutically acceptable salt of said compound;
    at least one other compound, selected from being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide and chlorpropamide; and
a pharmaceutically acceptable carrier.

26. A pharmaceutical composition which comprises a therapeutically effective amount of a composition comprising:
    a first compound, said first compound being a compound of claim 8, or a pharmaceutically acceptable salt of said compound;
    at least one other compound, selected from being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide and chlorpropamide; and
a pharmaceutically acceptable carrier.

27. A pharmaceutical composition comprising a therapeutically effective amount of at least one compound of claim 1, in combination with at least one pharmaceutically acceptable carrier.

28. A pharmaceutical composition comprising a therapeutically effective amount of at least one compound of claim 8 in combination with at least one pharmaceutically acceptable carrier.

29. A process for making a pharmaceutical composition comprising combining at least one compound of claim 1 and least one pharmaceutically acceptable carrier.

* * * * *